US011191769B2

United States Patent
Chan et al.

(10) Patent No.: US 11,191,769 B2
(45) Date of Patent: *Dec. 7, 2021

(54) FUSED THIOPHENE COMPOUNDS

(71) Applicant: BioTheryX, Inc., Chappaqua, NY (US)

(72) Inventors: Kyle W. H. Chan, San Diego, CA (US); Aparajita Hoskote Chourasia, San Diego, CA (US); Paul E. Erdman, San Diego, CA (US); Leah Fung, San Diego, CA (US); Frank Mercurio, Rancho Santa Fe, CA (US); Robert Sullivan, Vista, CA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/438,244

(22) Filed: Jun. 11, 2019

(65) Prior Publication Data

US 2020/0000814 A1   Jan. 2, 2020

Related U.S. Application Data

(60) Provisional application No. 62/684,495, filed on Jun. 13, 2018.

(51) Int. Cl.
  *C07D 495/04* (2006.01)
  *A61K 31/5377* (2006.01)
  *A61P 35/02* (2006.01)
  *A61K 31/454* (2006.01)

(52) U.S. Cl.
  CPC ........ *A61K 31/5377* (2013.01); *A61K 31/454* (2013.01); *A61P 35/02* (2018.01); *C07D 495/04* (2013.01)

(58) Field of Classification Search
  CPC  C07D 495/04; A61K 31/5377; A61K 31/454; A61P 35/02
  USPC ........................................................ 546/243
  See application file for complete search history.

(56) References Cited

U.S. PATENT DOCUMENTS

| | | | |
|---|---|---|---|
| 10,040,804 B2 * | 8/2018 | Chan | A61P 17/06 |
| 10,336,771 B2 * | 7/2019 | Chan | A61P 17/06 |
| 2016/0051530 A1 * | 2/2016 | Thakurta | A61K 31/573 424/451 |

OTHER PUBLICATIONS

Gowhar Ali, Input of Isosteric and Bioisosteric approach in Drug Design (Year: 2013).*
A review of Bioisosterism , Rakesh Bhatia et al (Year: 2011).*
Amit et al., 2002, Axin-mediated CKI phosphorylation of β-catenin at Ser 45: a molecular switch for the Wnt pathway, Genes & Development, 16:1066-1076.
Brito et al., 2005, Polyglycine expansions in eRF3/GSPT1 are associated with gastric cancer susceptibility, Carcinogenesis, 26(12):2046-2049.
Chauvin et al., Aug. 2007, Human eukaryotic release factor 3a depletion causes cell cycle arrest at $G_1$ phase through inhibition of the mTOR pathway, Mol. Cell. Bio., 27(16):5619-5629.
Cheong et al., 2011, Casein kinase 1: complexity in the family, J. Biochem. Cell Biol., 43:465-469.
Ciapetti et al., Jan. 2008, Chapter 15. Molecular variations based on isosteric replacements, in Wermuth ed., The Practice of Medicinal Chemistry, Third Edition, Elsevier, pp. 290-342.
Elyada et al., Feb. 17, 2011, CK1α ablation highlights a critical role for p53 in invasiveness control, Nature, 470:409-413.
Hashimoto et al., 2012, Translation termination factor eRF3 is targeted for caspase-mediated proteolytic cleavage and degradation during DNA damage-induced apoptosis, Apoptosis, 17:1287-1299.
Huart et al., Nov. 20, 2009, CK1α plays a central role in mediating MDM2 control of p53 and E2F-1 protein stability, J. Biol. Chem., 284(47):32384-32394.
Ishii et al., Jan. 27, 2017, A novel Rac1-GSPT1 signaling pathway controls astrogliosis following central nervous system injury, J. Biol. Chem., 292(4):1240-1250.
Levine et al., Oct. 2009, The first 30 years of p53: growing ever more complex, Nat. Rev. Cancer. 9(10):749-758.
Li et al., Jan. 2014, eRF3b, a biomarker for hepatocellular carcinoma, influences cell cycle and phosphoralation status of 4E-BP1, PLOS One, 9(1):e86371.
Malta-Vacas et al., 2009, Differential expression of GSPT1 $GGC_n$ alleles in cancer, Canc. Geneti. Cytogen., 195:132-142.
Matyskiela et al., Jan. 25, 2018, A cereblon modulator (CC-220) with improved degradation of ikaros and aiolos, Journal of Medicinal Chemistry, 61(2):535-542.
Miri et al., 2012, GGCn polymorphism of eRF3a/GSPT1 gene and breast cancer susceptibility, Med. Oncol., 29:1581-1585.
Schittek et al., 2014 Biological functions of casein kinase 1 isoforms and putative roles in tumorigenesis, Mol. Cancer., 13:231.
Schneider et al., Oct. 13, 2014, Role of casein kinase 1A1 in the biology and targeted therapy of del(5q) MDS, Cancer Cell, 26:509-520.
Stern, Mar. 2010, Prevalence of a history of skin cancer in 2007, Arch Dermatol., 146(3):279-282.
Wright et al., 2007, Newer potential biomarkers in prostate cancer, Rev. Urol., 9(4):207-213.
International Search Report and Written Opinion dated Sep. 24, 2019 in application No. PCT/US2019/036581.

* cited by examiner

*Primary Examiner* — Rita J Desai
(74) *Attorney, Agent, or Firm* — Lin Yu, Esq.; Juniv LLP

(57) ABSTRACT

The present disclosure provides compounds that modulate protein function, to restore protein homeostasis, and cell-cell adhesion. The disclosure provides methods of modulating protein-mediated diseases, such as cytokine-mediated diseases, disorders, conditions, or responses. Compositions, including in combination with other cytokine and inflammatory mediators, are provided. Methods of treatment, amelioration, or prevention of diseases, disorders, or conditions associated with a protein, are provided.

39 Claims, No Drawings

FUSED THIOPHENE COMPOUNDS

INCORPORATION BY REFERENCE TO PRIORITY APPLICATION

The present application claims the benefit of priority to U.S. Provisional Application No. 62/684,495, filed Jun. 13, 2018, which is hereby incorporated by reference in its entirety.

BACKGROUND

Field

Compounds, methods of making such compounds, pharmaceutical compositions and medicaments comprising such compounds, and uses of such compounds to treat, prevent or diagnose diseases, disorders, or conditions associated with protein malfunction are provided.

Aberrant protein function, and/or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Tumor necrosis factor-alpha (TNF-alpha, or TNF-α) and interleukin-1 (IL-1) are pro-inflammatory cytokines that mediate inflammatory responses associated with infectious agents and other cellular stresses. Overproduction of these cytokines is believed to underlie the progression of many inflammatory diseases including rheumatoid arthritis (RA), Crohn's disease, inflammatory bowel disease, endotoxin shock, osteoporosis, neurodegenerative diseases (such as multiple sclerosis, Alzheimer's disease, Parkinson's disease), congestive heart failure, and psoriasis among others.

Recent data from clinical trials support the use of protein antagonists of cytokines, for example soluble TNF-α receptor fusion protein (etanercept) or the monoclonal TNF-α antibody (infliximab), for the treatment of rheumatoid arthritis, Crohn's disease, juvenile chronic arthritis and psoriatic arthritis. Thus, the reduction of pro-inflammatory cytokines such as TNF-α and interleukin-1 (IL-I) has become an accepted therapeutic approach for potential drug intervention in these conditions.

Moreover, IL-2 is now FDA approved for the treatment of renal cancer and melanoma patients, with durable, complete remissions achieved with IL-2 up to 148 months. However, the short half-life of IL-2 in serum requires that large amounts of IL-2 be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional targets include several candidate genes involved in apoptosis and cell survival, including the translation termination factor GSPT1 (eRF3a), casein kinase 1α (CK1α), and the zinc-finger transcription factors aiolos, helios, and ikaros. Aiolos, helios, and ikaros are transcription factors whose expression is restricted to lymphoid lineages. For example, aiolos binds to the Bcl-2 promoter, and also interacts with the Bcl-2 and Bcl-XL proteins to promote cell survival. Upregulation of aiolos expression, for example, can reduce apoptosis of HIV-1 infected cells.

Likewise, expression of aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Similarly, aberrant ikaros and helios expression may promote Bcl-XL expression, driving the development of hematopoietic malignancies. Thus, downregulation of aiolos, ikaros, and/or helios may reduce or eliminate metastasis.

GSPT1 mediates stop codon recognition and facilitates release of a nascent peptide from the ribosome and is also involved in several other critical cellular processes, such as cell cycle regulation, cytoskeleton organization and apoptosis. Accordingly, decreased levels of GSPT1 may impair control of cell proliferation and facilitate cell migration and scar formation. Indeed, GSPT1 has been implicated as an oncogenic driver of several different cancer types, including breast cancer, hepatocellular carcinoma, gastric cancer, and prostate cancer. See, e.g., Brito, et al., *Carcinogenesis*, Vol. 26, No. 12, pp. 2046-49 (2005); Brito, et al., *Canc. Geneti. Cytogen.*, Vol. 195, pp. 132-42 (2009); Tavassoli, et al., *Med. Oncol.*, Vol. 29, pp. 1581-85 (2011); Wright and Lange, *Rev. Urol.*, Vol. 9, No. 4, pp. 207-213 (2007); Hoshino, et al., *Apoptosis*, Vol. 17, pp. 1287-99 (2012); Liu, et. al., PLOS One, Vol. 9, No. 1, e86371 (2014); and Jean-Jean, et al., *Mol. Cell. Bio.*, Vol. 27, No. 16, pp. 5619-29 (2007). GSPT1 also contributes to glial scar formation and astrogliosis after a central nervous system (CNS) injury. See, e.g., Ishii et al., *J. Biol. Chem.*, Vol. 292, No. 4, pp. 1240-50 (2017).

Casein kinase 1α (CK1α) is a component of the β-catenin-degradation complex and a critical regulator of the Wnt signaling pathway, and its ablation induces both Wnt and p53 activation. Schittek and Sinnberg, *Mol. Cancer.* 2014, 13, 231; Cheong and Virshup, *J. Biochem. Cell Biol.* 2011, 43, 465-469; Elyada et al., *Nature* 2011, 470, 409-413. CK1α phosphorylates β-catenin, which is subsequently further phosphorylated by GSK-3β. This destabilizes β-catenin and marks the protein for ubiquitination and proteasomal degradation. Thus, CK1α functions as a molecular switch for the Wnt pathway. Amit et al., *Genes Dev.* 2002, 16, 1066-1076. CK1α is critical for embryogenesis and plays an important role in tissue development and response to DNA damage, at least partly coordinated with p53. Elyada et al., *Nature* 2011, 470, 409-413; Schneider et al., *Cancer Cell* 2014, 26, 509-520. Levine and Oren, *Nat. Rev. Cancer* 2009, 9, 749-758.

Indeed, CK1α also phosphorylates p53, which inhibits binding to MDM2 (a p53 inhibitor) and stabilizes p53's binding interactions with the transcriptional machinery. Huart, et al., *J. Biol. Chem.* 2009, 284, 32384-32394. Thus, inhibiting CK1α activity increases cellular levels of p53. This is of particular importance for skin cancer, which has killed more people since 1980 than all other types of cancer combined. Stern, *Arch Dermatol.* 2010, 146, 279-282.

One mechanism to disrupt protein drivers of disease is to decrease the cellular concentration of these proteins. For example, proteolytic degradation of cellular proteins is essential to normal cell function. Hijacking this process, by targeting specific disease-related proteins, presents a novel mechanism for the treatment of disease. The irreversible nature of proteolysis makes it well-suited to serve as a regulatory switch for controlling unidirectional processes.

Ubiquitin-mediated proteolysis begins with ligation of one or more ubiquitin molecules to a particular protein substrate. Ubiquitination occurs through the activity of ubiquitin-activating enzymes (E1), ubiquitin-conjugating enzymes (E2), and ubiquitin-protein ligases (E3), acting sequentially to attach ubiquitin to lysine residues of substrate proteins. The E3 ligases confer specificity to ubiquitination reactions by binding directly to particular substrates.

SUMMARY

The compounds is the present disclosure have been discovered to exert surprising and unexpected biological effects. In particular, the compounds disclosed in the present application modulate protein function and/or modulate protein levels to restore protein homeostasis.

Some embodiments of the present disclosure provide a compound of Formula (I):

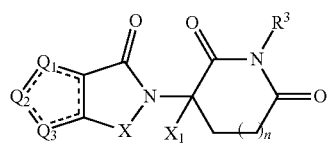

or a pharmaceutically acceptable salt thereof, wherein $Q_1$, $Q_2$, and $Q_3$, are independently $CR^1$, $CR^2$, or —S—; wherein one of $Q_1$, $Q_2$, and $Q_3$ is —S—; one of $Q_1$, $Q_2$, and $Q_3$ is $CR^1$; and one of $Q_1$, $Q_2$, and $Q_3$ is $CR^2$;

each ═══ is a carbon-carbon single bond, a carbon-carbon double bond, or a carbon-sulfur single bond;

$R^1$ is H, deuterium, hydroxyl, halogen, cyano, nitro, optionally substituted $C_1$-$C_6$ alkoxy, optionally substituted $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, optionally substituted amino, $C_1$-$C_6$ alkylamino, amino($C_1$-$C_6$ alkyl), ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_8$ carbocyclyl;

$R^2$ is

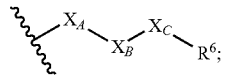

$R^3$ is H, deuterium, an optionally substituted $C_1$-$C_6$ alkyl,

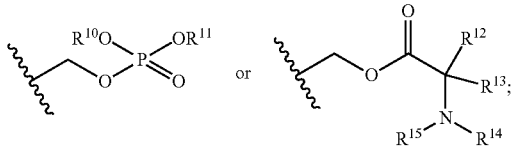

X is C═O, $CHR^{4A}$, or $CR^{4A}R^{4B}$;
each of $R^{4A}$ and $R^{4B}$ is independently H, deuterium, or $C_1$-$C_6$ alkyl;
$X_1$ is H, deuterium, fluoro, or $C_1$-$C_6$ alkyl;
each of $X_A$, $X_B$, and $X_C$ is independently a bond, $(CH_2)_m$, $(CF_2)_m$, O, S, and NH; wherein none of $X_A$—$X_B$, $X_A$—$X_C$, or $X_B$—$X_C$ is a bond selected from N—N, N—O, N—S, O—N, S—N, O—O, S—S, or N═N; wherein, not more than one of $X_A$, $X_B$, and $X_C$ can be a bond; and wherein any hydrogen of the $(CH_2)_m$ and NH groups can be substituted by one or more $R^5$;
$R^5$ is hydrogen, deuterium, halogen, $C_1$-$C_6$ alkyl, or $C_1$-$C_6$ haloalkyl;
m is 1, 2, or 3;
n is 0, 1, or 2;
$R^6$ is $C_6$-$C_{10}$ aryl, 5 to 10 membered heteroaryl, $C_3$ to $C_8$ carbocyclyl, or 3 to 10 membered heterocyclyl, each optionally substituted with one or more substituents independently selected from the group consisting of halogen, hydroxyl, optionally substituted $C_1$-$C_6$ alkyl, $C_1$-$C_6$ haloalkyl, $C_1$-$C_6$ alkoxy, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, $C_1$-$C_6$ alkylamino, amino($C_1$-$C_6$ alkyl), —C(═O)$NR^{16a}R^{16b}$, optionally substituted $C_3$-$C_7$ cycloalkyl, optionally substituted $C_3$-$C_7$ cycloalkyl($C_1$-$C_6$ alkyl), optionally substituted $C_6$-$C_{10}$ aryl, optionally substituted $C_6$-$C_{10}$ aryl($C_1$-$C_6$ alkyl), optionally substituted 5 to 10 membered heteroaryl, optionally substituted 5 to 10 membered heteroaryl($C_1$-$C_6$ alkyl), optionally substituted heterocyclyl, and optionally substituted heterocyclyl($C_1$-$C_6$ alkyl);
each $R^{16a}$ and $R^{16b}$ is independently H or $C_1$-$C_6$ alkyl, or $R^{16a}$ and $R^{16b}$ together with the nitrogen atom to which they are attached form 5 or 6 membered heterocyclyl optionally substituted with one or more $R^9$;
each $R^9$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^9$ form oxo (═O); and
each of $R^{10}$, $R^{11}$, $R^{12}$, $R^{13}$, $R^{14}$, and $R^{15}$ is independently H, an optionally substituted $C_1$-$C_6$ alkyl, or $C_3$-$C_6$ cycloalkyl; or $R^{14}$ and $R^{15}$ together with the nitrogen atom to which they are attached form an optionally substituted 5 or 6 membered heterocyclyl. In some embodiments, $R^6$ is $C_6$-$C_{10}$ aryl, 5 to 10 membered heteroaryl, $C_3$ to $C_8$ carbocyclyl, or 3 to 10 membered heterocyclyl, each optionally substituted with one or more substituents independently selected from the group consisting of halogen, hydroxyl, optionally substituted $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, amino($C_1$-$C_6$ alkyl), —C(=O)NR$^{16a}$R$^{16b}$, $C_3$-$C_7$ cycloalkyl optionally substituted with one or more R$^9$, $C_3$-$C_7$ cycloalkyl($C_1$-$C_6$ alkyl) optionally substituted with one or more R$^9$, $C_6$-$C_{10}$ aryl optionally substituted with one or more R$^9$, $C_6$-$C_{10}$ aryl($C_1$-$C_6$ alkyl) optionally substituted with one or more R$^9$, 5 or 6 membered heteroaryl optionally substituted with one or more R$^9$, 5 or 6 membered heteroaryl($C_1$-$C_6$ alkyl) optionally substituted with one or more R$^9$, heterocyclyl optionally substituted with one or more R$^9$, and heterocyclyl($C_1$-$C_6$ alkyl) optionally substituted with one or more R$^9$.

In some embodiments, the compound of Formula (I) is also represented by Formula (Ia), (Ib), (Ic), (Id), (Ie), or (If):

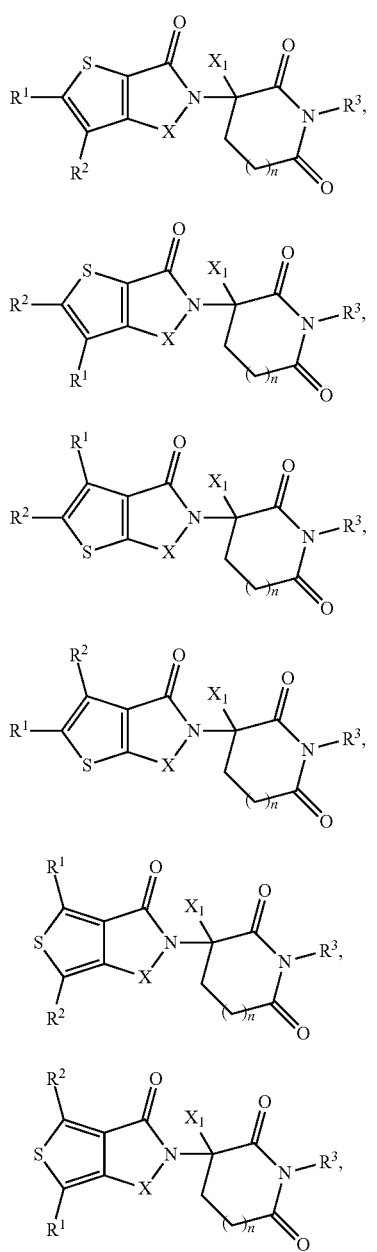

or a pharmaceutically acceptable salt thereof.

Some embodiments of the present disclosure provide a pharmaceutical composition, comprising a compound of Formula (I) or (Ia)-(If), or a pharmaceutically acceptable salt thereof, and at least one pharmaceutically acceptable carrier.

Some embodiments of the present disclosure provide a method of modulating the activity of a protein in a biological sample, comprising contacting the biological sample with a compound of Formula (I) or (Ia)-(If), or a pharmaceutically acceptable salt thereof, or a pharmaceutical composition thereof; wherein the protein is IL-1β, IL-2, IL-6, TNFα, CK1α, GSPT1, aiolos, ikaros, or helios. In some embodiments, the method inhibits the activity of the protein.

Some further embodiments the present disclosure provide a method of treating, ameliorating, or preventing a hematological malignancy or a solid tumor in a subject, the method comprising administering a therapeutically effective amount of a compound of Formula (I) or (Ia)-(If), or a pharmaceutically acceptable salt thereof, or a pharmaceutical composition thereof to the subject in need thereof. In some embodiments, the hematological malignancy or the solid tumor is associated with one or more proteins selected from a IL-1β, IL-2, IL-6, TNFα, CK1α, GSPT1, aiolos, ikaros, and helios, and combinations of any of the foregoing. In some further embodiments, the hematological malignancy is leukemia, lymphoma, or multiple myeloma.

Some further embodiments of the present disclosure provide a method of treating, ameliorating, or preventing a disease, disorder, or condition, the method comprising administering a therapeutically effective amount of a compound of Formula (I) or (Ia)-(If), or a pharmaceutically acceptable salt thereof, or a pharmaceutical composition thereof to the subject; wherein the disease, disorder, or condition is a neurodegenerative disease, fibrosis, lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, or chronic obstructive pulmonary disease. In some embodiments, the disease, disorder or condition is associated with one or more proteins selected from the group consisting of IL-1β, IL-2, IL-6, TNFα, CK1α, GSPT1, aiolos, ikaros, and helios, and combinations of any of the foregoing.

DETAILED DESCRIPTION

Disclosed herein are compounds useful for the treatment of various diseases, disorders, or conditions, such as inflammatory diseases and cancers. In some embodiments, these compounds are modulators of various protein activities, for example, a cytokine (such as IL-1β, IL-2, and IL-6), TNFα, aiolos, ikaros, helios, CK1α, or GSPT1. In some aspects, these compounds are inhibitors of the protein activities. In other aspects, certain compounds described herein may induce protein activities (e.g., IL-2).

The section headings used herein are for organizational purposes only and are not to be construed as limiting the subject matter described.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, common organic abbreviations are defined as follows:
ACN acetonitrile
AcOH acetic acid
$CCl_4$ carbon tetrachloride
CDI 1,1'-carbonyldiimidazole, N,N'-carbonyldiimidazole
d day, days
DCM dichloromethane, methylene chloride
DEAD diethyl azodicarboxylate
DIEA N,N-diisopropylethylamine
DMA N,N-dimethylamide
DMF N,N-dimethylformamide
DMSO dimethylsulfoxide
EDAC.HCl 1-(3-dimethylaminopropyl)-3-ethylcarbodiimide hydrochloride
EDCI 1-ethyl-3-(3-dimethylaminopropyl)carbodiimide
Ether diethyl ether
EA ethyl acetate
EtOH ethanol
$K_2CO_3$ potassium carbonate
LiAH lithium aluminium hydride
LiCl lithium chloride
LiOH lithium hydroxide
h hour, hours
$H_2$ hydrogen
HCl hydrochloric acid, hydrochloride
HOBt 1-hydroxybenzotriazole
MeOH MeOH
m minute, minutes
$NaHCO_3$ sodium bicarbonate
$Na_2SO_4$ sodium sulfate
NBS N-bromosuccinimide
$N_2$ nitrogen
Pd/C palladium on activated carbon
PE petroleum ether
RT room temperature
TEA triethylamine
TFA trifluoroacetic acid
THF tetrahydrofuran
quant quantitative yield The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

The terms "treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^a$ and $R^a$, and the atom to which it is attached, are indicated to be "taken together" or "joined together" it means that they are covalently bonded to one another to form a ring:

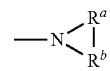

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from alkyl, cycloalkyl, aryl, heteroaryl, heterocyclyl, aralkyl, heteroaralkyl, heterocyclyl (alkyl), hydroxy, alkoxy, cycloalkoxy, aryloxy, acyl, mercapto, alkylthio, arylthio, cyano, halogen, C-amido, N-amido, C-carboxy, O-carboxy, isocyanato, thiocyanato, isothiocyanato, nitro, haloalkyl, haloalkoxy, amino, and alkylamino. When a group is not described as "optionally substituted," "unsubstituted" or "substituted," such group is unsubstituted unless the definition of such group states otherwise.

As used herein, "$C_a$ to $C_b$" in which "a" and "b" are integers refer to the number of carbon atoms in an alkyl group, or the number of ring atoms of a cycloalkyl, aryl, heteroaryl or heterocyclyl group. That is, the alkyl, ring of the cycloalkyl, and ring of the aryl, can contain from "a" to "b", inclusive, carbon atoms. Likewise, the ring of the heteroaryl and ring of the heterocyclyl can contain from "a" to "b", inclusive, total ring atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, cycloalkyl aryl, heteroaryl or heterocyclyl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro [3.3]heptane and spiro[4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

"Alkylene groups" are straight-chained —CH$_2$— tethering groups, forming bonds to connect molecular fragments via their terminal carbon atoms. Alkylene groups contain from 1 to 10 carbon atoms. Examples include but are not limited to methylene (—CH$_2$—), ethylene (—CH$_2$CH$_2$—), propylene (—CH$_2$CH$_2$CH$_2$—), and butylene (—CH$_2$CH$_2$CH$_2$CH$_2$—). An alkylene group can be substituted by replacing one or more hydrogen of the alkylene group with a substituent(s) listed under the definition of "substituted."

As used herein, "aralkyl" and "aryl(alkyl)" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

As used herein, "heterocyclyl(alkyl)" or "heterocyclylalkyl" refers to a heterocyclic or a heterocyclyl group, as defined above, connected, as a substituent, via an alkylene group, as defined above. The alkylene and heterocyclyl groups of a heterocyclyl(alkyl) may be substituted or unsubstituted. Examples include but are not limited to tetrahydrofuranylmethyl, piperazinylmethyl, and morpholinylethyl. When a heterocyclylalkyl group contains a secondary amino group (i.e., —NH—), the alkyl portion of the heterocyclylalkyl may replace the hydrogen on the nitrogen in the heterocyclyl ring, such that the heterocyclyl ring is linked to the alkyl portion of the heterocyclylalkyl group via the nitrogen atom.

As used herein, "cycloalkyl(alkyl)" refers to a cycloalkyl group, as defined above, connected, as a substituent, via an alkylene group, as defined above. The alkylene and cycloalkyl portion of a cycloalkyl(alkyl) may be substituted or unsubstituted. Examples include but are not limited to

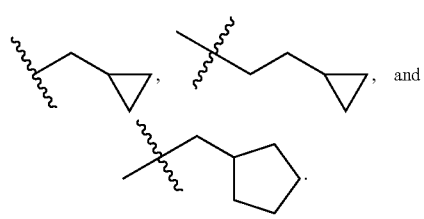

As used herein, "alkoxy" refers to the formula —OR wherein R is an alkyl group, as defined herein. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "cycloalkoxy" refers to the formula —OR wherein R is a cycloalkyl group, as defined herein. A non-limiting list of cycloalkoxys is cyclopropoxy, cyclobutoxy, cyclopentoxy, and cyclohexoxy. A cycloalkoxy may be substituted or unsubstituted.

As used herein, "acyl" refers to a hydrogen, alkyl, aryl, heteroaryl, or heterocyclyl group, as defined above, connected, as substituents, via a carbonyl group. Examples include formyl, acetyl, propanoyl, and benzoyl. An acyl may be substituted or unsubstituted. A "carbonyl" group refers to a C=O group.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl, 1-chloro-2-fluoromethyl, and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, and 2-fluoroisobutoxy. A haloalkoxy may be substituted or unsubstituted.

As used herein, "alkoxyalkyl" or "(alkoxy)alkyl" refers to an alkoxy group connected via an lower alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy)alkyl" refers to an alkoxy group connected via an —O— (lower alkylene) group, such as —O—($C_1$-$C_6$ alkoxy)$C_1$-$C_6$ alkyl, for example, —O—$(CH_2)_{1-3}$—$OCH_3$.

As used herein, "aryloxy" and "arylthio" refers to RO— and RS—, in which R is an aryl, as defined above, such as but not limited to phenyl. Both an aryloxy and arylthio may be substituted or unsubstituted.

As used herein, an "O-carboxy" group refers to a "RC(=O)O—*" group in which R can be hydrogen, alkyl, cycloalkyl, aryl, heteroaryl, heterocyclyl, aralkyl, or heterocyclyl(alkyl), as defined herein, and wherein "*" denotes the connect of the O-carboxy group to the rest of the molecule. An O-carboxy may be substituted or unsubstituted.

As used herein, "ester" and "C-carboxy" refer to a "*—C(=O)OR" group in which R can be hydrogen, alkyl, cycloalkyl, aryl, heteroaryl, heterocyclyl, aralkyl, or heterocyclyl(alkyl), as defined herein, and wherein "*" denotes the connect of the C-carboxy (or ester) group to the rest of the molecule. A C-carboxy or ester group may be substituted or unsubstituted.

As used herein, "amino" or "optionally substituted amino," as used herein refer to —$NR_AR_B$ where $R_A$ and $R_B$ are independently hydrogen, alkyl, cycloalkyl, aryl, heteroaryl, heterocyclyl, aralkyl, or heterocyclyl(alkyl), as defined herein. An unsubstituted amino is —$NH_2$.

As used herein, "alkylamino" or "(alkyl)amino" refers to "—$NR_AR_B$" where $R_A$ and $R_B$ are hydrogen or alkyl as defined above, and at least one of $R_A$ and $R_B$ is alkyl. The alkyl portion of the (alkyl)amino, includes, for example, $C_1$-$C_6$ alkyl groups. Examples of alkylamino groups include, but are not limited to methylamino (—NHMe), ethylamino (—NHEt), dimethylamino (—$N(Me)_2$), methylethylamino (—N(Me)(Et)), and isopropylamino (—NHiPr).

As used herein, "aminoalkyl" or "amino(alkyl)" refers to an alkyl group in which one or more of the hydrogen atoms are replaced by an amino group or "—$NRAR_B$" group as defined herein. The alkyl portion of the amino(alkyl), includes, for example, $C_1$-$C_6$ alkyl. Examples of aminoalkyl groups include, but are not limited to —$(CH_2)_{1-4}NH_2$, —$(CH_2)_{1-4}$—$NHCH_3$, —$(CH_2)_{1-4}$—$NHC_2H_5$, —$(CH_2)_{1-4}$—$N(CH_3)_2$, —$(CH_2)_{1-4}$—$N(C_2H_5)_2$, —$(CH_2)_{1-4}$—NH—$CH(CH_3)_2$, —$(CH_2)_{1-4}N(CH_3)C_2H_5$, and —$CH(NH_2)CH_3$.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "C-amido" group refers to a "*—C(=O)N($R_AR_B$)" group in which R and $R_A$ can be independently hydrogen, alkyl, cycloalkyl, aryl, heteroaryl, heterocyclyl, aralkyl, or heterocyclyl(alkyl), as defined above, and wherein "*" denotes the connect of the C-amido group to the rest of the molecule. A C-amido may be substituted or unsubstituted.

An "N-amido" group refers to a "RC(=O)N($R_A$)—*" group in which R and $R_A$ can be independently hydrogen, alkyl, cycloalkyl, aryl, heteroaryl, heterocyclyl, aralkyl, or heterocyclyl(alkyl), as defined above, and wherein "*" denotes the connect of the N-amido group to the rest of the molecule. An N-amido may be substituted or unsubstituted.

A "urea" group refers to a "—N($R_AR_B$)—C(=O)—N($R_AR_B$)—" group in which $R_A$ and $R_B$ can be independently hydrogen, alkyl, cycloalkyl, aryl, heteroaryl, heterocyclyl, aralkyl, or heterocyclyl(alkyl), as defined above. A urea group may be substituted or unsubstituted.

A "thiourea" group refers to a "—N($R_AR_B$)—C(=S)—N($R_AR_B$)—" group in which $R_A$ and $R_B$ can be independently hydrogen, alkyl, cycloalkyl, aryl, heteroaryl, heterocyclyl, aralkyl, or heterocyclyl(alkyl), as defined above. A thiourea group may be substituted or unsubstituted.

The term "halogen atom" or "halogen" as used herein, means any one of the radio-stable atoms of column 7 of the Periodic Table of the Elements, such as, fluorine, chlorine, bromine, and iodine.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W.

McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The term "prodrug" as used herein is a broad term, and is to be given its ordinary and customary meaning to a person of ordinary skill in the art (and is not to be limited to a special or customized meaning), and refers without limitation to a compound or a pharmaceutical composition that can be administered to a patient in a less active or inactive form, which can then be metabolized in vivo into a more active metabolite. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound. Certain compounds described herein are prodrugs.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

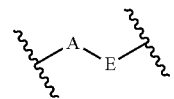

includes the substituent being oriented such that the A is attached at the leftmost attachment point of the molecule as well as the case in which A is attached at the rightmost attachment point of the molecule.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of pharmaceutically acceptable salts and/or conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond.

Likewise, it is understood that the compounds described herein, such as compounds of preferred embodiments, include the compound in any of the forms described herein (e.g., pharmaceutically acceptable salts, prodrugs, enantiomeric forms, tautomeric forms, and the like).

Compounds

Some embodiments provide a compound of Formula (I):

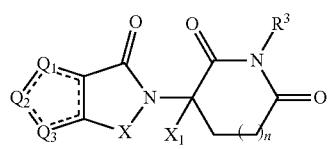
(I)

or a pharmaceutically acceptable salt thereof as described herein. In some embodiments, $R^1$ is H, deuterium, hydroxyl, halogen, cyano, nitro, an optionally substituted amino, an optionally substituted $C_1$-$C_6$ alkoxy, or an optionally substituted $C_1$-$C_6$ alkyl. In some embodiments, $R^5$ is hydrogen, deuterium, or methyl. In some embodiments, $R^6$ is

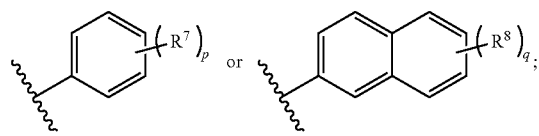

each of p and q is independently 1, 2, or 3; each of $R^7$ and $R^8$ is independently halogen, $C_1$-$C_6$ alkyl, $C_1$-$C_6$ haloalkyl, $C_1$-$C_6$ alkylamino, amino($C_1$-$C_6$ alkyl), heterocyclyl optionally substituted with one or more $R^9$, or heterocyclyl($C_1$-$C_6$ alkyl) optionally substituted with one or more $R^9$. In some further embodiments, each of $R^7$ and $R^8$ is independently halogen, $C_1$-$C_6$ alkyl, $C_1$-$C_6$ haloalkyl, $C_1$-$C_6$ alkylamino, unsubstituted heterocyclyl, heterocyclyl substituted with $C_1$-$C_6$ alkyl, unsubstituted heterocyclyl($C_1$-$C_6$ alkyl), and heterocyclyl($C_1$-$C_6$ alkyl) substituted with $C_1$-$C_6$ alkyl. In some further embodiments, $R^1$ is H, deuterium, hydroxyl, halogen, cyano, nitro, optionally substituted amino, optionally substituted $C_1$-$C_6$ alkoxy, or optionally substituted $C_1$-$C_6$ alkyl; $R^5$ is hydrogen, deuterium, or methyl; $R^6$ is

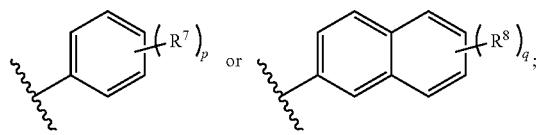

each of p and q is independently 1, 2, or 3; each $R^7$ and $R^8$ is independently halogen, $C_1$-$C_6$ alkyl, $C_1$-$C_6$ haloalkyl, $C_1$-$C_6$ alkylamino, unsubstituted heterocyclyl, heterocyclyl substituted with $C_1$-$C_6$ alkyl, unsubstituted heterocyclyl($C_1$-$C_6$ alkyl), and heterocyclyl($C_1$-$C_6$ alkyl) substituted with $C_1$-$C_6$ alkyl.

In some embodiments of the compound of Formula (I), the compound is also

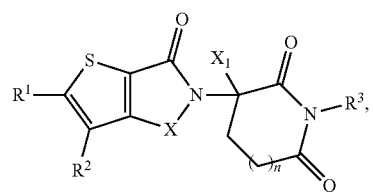

represented by Formula (Ia)

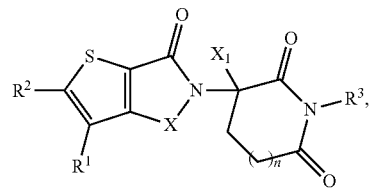

Formula (Ib) Formula (Ic)

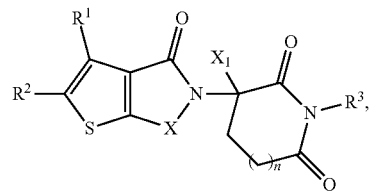

Formula (Id)

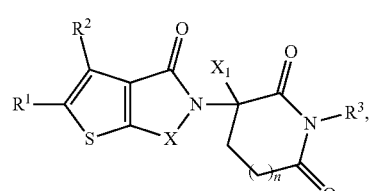

Formula (Ie)

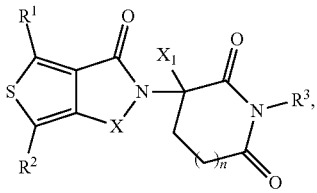

or Formula (If)

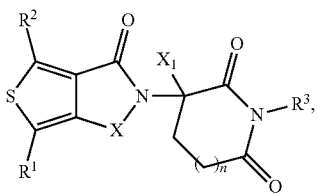

or a pharmaceutically acceptable salt of any of the foregoing. In one embodiment, the compound has Formula (Ia). In another embodiment, the compound has Formula (Ie).

In some embodiments of the compounds of Formula (I), (Ia), (Ib), (Ic), (Id), (Ie), or (If), n is 1. In other embodiments, n is 2. In still other embodiments, n is 0.

In some embodiments of the compounds of Formula (I), (Ia), (Ib), (Ic), (Id), (Ie), or (If), X is C=O. In other embodiments, X is $CHR^{4A}$. In still other embodiments, X is $CR^{4A}R^{4B}$. In some embodiments, each $R^{4A}$ is H or deuterium. In still other embodiments, each $R^{4A}$ is $C_1$-$C_6$ alkyl, for example, methyl, ethyl, n-propyl, isopropyl, n-butyl, sec-butyl, t-butyl, pentyl (straight chain or branched), or hexyl (straight chain or branched). In one embodiment, $R^{4A}$ is methyl. In some embodiments, each $R^{4B}$ is H or deuterium. In still other embodiments, each $R^{4B}$ is $C_1$-$C_6$ alkyl, such as those described herein. In some embodiments, each $R^{4B}$ is methyl. In one embodiment, both $R^{4A}$ and $R^{4B}$ are hydrogen.

In some embodiments of the compounds of Formula (I), (Ia), (Ib), (Ic), (Id), (Ie), or (If), $X_1$ is H. In some embodiments, $X_1$ is D. In some embodiments, $X_1$ is fluoro. In some embodiments, $X_1$ is $C_1$-$C_6$ alkyl, such as those described herein. In some embodiments, $X_1$ is methyl.

In some embodiments of the compounds of Formula (I), (Ia), (Ib), (Ic), (Id), (Ie), or (If), $R^3$ is H. In other embodiments, $R_3$ is deuterium or an optionally substituted $C_1$-$C_6$ alkyl, such as those described herein. In some embodiments, $R_3$ is methyl. In some other embodiments, $R^3$ is

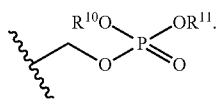

In some such embodiments, each $R^{10}$ and $R^{11}$ is independently H, $C_1$-$C_6$ alkyl or $C_3$-$C_6$ cycloalkyl (such as cyclopropyl, cyclobutyl, cyclopentyl, and cyclohexyl). In some such embodiments, at least one of $R^{10}$ and $R^{11}$ is H or $C_1$-$C_6$ alkyl. In one embodiment, both $R^{10}$ and $R^{11}$ are $C_1$-$C_6$ alkyl (e.g., isopropyl). In some other embodiments, $R_3$ is

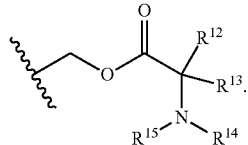

In some such embodiments, each $R^{12}$ and $R^{13}$ is independently H, $C_1$-$C_6$ alkyl or $C_3$-$C_6$ cycloalkyl, such as those described herein. In some such embodiments, at least one of $R^{12}$ and $R^{13}$ is H or $C_1$-$C_6$ alkyl. In one embodiment, both $R^{12}$ and $R^{13}$ are H. In another embodiment, $R^{12}$ is H and $R^{13}$ is $C_1$-$C_6$ alkyl (e.g., isopropyl). In some such embodiments, each $R^{14}$ and $R^{15}$ is independently H, $C_1$-$C_6$ alkyl or $C_3$-$C_6$ cycloalkyl, such as those described herein. In some such embodiments, at least one of $R^{14}$ and $R^{15}$ is H or $C_1$-$C_6$ alkyl. In one embodiment, both $R^{14}$ and $R^{15}$ are H. In other embodiments, $R^{14}$ and $R^{15}$ together with the nitrogen atom to which they are attached form an optionally substituted 5 or 6 membered heterocyclyl, for example, a 5 or 6 membered monocyclic heterocyclyl group containing one or two nitrogen atoms, one or two oxygen atoms, or one nitrogen atom and one oxygen atom. In some further embodiments, $R^{14}$ and $R^{15}$ come together to form a pyrrolidine, a piperidine, a piperazine, or a morpholine.

In some embodiments of the compounds of Formula (I), (Ia), (Ib), (Ic), (Id), (Ie), or (If), $R^1$ is an optionally substituted $C_1$-$C_6$ alkyl including $C_1$-$C_6$ haloalkyl (such as trifluoromethyl), an optionally substituted $C_1$-$C_6$ alkoxy including $C_1$-$C_6$ haloalkoxy (such as methoxy, trifluoromethoxy, ethoxy, n-propoxy, isopropoxy, n-butoxy, sec-butoxy, t-butoxy, pentoxy (straight chain or branched), or hexoxy (straight chain or branched)), or an optionally substituted amino (such as an unsubstituted amino, or an amino substituted with one or two groups selected from $C_1$-$C_6$ alkyl, $C_3$-$C_6$ cycloalkyl, phenyl, 3 to 6 membered heterocyclyl, or 5 to 6 membered heteroaryl). In other embodiments, $R^1$ is halogen. In other embodiments, $R^1$ is H.

In some embodiments of the compounds of Formula (I), (Ia), (Ib), (Ic), (Id), (Ie), or (If), $R^2$ is

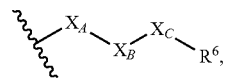

where $X_A$ is a bond; $X_B$ is O, S, NH, $(CF_2)_m$ or $(CH_2)_m$; and $X_C$ is $(CF_2)_m$ or $(CH_2)_m$. In some other embodiments, $X_A$ is $(CF_2)_m$ or $(CH_2)_m$; $X_B$ is O, S, NH, $(CF_2)_m$ or $(CH_2)_m$; and $X_C$ is a bond. In some other embodiments, $X_A$ is $(CH_2)_m$; $X_B$ is O, S, or NH; and $X_C$ is $(CH_2)_m$. In any of the embodiments, NH is optionally substituted with one $R^5$, e.g., methyl. In any of the embodiments, $(CH_2)_m$ is optionally substituted by one or two $R^5$, e.g., methyl or halogen. In any of the embodiments, m is 1, 2, or 3. In one embodiment, m is 1. In another embodiment, m is 2.

In some embodiments of the compounds of Formula (I), (Ia), (Ib), (Ic), (Id), (Ie), or (If), $R^2$

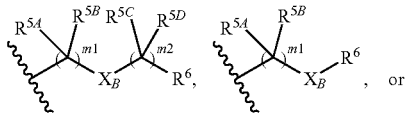

, or

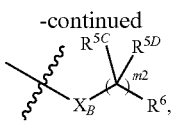

is where $X_B$ is a bond, O, S, or $NR^{5E}$; each of $R^{5A}$, $R^{5B}$, $R^{5C}$, $R^{5D}$, and $R^{5E}$ is independently hydrogen, deuterium, halo, $C_1$ to $C_6$ alkyl, or $C_1$-$C_6$ haloalkyl; and each m1 and m2 is independently 1, 2, or 3. In some embodiments, $R^2$ is

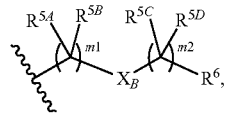

and wherein each m1 and m2 is independently 1 or 2. In some such embodiments, $X_B$ is a bond, O, or $NR^{5E}$. In some embodiments, $R^2$ is

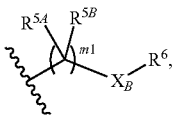

wherein m1 is 1 or 2. In some such embodiments, $X_B$ is O or $NR^{5E}$. In some embodiments, $R^2$ is

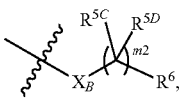

wherein m2 is 1 or 2. In some such embodiments, $X_B$ is O or $NR^{5E}$. In some embodiments, each of $R^{5A}$, $R^{5B}$, $R^{5C}$, $R^{5D}$, and $R^{5E}$ is independently hydrogen, deuterium, or $C_1$-$C_6$ alkyl (e.g., methyl). In some embodiments, each of $R^{5A}$, $R^{5B}$, $R^{5C}$, $R^{5D}$ is independently hydrogen, deuterium, halogen, or $C_1$-$C_6$ alkyl. In one embodiment, each of $R^{5A}$, $R^{5B}$, $R^{5C}$, $R^{5D}$ is hydrogen. In other embodiments, at least one of $R^{5A}$, $R^{5B}$, $R^{5C}$, $R^{5D}$ is halogen or $C_1$-$C_6$ alkyl. In any such embodiments, $R^{5E}$ is independently hydrogen or methyl.

In some further embodiments, $X_A$, $X_B$, and $X_C$ are selected as shown in Table A below.

TABLE A

| $X_A$ | $X_B$ | $X_C$ |
|---|---|---|
| $(CH_2)_{1-3}$ | $(CH_2)_{1-3}$ | $(CH_2)_{1-3}$ |
| $(CH_2)_{1-3}$ | NH | $(CH_2)_{1-3}$ |
| $(CH_2)_{1-3}$ | O | $(CH_2)_{1-3}$ |
| $(CH_2)_{1-3}$ | S | $(CH_2)_{1-3}$ |
| $(CH_2)_{1-3}$ | Bond | $(CH_2)_{1-3}$ |
| $(CH_2)_{1-3}$ | $(CH_2)_{1-3}$ | NH |
| $(CH_2)_{1-3}$ | $(CH_2)_{1-3}$ | O |
| $(CH_2)_{1-3}$ | $(CH_2)_{1-3}$ | S |
| $(CH_2)_{1-3}$ | $(CH_2)_{1-3}$ | Bond |
| NH | $(CH_2)_{1-3}$ | $(CH_2)_{1-3}$ |
| NH | $(CH_2)_{1-3}$ | Bond |
| NH | $(CH_2)_{1-3}$ | O |
| NH | $(CH_2)_{1-3}$ | NH |
| NH | $(CH_2)_{1-3}$ | S |
| NH | Bond | $(CH_2)_{1-3}$ |
| O | $(CH_2)_{1-3}$ | $(CH_2)_{1-3}$ |
| O | $(CH_2)_{1-3}$ | Bond |
| O | $(CH_2)_{1-3}$ | O |
| O | $(CH_2)_{1-3}$ | NH |
| O | Bond | $(CH_2)_{1-3}$ |
| Bond | NH | $(CH_2)_{1-3}$ |
| Bond | O | $(CH_2)_{1-3}$ |
| Bond | $(CH_2)_{1-3}$ | NH |
| Bond | $(CH_2)_{1-3}$ | O |
| Bond | $(CH_2)_{1-3}$ | S |

In some embodiments of the compounds of Formula (I), (Ia), (Ib), (Ic), (Id), (Ie), or (If), $R^6$ is an optionally substituted phenyl, optionally substituted 5 to 10 membered heteroaryl (e.g., five or six-membered heteroaryl containing one, two or three heteroatoms selected from O, N or S; including but not limited to pyridyl, pyrimidyl, thienyl, furyl, pyrrolyl, pyrazolyl, imidazolyl, thiazolyl, isothiazolyl, diathiazolyl, oxazolyl, and isoxazolyl), optionally substituted $C_3$ to $C_8$ carbocyclyl (e.g., cyclopropyl, cyclobutyl, cyclopentyl, or cyclohexyl), or optionally substituted 3 to 10 membered heterocyclyl (e.g., four to six-membered monocyclic heterocyclyl containing one, two or three heteroatoms selected from O, N or S; including but not limited to pyrrolidine, piperidine, piperazine, or morpholine); where the substituents are independently selected from the group consisting of halogen, hydroxyl, optionally substituted $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, amino($C_1$-$C_6$ alkyl), optionally substituted $C_3$-$C_7$ cycloalkyl, optionally substituted $C_3$-$C_7$ cycloalkyl($C_1$-$C_6$ alkyl), optionally substituted $C_6$-$C_{10}$ aryl, optionally substituted $C_6$-$C_{10}$ aryl($C_1$-$C_6$ alkyl), optionally substituted 5 to 10 membered heteroaryl, optionally substituted 5 to 10 membered heteroaryl($C_1$-$C_6$ alkyl), optionally substituted heterocyclyl, and optionally substituted heterocyclyl($C_1$-$C_6$ alkyl). In some further embodiments, the one or more substituents of $R^6$ is independently selected from the group consisting of halogen, hydroxyl, optionally substituted $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, amino($C_1$-$C_6$ alkyl), —C(=O)$NR^{16a}R^{16b}$, $C_3$-$C_7$ cycloalkyl optionally substituted with one or more $R^9$, $C_3$-$C_7$ cycloalkyl($C_1$-$C_6$ alkyl) optionally substituted with one or more $R^9$, $C_6$-$C_{10}$ aryl optionally substituted with one or more $R^9$, $C_6$-$C_{10}$ aryl($C_1$-$C_6$ alkyl) optionally substituted with one or more $R^9$, 5 or 6 membered heteroaryl optionally substituted with one or more $R^9$, 5 or 6 membered heteroaryl($C_1$-$C_6$ alkyl) optionally substituted with one or more $R^9$, heterocyclyl optionally substituted with one or more $R^9$, and heterocyclyl($C_1$-$C_6$ alkyl) optionally substituted with one or more $R^9$; wherein each $R^9$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^9$ form oxo (=O). In some embodiments, $R^6$ is unsubstituted. In other embodiments, $R^6$ is substituted with one, two or three substituents described herein. Non-limiting embodiments of the heterocyclyl and heterocyclyl($C_1$-$C_6$ alkyl) substituents include

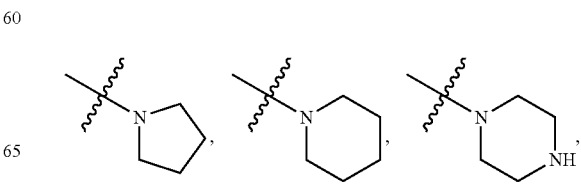

-continued

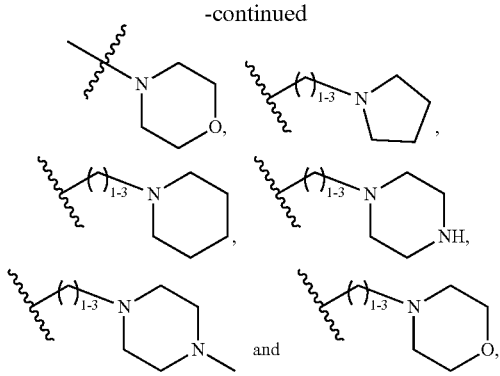

each optionally substituted with one or more $R^9$. Non-limiting embodiments of the $C_3$-$C_7$ cycloalkyl and $C_3$-$C_7$ cycloalkyl($C_1$-$C_6$ alkyl) substituents include

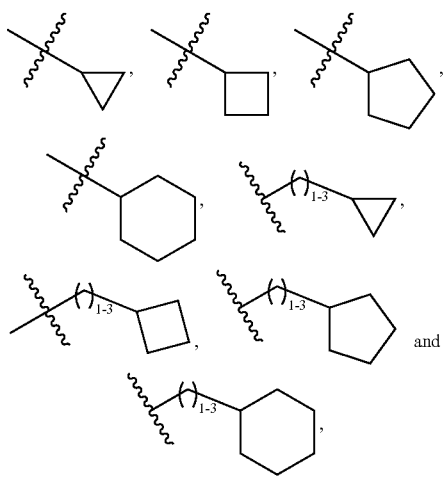

each optionally substituted with one or more $R^9$. Non-limiting embodiments of $C_6$-$C_{10}$ aryl and $C_6$-$C_{10}$ aryl($C_1$-$C_6$ alkyl) substituents include phenyl and benzyl, each optionally substituted with one or more $R^9$. Non-limiting embodiments of 5 or 6 heteroaryl and 5 or 6 heteroaryl ($C_1$-$C_6$ alkyl) substituents include pyridyl, pyrimidyl, thienyl, furyl, pyrrolyl, pyrazolyl, imidazolyl, thiazolyl, isothiazolyl, diathiazolyl, oxazolyl, isoxazolyl, —$(CH_2)_{1-3}$-pyridyl, —$(CH_2)_{1-3}$-pyrimidyl, —$(CH_2)_{1-3}$-thienyl, —$(CH_2)_{1-3}$-furyl, —$(CH_2)_{1-3}$-pyrrolyl, —$(CH_2)_{1-3}$-pyrazolyl, —$(CH_2)_{1-3}$-imidazolyl, —$(CH_2)_{1-3}$-thiazolyl, —$(CH_2)_{1-3}$-isothiazolyl, —$(CH_2)_{1-3}$-diathiazolyl, —$(CH_2)_{1-3}$-oxazolyl, and —$(CH_2)_{1-3}$-isoxazolyl, each optionally substituted with one or more $R^9$. In some further embodiments, $R^9$ is halogen, $C_1$-$C_6$ alkyl, or $C_1$-$C_6$ haloalkyl (e.g., trifluoromethyl).

In some further embodiments, $R^6$ is phenyl substituted with one, two or three $R^7$, where each $R^7$ is independently halogen, $C_1$-$C_6$ alkyl, $C_1$-$C_6$ haloalkyl, $C_1$-$C_6$ alkylamino, amino($C_1$-$C_6$ alkyl), heterocyclyl optionally substituted with one or more $R^9$ (e.g., optionally substituted with $C_1$-$C_6$ alkyl or halogen), or heterocyclyl($C_1$-$C_6$ alkyl) optionally substituted with one or more $R^9$ (e.g., optionally substituted with $C_1$-$C_6$ alkyl or halogen). In some embodiments, $R^7$ is halogen, $C_1$-$C_6$ alkyl, $C_1$-$C_6$ haloalkyl, $C_1$-$C_6$ alkylamino, unsubstituted heterocyclyl, heterocyclyl substituted with $C_1$-$C_6$ alkyl, unsubstituted heterocyclyl($C_1$-$C_6$ alkyl), or heterocyclyl($C_1$-$C_6$ alkyl) substituted with $C_1$-$C_6$ alkyl. In some such embodiments, $R^7$ is halogen (e.g., fluoro or chloro). In some such embodiments, $R^7$ is $C_1$-$C_6$ alkyl (e.g., methyl, ethyl, n-propyl, isopropyl, or t-butyl). In some such embodiments, $R^7$ is $C_1$-$C_6$ haloalkyl (such as —$CH_2F$, —$CHF_2$, —$CF_3$, —$CH_2CF_3$, and —$CF_2C_1$). In some such embodiments, $R^7$ is $C_1$-$C_6$ alkylamino (e.g., —$NH(C_1$-$C_4$ alkyl), —$N(C_1$-$C_4$ alkyl)$_2$, methylamino, dimethylamino, ethylamino, diethylamino, n-propylamino, di-n-propylamino, isopropylamino, diisopropylamino, methylethylamino, or methylisopropylamino). In some such embodiments, $R^7$ is optionally substituted amino($C_1$-$C_6$ alkyl) (e.g., —$(CH_2)_{1-3}$—$NH(C_1$-$C_4$ alkyl) or —$(CH_2)_{1-3}$—$N(C_1$-$C_4$ alkyl)$_2$). In some such embodiments, $R^7$ is a heterocyclyl optionally substituted with one or more $R^9$ (e.g., a four, five or six-membered monocyclic heterocyclyl group containing one or two heteroatoms (e.g., N, O or S), optionally substituted with one or more $R^9$). In some further embodiments, the heterocyclyl a 5 or 6 membered monocyclic heterocyclyl group, such as pyrrolidine, piperidine, piperazine, or morpholine, for example,

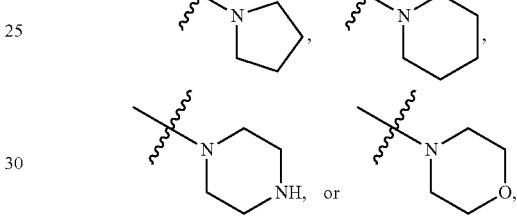

each optionally substituted with one or two $R^9$ (such as methyl, ethyl, isopropyl or t-butyl). In some further embodiments, $R^7$ is heterocyclyl($C_1$-$C_6$ alkyl) optionally substituted with one or more $R^9$ (e.g., the heterocyclyl portion may be a four, five or six-membered monocyclic heterocyclyl group containing one or two heteroatoms (e.g., N, O, or S), optionally substituted with one or more $R^9$). Non-limiting examples includes

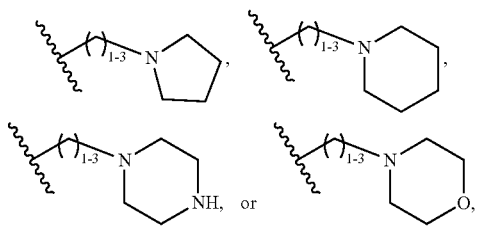

each optionally substituted with one or two $R^9$ (such as methyl, ethyl, isopropyl or t-butyl). When heterocyclyl or the heterocyclyl portion of heterocyclyl($C_1$-$C_6$ alkyl) contains a secondary amine moiety, the nitrogen atom of such amine moiety may be substituted with $R^9$ (e.g.,

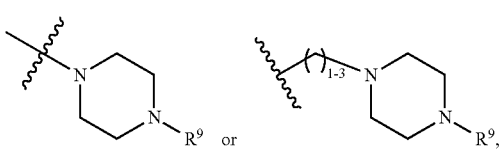

where $R^9$ is $C_1$-$C_6$ alkyl such as methyl, ethyl, isopropyl or t-butyl). In some other embodiments, $R^7$ is an unsubstituted heterocyclyl or heterocyclyl($C_1$-$C_6$ alkyl) described herein. In some embodiments, $R^6$ is a phenyl substituted with $C_3$-$C_7$ cycloalkyl or $C_3$-$C_7$ cycloalkyl($C_1$-$C_6$ alkyl). Non-limiting examples include

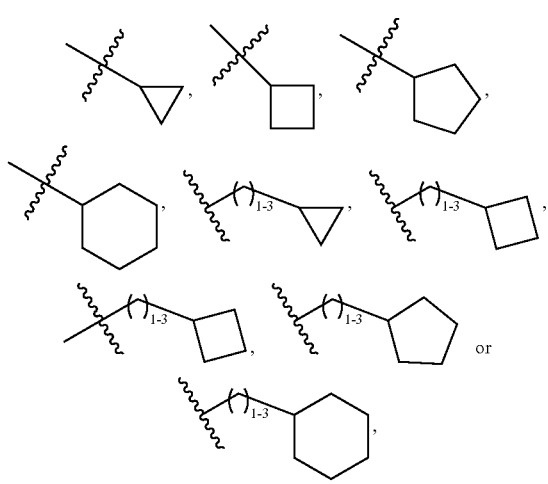

each optionally substituted with one or more $R^9$ (where $R^9$ is halogen, $C_1$-$C_6$ alkyl, or $C_1$-$C_6$ haloalkyl (e.g., trifluoromethyl)). In some further embodiments, $R^6$ is a phenyl substituted with one, two, or three substituents independently selected from the group consisting of fluoro, chloro, methyl, ethyl, n-propyl, isopropyl, t-butyl, trifluoromethyl, —NH(Me), —NH(Et), —N(Me)$_2$, —N(Et)$_2$,

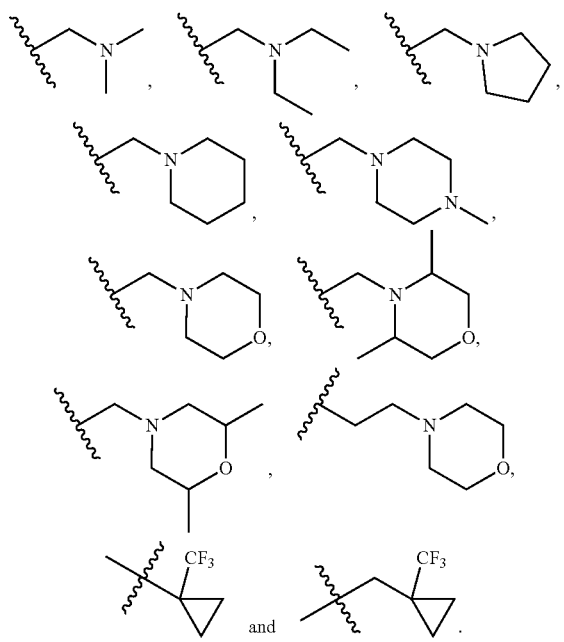

In some further embodiments, $R^6$ is substituted with one or two substituents described herein. When $R^6$ is substituted with one substituent, such substituent may be at the para position

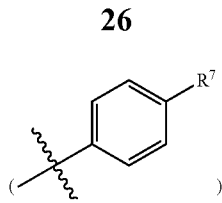

or meta position

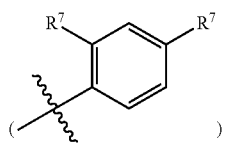

When $R^6$ is substituted with two substituents, such substituents may be at the para and otho positions

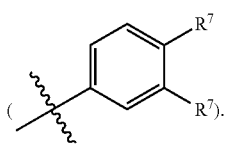

or at the para and meta positions

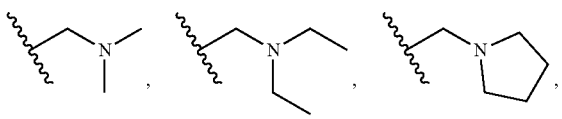

In some other embodiments, $R^6$ is naphthyl substituted with one, two or three $R^8$, where each $R^8$ is independently halogen, $C_1$-$C_6$ alkyl, $C_1$-$C_6$ haloalkyl, $C_1$-$C_6$ alkylamino, amino($C_1$-$C_6$ alkyl), $C_3$-$C_7$ cycloalkyl optionally substituted with one or more $R^9$, $C_3$-$C_7$ cycloalkyl($C_1$-$C_6$ alkyl) optionally substituted with one or more $R^9$, heterocyclyl optionally substituted with one or more $R^9$ (e.g., optionally substituted with $C_1$-$C_6$ alkyl or halogen), or heterocyclyl($C_1$-$C_6$ alkyl) optionally substituted with one or more $R^9$ (e.g., optionally substituted with $C_1$-$C_6$ alkyl or halogen). In some further embodiments, In some embodiments, $R^7$ is halogen, $C_1$-$C_6$ alkyl, $C_1$-$C_6$ haloalkyl, $C_1$-$C_6$ alkylamino, unsubstituted heterocyclyl, heterocyclyl substituted with $C_1$-$C_6$ alkyl, unsubstituted heterocyclyl($C_1$-$C_6$ alkyl), or heterocyclyl($C_1$-$C_6$ alkyl) substituted with $C_1$-$C_6$ alkyl. In some further embodiments, $R^6$ is substituted with one, two, or three substituents independently selected from the group consisting of fluoro, chloro, methyl, ethyl, n-propyl, isopropyl, t-butyl, trifluoromethyl, —NH(Me), —NH(Et), —N(Me)$_2$, —N(Et)$_2$, -continued

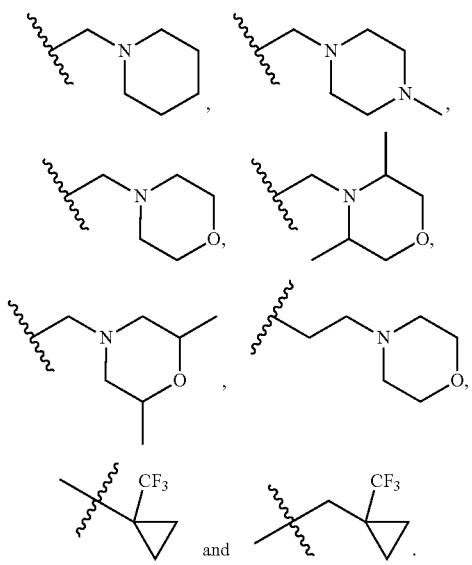

In some other embodiments, R⁶ is a pyridyl substituted with one, two, or three substituents independently selected from the group consisting of halogen, $C_1$-$C_6$ alkyl, $C_1$-$C_6$ haloalkyl, $C_1$-$C_6$ alkylamino, amino($C_1$-$C_6$ alkyl), $C_3$-$C_7$ cycloalkyl optionally substituted with one or more $R^9$, $C_3$-$C_7$ cycloalkyl($C_1$-$C_6$ alkyl) optionally substituted with one or more $R^9$, 5 or 6 membered heterocyclyl optionally substituted with one or more $R^9$, and 5 or 6 membered heterocyclyl($C_1$-$C_6$ alkyl) optionally substituted with one or more $R^9$. In some further embodiments, $R^6$ is a pyridyl substituted with one, two, or three substituents independently selected from the group consisting of fluoro, chloro, methyl, ethyl, n-propyl, isopropyl, t-butyl, trifluoromethyl, —NH(Me), —NH(Et), —N(Me)₂, —N(Et)₂,

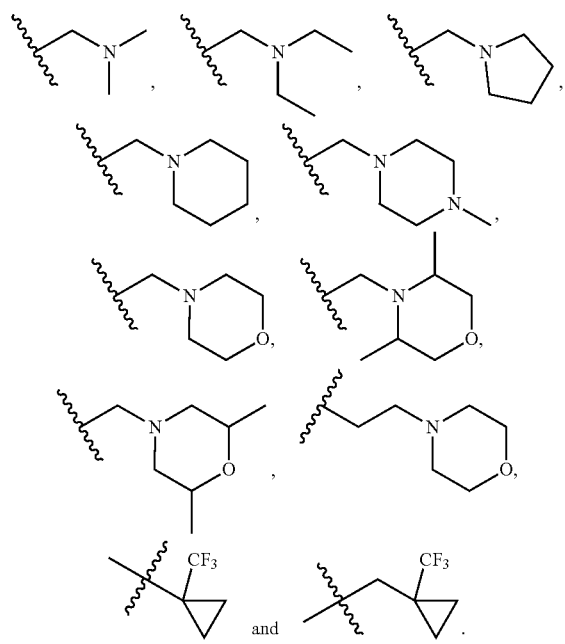

In some embodiments, the compound of Formula (I) is:

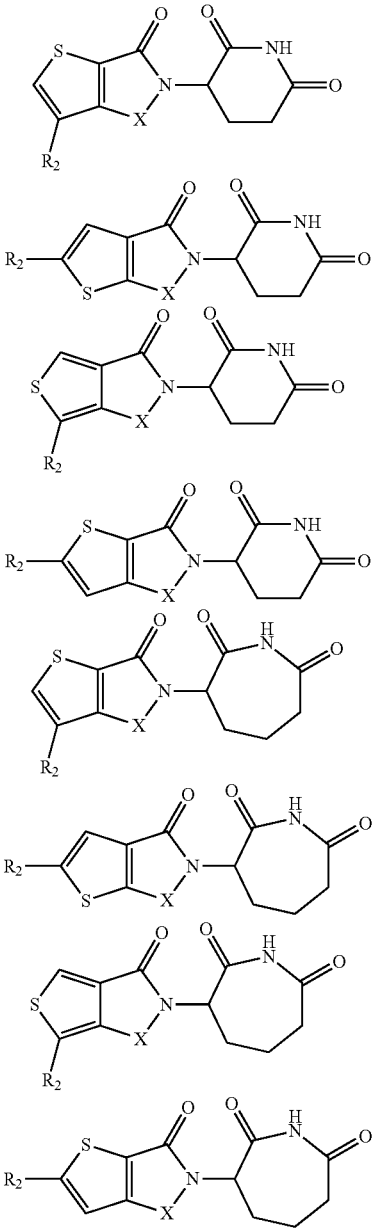

or a pharmaceutically acceptable salt of any of the foregoing. In some embodiments, X is C=O or CH₂. In some embodiments, X is C=O. In other embodiments, X is CH₂. In some embodiments, one of $X_A$ and $X_C$ is a bond. In other embodiments, both $X_A$ and $X_C$ are —CH₂—. In some such embodiments, $R^2$ is —CH₂—CH₂—$R^6$. In some such embodiments, $R^2$ is —O—CH₂—$R^6$. In other embodiments, $R^2$ is —S—CH₂—$R^6$. In still other embodiments, $R^2$ is —NH—CH₂—$R^6$. In some such embodiments, $R^2$ is —CH₂—O—$R^6$. In other embodiments, $R^2$ is —CH₂—S—$R^6$. In still other embodiments, $R^2$ is —CH₂—NH—$R^6$. In some such embodiments, $R^2$ is —CH₂—O—CH₂—$R^6$. In other embodiments, $R^2$ is —CH₂—S—CH₂—$R^6$. In still other embodiments, $R^2$ is —CH₂—NH—CH₂—$R^6$. In some embodiments, $R^6$ is phenyl substituted with one or two substituents. In some such embodiments, when $R^6$ is phenyl substituted with one substituent, such substituent is fluoro, chloro, methyl, ethyl, isopropyl or t-butyl. In some such embodiments, when R⁶ is phenyl substituted with one substituent, such substituent is —N(Me)$_2$, —N(Et)$_2$, —(CH$_2$)$_{1-2}$—N(Me)$_2$, or —(CH$_2$)$_{12}$N(Et)$_2$. In some such embodiments, when R⁶ is phenyl substituted with one substituent, such substituent is

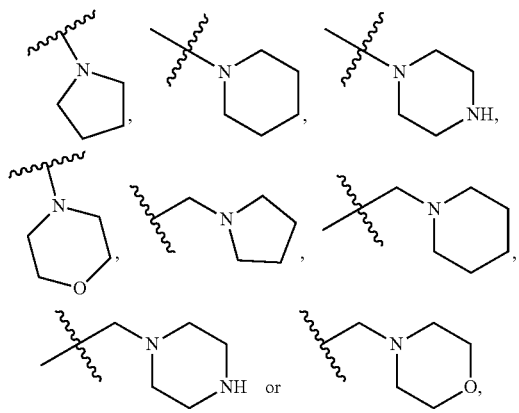

each optionally substituted with one or more R⁹, for example, C$_1$-C$_6$ alkyl. In some such embodiments, when R⁶ is phenyl substituted with one substituent, such substituent is

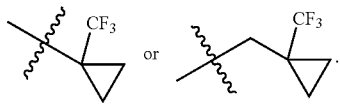 [SMILES: *C1(C(F)(F)F)CC1 ; *CC1(C(F)(F)F)CC1]

In some such embodiments, when R⁶ is phenyl substituted with two substituents, such substituents are independently fluoro, chloro, methyl, trifluoromethyl, ethyl, isopropyl or t-butyl. In some such embodiments, when R⁶ is phenyl substituted with two substituents, one such substituent is —N(Me)$_2$, —N(Et)$_2$, —(CH$_2$)$_{1-2}$—N(Me)$_2$, or —(CH$_2$)$_{1-2}$N(Et)$_2$; and the other such substituent is fluoro, chloro, methyl, trifluoromethyl, ethyl, isopropyl or t-butyl. In some such embodiments, when R⁶ is phenyl substituted with two substituents, one such substituent is

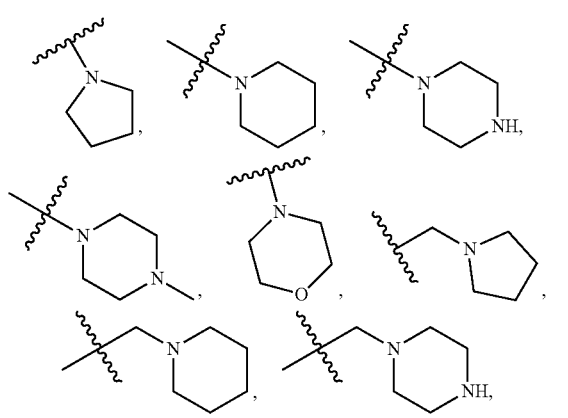

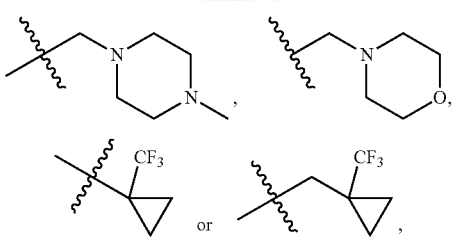

each optionally substituted with one or more R⁹ (for example, C$_1$-C$_6$ alkyl); and the other such substituent is fluoro, chloro, methyl, trifluoromethyl, ethyl, isopropyl, t-butyl, —N(Me)$_2$, —N(Et)$_2$, —(CH$_2$)$_{1-2}$—N(Me)$_2$, or —(CH$_2$)$_{1-2}$N(Et)$_2$.

In some embodiments, the compound of Formula (I) is selected from Compounds 1-31 of Table B, and pharmaceutically acceptable salts thereof.

TABLE B

Exemplary Compounds of Formula (I)

| COMPD No. | Structure |
|---|---|
| 1 | 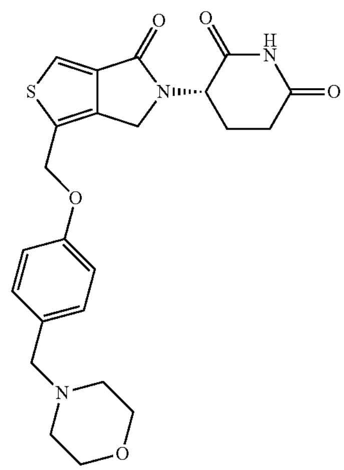 [SMILES: O=C1CC[C@H](N2Cc3c(csc3COc3ccc(CN4CCOCC4)cc3)C2=O)C(=O)N1] |
| 2 | 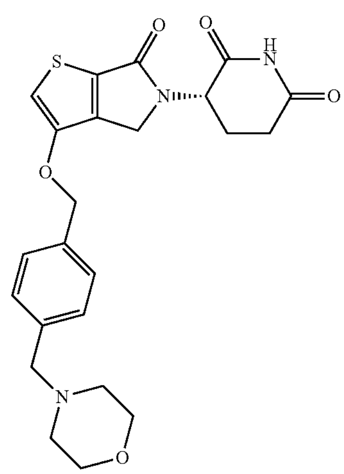 [SMILES: O=C1CC[C@H](N2Cc3c(OCc4ccc(CN5CCOCC5)cc4)csc3C2=O)C(=O)N1] |

TABLE B-continued

Exemplary Compounds of Formula (I)

| COMPD No. | Structure |
|---|---|
| 3 | *(structure)* |
| 4 | *(structure)* |
| 5 | *(structure)* |
| 6 | *(structure)* |
| 7 | *(structure)* |
| 8 | *(structure)* |

TABLE B-continued

Exemplary Compounds of Formula (I)

| COMPD No. | Structure |
|---|---|
| 9 | 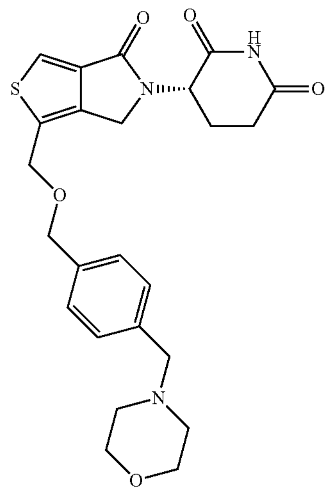 [SMILES: O=C1CC[C@H](N2Cc3c(csc3COCc3ccc(CN4CCOCC4)cc3)C2=O)C(=O)N1] |
| 10 | 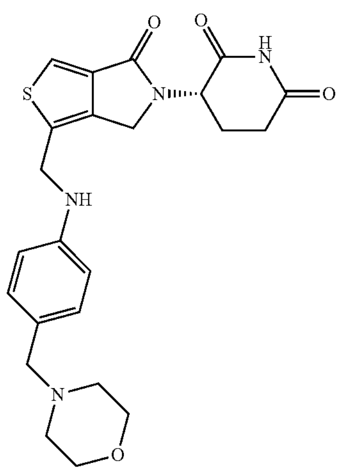 [SMILES: O=C1CC[C@H](N2Cc3c(csc3CNc3ccc(CN4CCOCC4)cc3)C2=O)C(=O)N1] |
| 11 | 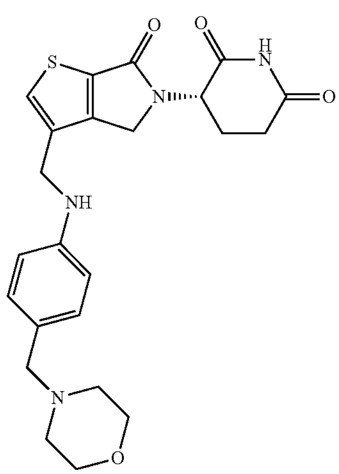 [SMILES: O=C1CC[C@H](N2Cc3c(CNc4ccc(CN5CCOCC5)cc4)csc3C2=O)C(=O)N1] |
| 12 | |
| 13 | |
| 14 | |

TABLE B-continued

Exemplary Compounds of Formula (I)

| COMPD No. | Structure |
|---|---|
| 15 | 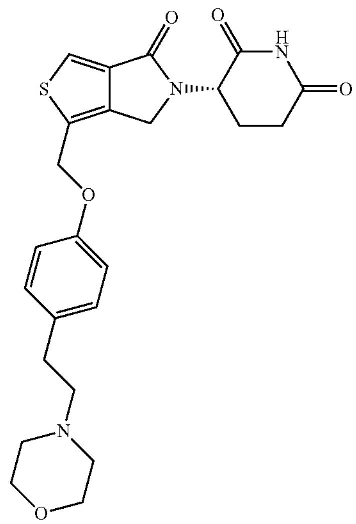 [SMILES: O=C1CC[C@H](N2Cc3c(csc3COc3ccc(CCN4CCOCC4)cc3)C2=O)C(=O)N1] |
| 16 | 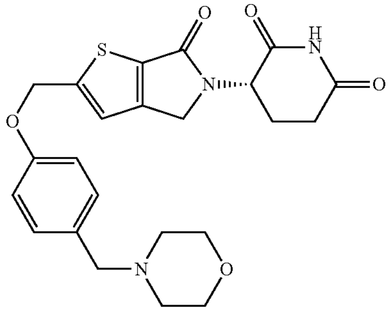 [SMILES: O=C1CC[C@H](N2Cc3cc(COc4ccc(CN5CCOCC5)cc4)sc3C2=O)C(=O)N1] |
| 17 | 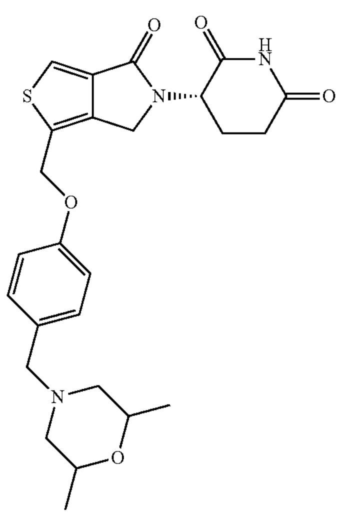 [SMILES: CC1CN(Cc2ccc(OCc3scc4c3CN([C@H]3CCC(=O)NC3=O)C4=O)cc2)CC(C)O1] |
| 18 | |
| 19 | |
| 20 | |

TABLE B-continued

Exemplary Compounds of Formula (I)

| COMPD No. | Structure |
|---|---|
| 21 | |
| 22 | |
| 23 | |
| 24 | 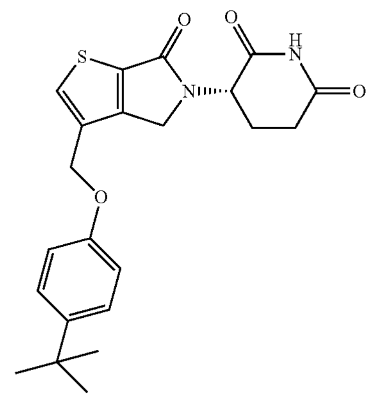 [SMILES: CC(C)(C)c1ccc(OCc2csc3c2CN([C@H]2CCC(=O)NC2=O)C3=O)cc1] |
| 25 | 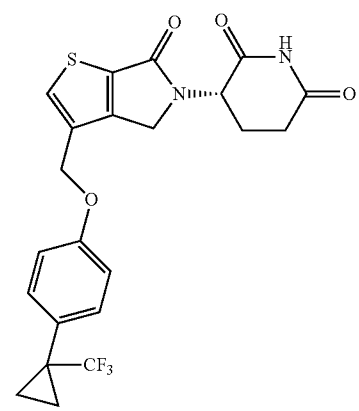 [SMILES: O=C1CC[C@H](N2Cc3c(COc4ccc(C5(C(F)(F)F)CC5)cc4)csc3C2=O)C(=O)N1] |
| 26 | 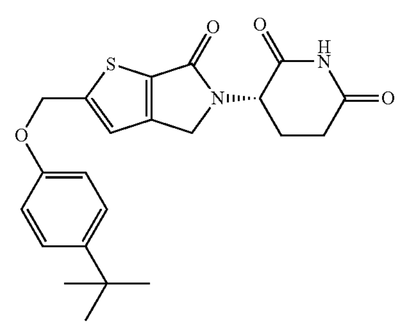 [SMILES: CC(C)(C)c1ccc(OCc2cc3c(s2)C(=O)N([C@H]2CCC(=O)NC2=O)C3)cc1] |
| 27 | 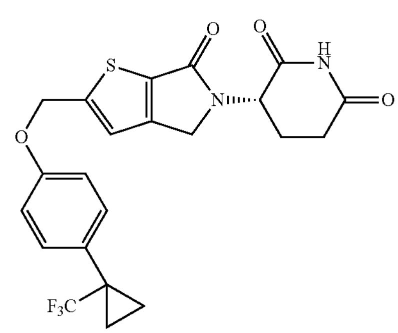 [SMILES: O=C1CC[C@H](N2Cc3cc(COc4ccc(C5(C(F)(F)F)CC5)cc4)sc3C2=O)C(=O)N1] |

TABLE B-continued

Exemplary Compounds of Formula (I)

| COMPD No. | Structure |
|---|---|
| 28 | 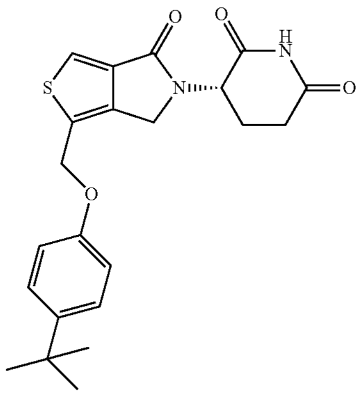 [SMILES: CC(C)(C)c1ccc(OCc2scc3c2CN([C@H]2CCC(=O)NC2=O)C3=O)cc1] |
| 29 | 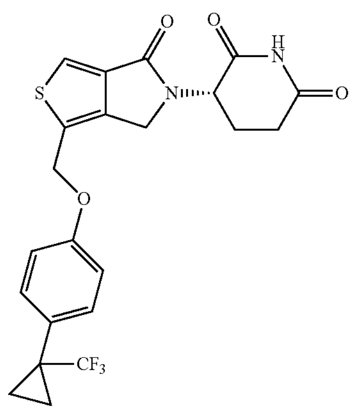 [SMILES: O=C1CC[C@H](N2Cc3c(csc3COc3ccc(C4(C(F)(F)F)CC4)cc3)C2=O)C(=O)N1] |
| 30 | 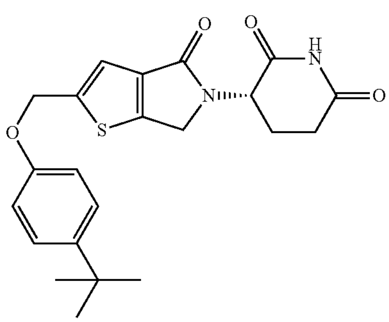 [SMILES: CC(C)(C)c1ccc(OCc2cc3c(s2)CN([C@H]2CCC(=O)NC2=O)C3=O)cc1] |
| 31 | 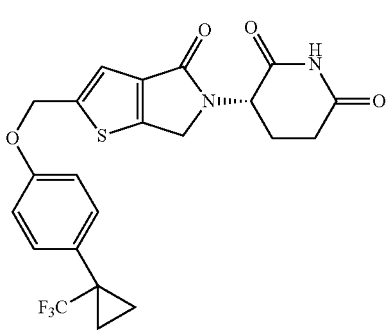 [SMILES: O=C1CC[C@H](N2Cc3sc(COc4ccc(C5(C(F)(F)F)CC5)cc4)cc3C2=O)C(=O)N1] |

Some embodiments provide a pharmaceutical composition, comprising a compound of Formula (I), (Ia), (Ib), (Ic), (Id), (Ie), or (If), or a pharmaceutically acceptable salt thereof, and at least one pharmaceutically acceptable carrier or excipient.

In any embodiments of the compounds described herein, when a substituent is selected from a carbocyclyl (e.g., $C_3$-$C_8$ carbocyclyl, it includes $C_3$-$C_8$ cycloalkyl. When a substituent is select from 3 to 7 membered heterocyclyl, it includes 3 to 7 membered monocyclic heterocycle rings with no double or triple bond within the ring structure.

In some embodiments, the compound of Formula (I) (including Formula (Ia)-(If)) is formed as a pharmaceutically acceptable salt. In some embodiments, the pharmaceutically acceptable salt is a trifluoroacetic acid salt. In some embodiments, the compound of Formula (I) (including Formula (Ia)-(If)), or a pharmaceutically acceptable salt of any of the foregoing, is racemic. In some embodiments, the compound of Formula (I) (including Formula (Ia)-(If)), or a pharmaceutically acceptable salt of any of the foregoing, has an S-configuration or a R-configuration (for example, at the carbon atom with an asterisk

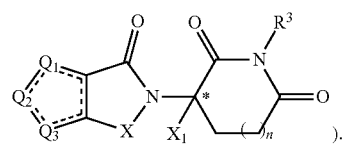

In some embodiments, the compound of Formula (I) (including Formula (Ia)-(If)), or a pharmaceutically acceptable salt of any of the foregoing, is enriched in one enantiomer over another enantiomer, for example, enriched by about 10%, 20%, 30%, 40%, 50%, 60%, 70%, 80%, 90%, 95%, or 99%, or a range defined by any two preceding values. In some embodiments, the compound of Formula (I) (including Formula (Ia)-(If) or a pharmaceutically acceptable salt of any of the foregoing, is enriched in one diastereomer over another diastereomer for example, enriched by about 10%, 20%, 30%, 40%, 50%, 60%, 70%, 80%, 90%, 95%, or 99%, or a range defined by any two preceding values. In some embodiments, the compound of Formula (I) (including Formula (Ia)-(If)) is a pharmaceutically acceptable solvate.

Methods of Treatment/Uses

Some embodiments provide a method of modulating the activity of a protein in a biological sample, comprising contacting the biological sample with a compound of Formula (I) (including (Ia), (Ib), (Ic), (Id), (Ie), or (If)), or a pharmaceutically acceptable salt thereof; wherein the protein is IL-1β, IL-2, IL-6, TNFα, CK1α, GSPT1, aiolos, ikaros, or helios, or combinations thereof. Some embodiments provide the use of a compound of Formula (I) (including (Ia), (Ib), (Ic), (Id), (Ie), or (If)), or a pharmaceutically acceptable salt thereof, for modulating the activity of a protein in a biological sample, comprising contacting the biological sample with a compound of Formula (I) (including (Ia), (Ib), (Ic), (Id), (Ie), or (If)) or a pharmaceutically acceptable salt thereof; wherein the protein is IL-1β, IL-2, IL-6, TNFα, CK1α, GSPT1, aiolos, ikaros, or helios, or combinations thereof. In some embodiments, the protein is wild-type. In other embodiments, the protein is a mutant form of the protein. In some embodiments, the protein is overexpressed. In some aspect, the method or use inhibits the activity of the protein. In another aspect, the method of use induce the activity of the protein, for example, IL-2. In some embodiments, the biological sample contains one or more cancer cells. In some embodiments, the cells are small cell lung cancer cells, non-small cell lung cancer cells, breast cancer cells, prostate cancer cells, head and neck cancer cells, pancreatic cancer cells, colon cancer cells, rectal cancer cells, teratoma cells, ovarian cancer cells, gastric cancer cells, endometrial cancer cells, brain cancer cells, retinoblastoma cells, leukemia cells, skin cancer cells, melanoma cells, squamous cell carcinoma cells, liposarcoma cells, lymphoma cells, multiple myeloma cells, testicular cancer cells, liver cancer cells, esophageal cancer cells, kidney carcinoma cells, astrogliosis cells, multiple myeloma cells (relapsed/refractory), or neuroblastoma cells. In some further embodiments, the biological sample contains leukemia cells, lymphoma cells, or multiple myeloma cells.

Some embodiments provide a method of treating, ameliorating, or preventing a disease, disorder, or condition associated with a protein in a subject, the protein is IL-1β, IL-2, IL-6, TNFα, CK1α, GSPT1, aiolos, ikaros, or helios, or combinations of any of the foregoing; the method comprising administering a therapeutically effective amount of a compound of Formula (I) (including (Ia), (Ib), (Ic), (Id), (Ie), or (If)), or a pharmaceutically acceptable salt thereof, or a pharmaceutical composition thereof to the subject; wherein the disease, disorder, or condition is a hematological malignancy or a solid tumor. Some embodiments provide the use of a compound of Formula (I) (including (Ia), (Ib), (Ic), (Id), (Ie), or (If)), or a pharmaceutically acceptable salt thereof, or a pharmaceutical composition thereof for treating, ameliorating, or preventing a disease, disorder, or condition associated with a protein; wherein the protein is IL-1β, IL-2, IL-6, TNFα, CK1α, GSPT1, aiolos, ikaros, or helios, combinations of any of the foregoing; and wherein the disease, disorder, or condition is a hematological malignancy or a solid tumor. In some embodiments, the protein is wild-type. In other embodiments, the protein is a mutant form of the protein. In some embodiments, the protein is overexpressed.

Some other embodiments provide a method of treating, ameliorating, or preventing a hematological malignancy or a solid tumor in a subject, comprising administering a therapeutically effective amount of a compound of Formula (I) (including (Ia), (Ib), (Ic), (Id), (Ie), or (If)), or a pharmaceutically acceptable salt thereof, or a pharmaceutical composition thereof to the subject. Some embodiments provide the use of a compound of Formula (I) (including (Ia), (Ib), (Ic), (Id), (Ie), or (If)), or a pharmaceutically acceptable salt thereof, or a pharmaceutical composition thereof for treating, ameliorating, or preventing a hematological malignancy or a solid tumor. In some embodiments, the hematological malignancy or the solid tumor is associated with a protein, wherein the protein is IL-1β, IL-2, IL-6, TNFα, CK1α, GSPT1, aiolos, ikaros, or helios, combinations of any of the foregoing. In some embodiments, the protein is wild-type. In other embodiments, the protein is a mutant form of the protein. In some embodiments, the protein is overexpressed.

In some embodiments of the methods or uses described herein, the hematological malignancy or a solid tumor is small cell lung cancer, non-small cell lung cancer, breast cancer, prostate cancer, head and neck cancer, pancreatic cancer, colon cancer, rectal cancer, teratoma, ovarian cancer, gastric cancer, endometrial cancer, brain cancer, retinoblastoma, leukemia, skin cancer, melanoma, squamous cell carcinoma, liposarcoma, lymphoma, multiple myeloma, testicular cancer, liver cancer, esophageal cancer, kidney carcinoma, astrogliosis, multiple myeloma (relapsed/refractory), or neuroblastoma. In some further embodiments, the hematological malignancy is leukemia, lymphoma, or multiple myeloma.

Some additional embodiments provide a method of treating, ameliorating, or preventing a disease, disorder, or condition associated with a protein in a subject, the protein is IL-1β, IL-2, IL-6, TNFα, CK1α, GSPT1, aiolos, ikaros, or helios, or combinations of any of the foregoing; the method comprising administering a therapeutically effective amount of a compound of Formula (I) (including (Ia), (Ib), (Ic), (Id), (Ie), or (If)), or a pharmaceutically acceptable salt thereof, or a pharmaceutical composition thereof to the subject; wherein the disease, disorder, or condition is a neurodegenerative disease, fibrosis, lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, or chronic obstructive pulmonary disease. In some further embodiments, the neurodegenerative disease may include multiple sclerosis, Alzheimer's disease, Parkinson's disease and other chronic inflammatory diseases of the central nervous system. In some further embodiments, fibrosis may include renal fibrosis, pulmonary fibrosis, and hepatic fibrosis. Some embodiments provide the use of a compound of Formula (I) (including (Ia), (Ib), (Ic), (Id), (Ie), or (If)), or a pharmaceutically acceptable salt thereof, or a pharmaceutical composition thereof for treating, ameliorating, or preventing a disease, disorder, or condition associated with a protein; wherein the protein is IL-1β, IL-2, IL-6, TNFα, CK1α, GSPT1, aiolos, ikaros, or helios, or combinations of any of the foregoing; and wherein the disease, disorder, or condition is a neurodegenerative disease, fibrosis, lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, or chronic obstructive pulmonary disease. In some embodiments, the disease, disorder, or condition is multiple sclerosis, Alzheimer's disease, Parkinson's disease, lupus, fibromyalgia, rheumatoid arthritis, osteoarthritis, ankylosing spondylitis, psoriasis, psoriatic arthritis, Crohn's disease, or ulcerative colitis. In some embodiments, the protein is wild-type. In other embodiments, the protein is a mutant form of the protein. In some embodiments, the protein is overexpressed.

Some embodiments provide a method of treating, ameliorating, or preventing an inflammatory disease, disorder or condition in a subject, comprising administering a therapeutically effective amount of a compound of Formula (I) (including (Ia), (Ib), (Ic), (Id), (Ie), or (If)), or a pharmaceutically acceptable salt thereof, or a pharmaceutical composition thereof to the subject. Some embodiments provide the use of a compound of Formula (I) (including (Ia), (Ib), (Ic), (Id), (Ie), or (If)), or a pharmaceutically acceptable salt thereof, or a pharmaceutical composition thereof for treating, ameliorating, or preventing an inflammatory disease, disorder or condition. In some embodiments, the inflammatory disease, disorder or condition is a neurodegenerative disease (such as multiple sclerosis, Alzheimer's disease, Parkinson's disease), pulmonary fibrosis, lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, or chronic obstructive pulmonary disease. In some embodiments, the inflammatory disease, disorder or condition is associated with a protein, wherein the protein is IL-1β, IL-2, IL-6, TNFα, CK1α, GSPT1, aiolos, ikaros, or helios, combinations of any of the foregoing. In some embodiments, the protein is wild-type. In other embodiments, the protein is a mutant form of the protein. In some embodiments, the protein is overexpressed.

Additional Therapeutic Agents

Some embodiments provide pharmaceutical compositions comprising a compound of Formula (I) (including (Ia), (Ib), (Ic), (Id), (Ie), or (If)) or a pharmaceutically acceptable salt of any of the foregoing and a second therapeutic agent. In some embodiments, the second therapeutic agent is an anti-inflammatory agent. In some embodiments, the second therapeutic agent is a non-steroidal anti-inflammatory agent. In some embodiments, the second therapeutic agent is an anti-cancer agent. In some embodiments, the second therapeutic agent is an immunostimulatory agent. In some embodiments, the second therapeutic agent is an immunosuppressive agent. In some embodiments, the second therapeutic agent is an antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone. In some embodiments, the second therapeutic agent is mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; or oxaliplatin. In some embodiments, the second therapeutic agent is vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; or teniposide. In some embodiments, the second therapeutic agent is actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; or procarbazine. In some embodiments, the second therapeutic agent is cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; or floxuridine. In some embodiments, the second therapeutic agent is azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; or triethylenemelamine. In some embodiments, the second therapeutic agent is nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; or eribulin. In some embodiments, the second therapeutic agent is azathioprine; mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; or ocrelizumab. In some embodiments, the second therapeutic agent is pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; rovelizumab; siplizumab; talizumab; telimomab; vapaliximab; vepalimomab; abatacept; belatacept; pegsunercept; aflibercept; alefacept; or rilonacept.

Dosing Regimes

In some embodiments, about 1 mg to about 5 grams, or any amount in between, of a compound of Formula (I) (including (Ia), (Ib), (Ic), (Id), (Ie), or (If)), or a pharmaceutically acceptable salt of any of the foregoing is administered each day, each week, or each cycle of treatment.

In some embodiments, a compound of Formula (I) (including (Ia), (Ib), (Ic), (Id), (Ie), or (If)), or a pharmaceutically acceptable salt of any of the foregoing is administered once per day, twice per day, three times per day, four times per day, or more than four times per day. In some embodiments, a compound of Formula (I) (including (Ia), (Ib), (Ic), (Id), (Ie), or (If)), or a pharmaceutically acceptable salt of any of the foregoing is administered once per day, twice per day, three times per day, four times per day, or more than four times per cycle of treatment.

In some embodiments, each cycle of treatment lasts from 1 day to 14 days, or any value in between. In some embodiments, each cycle of treatment has from at least one day up to fourteen days, or any value in between, between administration. In some embodiments, each cycle of treatment includes one or more additional therapeutic agents, as described herein. In some embodiments, a compound of Formula (I) (including (Ia), (Ib), (Ic), (Id), (Ie), or (If)), or a pharmaceutically acceptable salt of any of the foregoing is provided intravenously over about 10 minutes to over about 4 hours, or any value in between.

Pharmaceutical Compositions

Some embodiments described herein relate to a pharmaceutical composition, that can include an effective amount of one or more compounds described herein (for example, a compound of Formula (I) (including (Ia), (Ib), (Ic), (Id), (Ie), or (If)), or a pharmaceutically acceptable salt thereof) and at least one pharmaceutically acceptable excipient or carrier.

The term "pharmaceutical composition" refers to a mixture of one or more compounds and/or salts disclosed herein with other chemical components, such as one or more excipients. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

As used herein, an "excipient" refers to essentially inert substances that are added to a pharmaceutical composition to provide, without limitation, bulk, consistency, stability, binding ability, lubrication, disintegrating ability etc., to the composition. For example, stabilizers such as anti-oxidants and metal-chelating agents are excipients. Excipients also include ingredients in a pharmaceutical composition that lack appreciable pharmacological activity but may be pharmaceutically necessary or desirable. For example, to increase the bulk of a potent drug whose mass is too small for manufacture and/or administration. It may also be a liquid for the dissolution of a drug to be administered by injection, ingestion or inhalation. For example, a buffered aqueous solution such as, without limitation, phosphate buffered saline that mimics the pH and isotonicity of human blood.

The pharmaceutical compositions described herein can be administered to a human patient per se, or in pharmaceutical compositions where they are mixed with other active ingredients, as in combination therapy, or excipients, or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

One or more of the compounds of preferred embodiments can be provided in the form of pharmaceutically acceptable salts, active metabolites, tautomers, or prodrugs thereof. Some embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound of Formula (I), or a pharmaceutically acceptable salt thereof, can be administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical excipient may also be prepared, placed in an appropriate container, and labeled for treatment of an indicated condition.

EXAMPLES

Additional embodiments are disclosed in further detail in the following schemes, which are not in any way intended to limit the scope of the claims.

Characterization of the compounds disclosed herein is performed with Bruker AV-500 and Bruker DRX-500 NMR spectrometers and a Perkin Elmer PE-SCIEX API-150 mass spectrometer.

General Synthesis

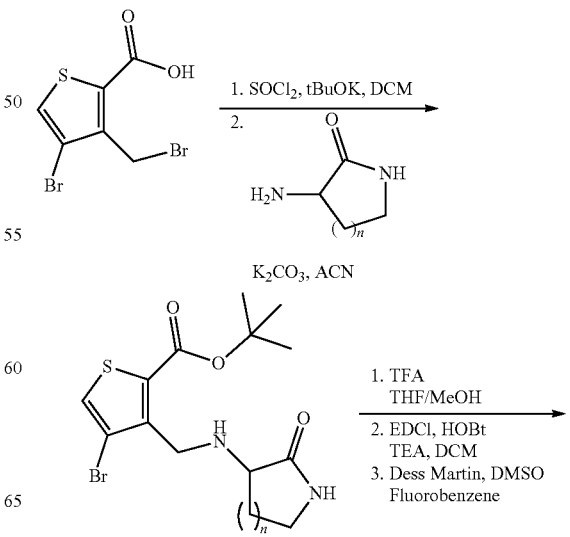

Scheme 1

-continued

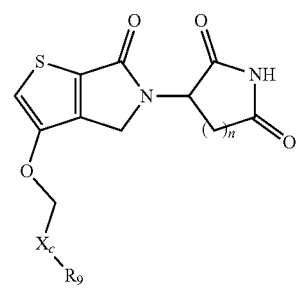

Scheme 2

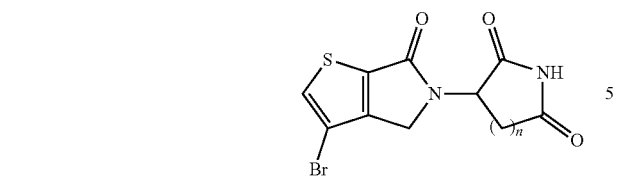
1. Ph₂C=NH₂, Xanphos, Pd₂(dbu)₃, Cs₂CO₃ Dioxane, Toluene
2. NH₄OH, HCl, NaOAc, DCM/MeOH

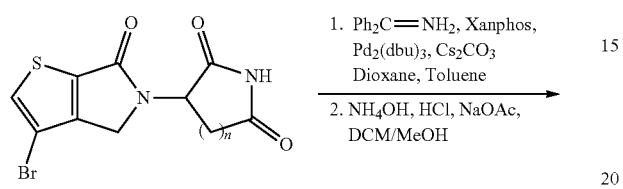
$\xrightarrow{\text{NaBH}_3\text{CN, THF}}$
H-C(=O)-X$_c$-R₉

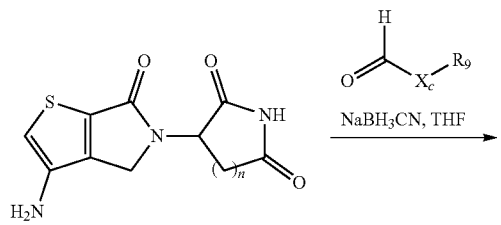

Scheme 3

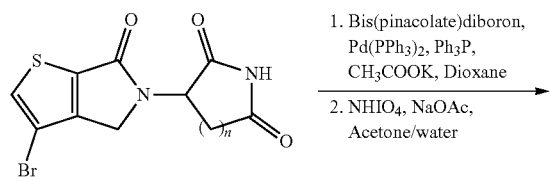
1. Bis(pinacolate)diboron, Pd(PPh₃)₂, Ph₃P, CH₃COOK, Dioxane
2. NHIO₄, NaOAc, Acetone/water

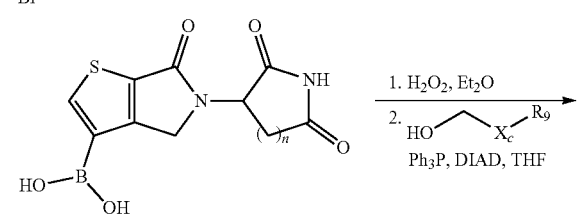
1. H₂O₂, Et₂O
2. HO-X$_c$-R₉, Ph₃P, DIAD, THF

Scheme 4

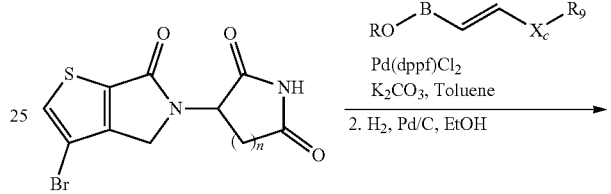
1. (RO)₂B-CH=CH-X$_c$-R₉, Pd(dppf)Cl₂, K₂CO₃, Toluene
2. H₂, Pd/C, EtOH

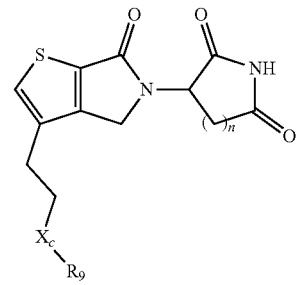

Scheme 5

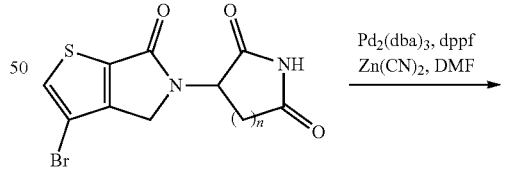
Pd₂(dba)₃, dppf, Zn(CN)₂, DMF

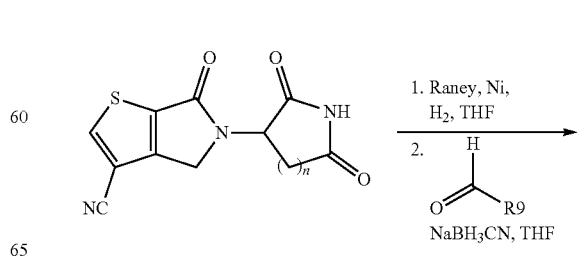
1. Raney, Ni, H₂, THF
2. H-C(=O)-R9, NaBH₃CN, THF

49

-continued

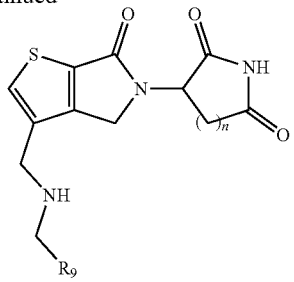

Scheme 6

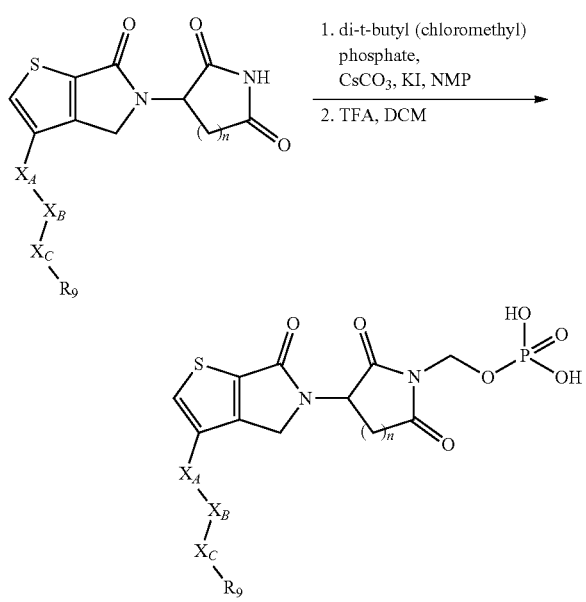

Example 1

Compound 1: (S)-3-(1-((4-(morpholinomethyl)phenoxy)methyl)-4-oxo-4H-thieno[3,4-c]pyrrol-5(6H)-yl)piperidine-2,6-dione

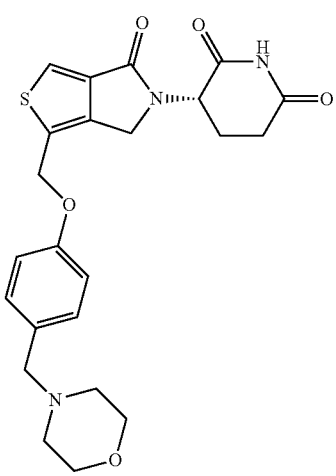 [SMILES: O=C1CC[C@H](N2Cc3c(csc3COc3ccc(CN4CCOCC4)cc3)C2=O)C(=O)N1]

50

To a solution of methyl 4-methylthiophene-3-carboxylate (5.0 g, 32 mmol) in DMF (25 mL) at 0° C. was added NBS (6.0 g, 34 mmol). The mixture was stirred at RT overnight then poured into water and extracted with EA. The combined organic layers were washed with brine, dried over $Na_2SO_4$, filtered, and concentrated to give methyl 5-bromo-4-methylthiophene-3-carboxylate (7.2 g, crude) as an oil. $^1$H NMR (300 MHz, $CDCl_3$) δ 8.06 (s, 1H), 3.86 (s, 3H), 2.42 (s, 3H).

To a solution of methyl 5-bromo-4-methylthiophene-3-carboxylate (7.2 g, 30 mmol, crude) in $CCl_4$ (70 mL) was added NBS (5.75 g, 32.3 mmol) and benzoyl peroxide (2.18 g, 9.00 mmol). After heating at 80° C. for 5 h, the mixture was filtered, and the filtrate was concentrated. The residue was purified using silica gel eluting with PE/EA (1:1) to give methyl 5-bromo-4-(bromomethyl)thiophene-3-carboxylate (4.4 g, 46% yield) as an oil. $^1$H NMR (300 MHz, $CDCl_3$) δ 8.04 (s, 1H), 4.77 (s, 2H), 3.83 (s, 3H).

To a solution of methyl 5-bromo-4-(bromomethyl)thiophene-3-carboxylate (4.4 g, 1.0 mmol) and (S)-tert-butyl 4,5-diamino-5-oxopentanoate (4.00 g, 16.9 mmol) in DMF (40 mL) was added TEA (4 mL). The mixture was stirred at 40° C. for 3 h then quenched with water and extracted with DCM. The combined organic layers were washed with aqueous 1M LiCl, and brine, then dried over $Na_2SO_4$, filtered, and concentrated to give (S)-methyl 4-(((1-amino-5-(tert-butoxy)-1,5-dioxopentan-2-yl)amino)methyl)-5-bromothiophene-3-carboxylate (5.70 g, 93% yield) as an oil. MS (ESI) m/z 435.1 [M+H]+.

To a solution of (S)-methyl 4-(((1-amino-5-(tert-butoxy)-1,5-dioxopentan-2-yl)amino)methyl)-5-bromothiophene-3-carboxylate (5.70 g, 13.1 mmol) in THF (80 mL) at 0° C. was added aqueous 0.6 M LiOH (33 mL). The mixture was stirred at 0° C. for 2 h then concentrated. The residue was dissolved in water and washed with EA. The aqueous layer was adjusted to a pH of 6 using 1N HCl. The resulting precipitate was collected by filtration to give (S)-4-(((1-amino-5-(tert-butoxy)-1,5-dioxopentan-2-yl)amino) methyl)-5-bromothiophene-3-carboxylic acid (2.2 g, 40% yield) as a solid. MS (ESI) m/z 421.1 [M+H]$^+$.

To a mixture of (S)-4-(((1-amino-5-(tert-butoxy)-1,5-dioxopentan-2-yl)amino)methyl)-5-bromothiophene-3-carboxylic acid (2.2 g, 5.2 mmol) in DMF was added 2-(7-aza-1H-benzotriazole-1-yl)-1,1,3,3-tetramethyluronium hexafluorophosphate (4.00 g, 10.4 mmol) and DIEA (2.6 mL). After 2 h, the mixture was quenched with water and extracted with EA. The combined organic layers were washed with 1M aqueous LiCl, saturated $NaHCO_3$, and brine, then dried over $Na_2SO_4$, filtered, and concentrated. The residue was purified using silica gel eluting with PE/EA (1:2) to give (S)-tert-butyl 5-amino-4-(1-bromo-4-oxo-4H-thieno[3,4-c]pyrrol-5(6H)-yl)-5-oxopentanoate (2.5 g, quant) as a solid. MS (ESI) m/z 403.0 [M+H]$^+$.

To a solution of (S)-tert-butyl 5-amino-4-(1-bromo-4-oxo-4H-thieno[3,4-c]pyrrol-5(6H)-yl)-5-oxopentanoate (1.20 g, 3.00 mmol) in DMF (6 mL) was added 1,1'-bis(diphenylphosphino)ferrocene (333 mg, 0.60 mmol), zinc cyanide (388 mg, 3.30 mmol) and tris(dibenzylideneacetone)dipalladium (275 mg, 0.30 mmol). After $N_2$ purge, the mixture was stirred at 150° C. under microwave for 1 h. The mixture was diluted with water and extracted with EA. The combined organic layers were washed with brine, dried over $Na_2SO_4$, filtered, and concentrated. The residue was purified using silica gel eluting with PE/EA (1:2) to give (S)-tert-butyl 5-amino-4-(1-cyano-4-oxo-4H-thieno[3,4-c]pyrrol-5 (6H)-yl)-5-oxopentanoate (260 mg, 26% yield) as a solid. MS (ESI) m/z 350.1 [M+Na]$^+$.

To (S)-tert-butyl 5-amino-4-(1-cyano-4-oxo-4H-thieno[3,4-c]pyrrol-5(6H)-yl)-5-oxopentanoate (260 mg, 0.74 mmol) in a solution of AcOH (2 mL), pyridine (4 mL), and water (2 mL) was added sodium hypophosphite (320 mg, 3.72 mmol) and Raney Ni (50 mg). After 1 h, the mixture was filtered. The filtrate was concentrated, diluted with DCM, washed with 1N HCl, and brine, dried over Na$_2$SO$_4$, filtered, and concentrated. The residue was purified using silica gel eluting with PE/EA (1:2) to give (S)-tert-butyl 5-amino-4-(1-formyl-4-oxo-4H-thieno[3,4-c]pyrrol-5(6H)-yl)-5-oxopentanoate (130 mg, 50% yield) as a solid. MS (ESI) m/z 353.1 [M+H]$^+$.

To a solution of (S)-tert-butyl 5-amino-4-(1-formyl-4-oxo-4H-thieno[3,4-c]pyrrol-5(6H)-yl)-5-oxopentanoate (130 mg, 0.37 mmol) in MeOH (4 mL) at 0° C. was added sodium borohydride (8.5 g, 0.22 mmol). The mixture was stirred at RT for 3 h then concentrated and purified by prep-TLC eluting with EA to give (S)-tert-butyl 5-amino-4-(1-(hydroxymethyl)-4-oxo-4H-thieno[3,4-c]pyrrol-5(6H)-yl)-5-oxopentanoate (100 mg, 76% yield) as solid. MS (ESI) m/z 355.1 [M+Na]$^+$.

To a solution of (S)-tert-butyl 5-amino-4-(1-(hydroxymethyl)-4-oxo-4H-thieno[3,4-c]pyrrol-5(6H)-yl)-5-oxopentanoate (100 mg, 0.28 mmol), 4-dimethylaminopyridine (3.5 mg, 0.028 mmol) and TEA (57 mg, 0.56 mmol) in DCM (4 mL) was added tosyl chloride (108 mg, 0.56 mmol). The mixture was stirred for 2 h then concentrated to give (S)-tert-butyl 5-amino-4-(1-(chloromethyl)-4-oxo-4H-thieno[3,4-c]pyrrol-5(6H)-yl)-5-oxopentanoate (80 mg, crude) as a solid. MS (ESI) m/z 373.1 [M+H]$^+$.

To a solution 4-hydroxybenzaldehyde (1.0 g, 8.2 mmol) and morpholine (1 mL) in DCM (20 mL) was added sodium triacetoxyborohydride (3.50 g, 16.4 mmol). After heating at RT overnight, the mixture was washed with saturated aqueous NaHCO$_3$, dried over Na$_2$SO$_4$, filtered, and concentrated. The residue was purified using silica gel eluting with PE/EA (1:1) to give 4-(morpholinomethyl)phenol (1.0 g, 63% yield) as a solid. MS (ESI) m/z 194.1 [M+H]$^+$.

To a solution of (S-tert-butyl 5-amino-4-(1-(chloromethyl)-4-oxo-4H-thieno[3,4-c]pyrrol-5(6H)-yl)-5-oxopentanoate (80 mg, 0.21 mmol, crude) and 4-(morpholinomethyl)phenol (81 mg, 0.42 mmol) in ACN (4 mL) was added K$_2$CO$_3$ (60 mg, 0.42 mmol). The mixture was stirred at 80° C. for 2 h then concentrated, and the residue was purified using silica gel eluting with PE/EA (1:2) to give (S)-tert-butyl 5-amino-4-(1-((4-(morpholinomethyl)phenoxy)methyl)-4-oxo-4H-thieno[3,4-c]pyrrol-5(6H)-yl)-5-oxopentanoate (60 mg, 52% yield) as an oil. MS (ESI) m/z 530.2 [M+H]$^+$.

To a solution of (S)-tert-butyl 5-amino-4-(1-((4-(morpholinomethyl)phenoxy)methyl)-4-oxo-4H-thieno[3,4-c]pyrrol-5 (6H)-yl)-5-oxopentanoate (60 mg, 0.11 mmol) in DCM (4 mL) was added TFA (1 mL). The mixture was stirred for 1 h then concentrated to give (S)-5-amino-4-(1-((4-(morpholinomethyl)phenoxy)methyl)-4-oxo-4H-thieno[3,4-c]pyrrol-5(6H)-yl)-5-oxopentanoic acid (0.11 mmol, crude) as a solid, which was used in the next step without further purification.

To a solution (S)-5-amino-4-(1-((4-(morpholinomethyl)phenoxy)methyl)-4-oxo-4H-thieno[3,4-c]pyrrol-5(6H)-yl)-5-oxopentanoic acid (0.11 mmol, crude) in ACN (4 mL) was added CDI (72 mg, 0.44 mmol). The mixture was stirred at 95° C. for 3 h then concentrated and purified by prep-TLC eluting with EA to afford Compound 1 (26.8 mg, 53% yield) as a solid. MS (ESI) m/z 456.1 [M+H]$^+$. $^1$H NMR (400 MHz, DMSO-d$_6$) δ 10.99 (s, 1H), 8.02 (s, 1H), 7.23 (d, J=8.4 Hz, 2H), 6.98 (d, J=8.4 Hz, 2H), 5.28 (s, 2H), 5.02 (dd, J=4.8, 13.2 Hz, 1H), 4.35 (d, J=15.6 Hz, 1H), 4.22 (d, J=16.0 Hz, 1H), 3.55 (d, J=4.0 Hz, 4H), 3.37-3.40 (m, 2H), 2.84-2.93 (m, 1H), 2.56-2.60 (m, 1H), 2.29-2.37 (m, 5H), 1.96-2.00 (m, 1H).

Example 2

Compound 2: (S)-3-(3-((4-(morpholinomethyl)benzyl)oxy)-6-oxo-4H-thieno[2,3-c]pyrrol-5(6H)-yl)piperidine-2,6-dione

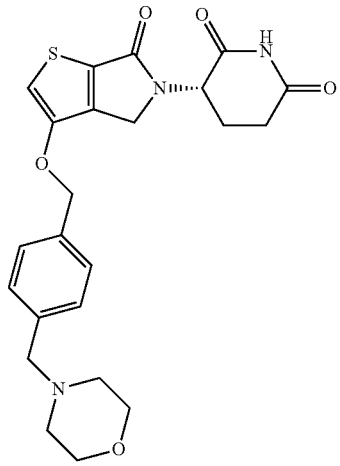 [SMILES: O=C1CC[C@H](N2Cc3c(OCc4ccc(CN5CCOCC5)cc4)csc3C2=O)C(=O)N1]

To a solution of methyl 4-bromo-3-methylthiophene-2-carboxylate (15.0 g, 64.1 mmol) in THF (100 mL) and MeOH (50 mL) at 0° C. was added LiOH (163 mmol). The mixture was stirred at RT overnight then concentrated. The residue was acidified with 2M HCl to a pH of approximately 3 to 4. The mixture was filtered and the filter cake was dried to give 4-bromo-3-methylthiophene-2-carboxylic acid (12.5 g, 89% yield) as a solid.

To a solution of 4-bromo-3-methylthiophene-2-carboxylic acid (11.5 g, 52.3 mmol) in DCM (100 mL) at 0° C. was added (COCl)$_2$ (13.3 g, 549 mmol) and DMF (1 mL) dropwise. After 2 h, the mixture was concentrated. The residue was dissolved in THF (100 mL) and a solution of t-BuOK (17.6 g, 157 mmol) in THF (50 mL) was added. The mixture was stirred for 1 h then quenched with water and extracted with DCM. The combined organic layers were dried over Na$_2$SO$_4$, filtered, and concentrated to give tert-butyl 4-bromo-3-methylthiophene-2-carboxylate (9.2 g, 64% yield) as an oil.

To a solution of tert-butyl 4-bromo-3-methylthiophene-2-carboxylate (8.60 g, 31.3 mmol) in 1,4-dioxane (150 mL) was added KOAc (9.20 g, 93.8 mmol) and bis(pinacolato)diboron (11.9 g, 46.9 mmol). After N$_2$ purge, Pd(PPh$_3$)Cl$_2$ (4.6 g, 6.3 mmol) was added and the mixture was heated at 100° C. overnight. After concentration, the residue was purified using silica gel eluting with PE/EA (1:2) to give tert-butyl 3-methyl-4-(4,4,5,5-tetramethyl-1,3,2-dioxaborolan-2-yl)thiophene-2-carboxylate (6.45 g, 64% yield) as a solid.

To a solution of tert-butyl 3-methyl-4-(4,4,5,5-tetramethyl-1,3,2-dioxaborolan-2-yl)thiophene-2-carboxylate (6.97 g, 21.5 mmol) in acetone (90 mL) and water (90 mL) at 0° C. was added NaIO$_4$ (13.8 g, 64.5 mmol) and NH$_4$OAc (3.3 g, 43 mmol). The mixture was stirred at RT overnight then concentrated. The residue was purified using silica gel eluting with PE/EA (1:1) to give (5-(tert-butoxycarbonyl)-4-methylthiophen-3-yl)boronic acid (2.08 g, 40% yield) as a solid.

To a solution of (5-(tert-butoxycarbonyl)-4-methylthiophen-3-yl)boronic acid (2.08 g, 8.39 mmol) in ether (50 mL) at 0° C. was added $H_2O_2$ (2.5 mL). After 2 h, the reaction was quenched with saturated $Na_2SO_3$ and exacted with EA. The combined organic layers were washed with brine, dried over $Na_2SO_4$, filtered, and concentrated. The residue was purified using silica gel eluting with PE/EA (1:1) to give tert-butyl 4-hydroxy-3-methylthiophene-2-carboxylate (1.6 g, 89% yield) as a gum.

To a solution of tert-butyl 4-hydroxy-3-methylthiophene-2-carboxylate (1.50 g, 7.01 mmol) in DMF (3 mL) was added imidazole (1.43 g, 21.0 mmol) and TBDMSCl (1.58 g, 10.51 mmol). After heating at 60° C. for 1 h, water was added, and the mixture was extracted with methyl tert-butyl ether. The combined organic layers were washed with brine, dried over $Na_2SO_4$, filtered, and concentrated. The residue was purified using silica gel eluting with PE/EA (1:1) to give tert-butyl 4-((tert-butyldimethylsilyl)oxy)-3-methylthiophene-2-carboxylate (2.23 g, 97% yield) as an oil.

To a solution of tert-butyl 4-((tert-butyldimethylsilyl)oxy)-3-methylthiophene-2-carboxylate (1.93 g, 5.88 mmol) in $CCl_4$ (50 mL) was added NBS (1.10 g, 6.18 mmol) and AIBN (506 mg, 2.94 mmol). After heating at reflux overnight, the mixture was concentrated. The residue was dissolved in water and extracted with EA. The combined organic layers were dried over $Na_2SO_4$, filtered, and concentrated. The residue was purified using silica gel eluting with PE/EA (1:1) to give tert-butyl 3-(bromomethyl)-4-((tert-butyldimethylsilyl) oxy)thiophene-2-carboxylate (2.0 g, 84% yield) as an oil.

To a solution of (S)-methyl 4,5-diamino-5-oxopentanoate (1.7 g, 6.2 mmol) in DMF (50 mL) at 0° C. was added DIEA (1.85 g, 14.33 mmol) and tert-butyl 3-(bromomethyl)-4-((tert-butyldimethylsilyl) oxy)thiophene-2-carboxylate (1.94 g, 4.78 mmol). After stirring at RT overnight, the mixture was diluted with water and extracted with EA. The combined layers were dried over $Na_2SO_4$, filtered, and concentrated. The residue was purified using silica gel eluting with PE/EA (1:2) to give (S)-tert-butyl 3-(((1-amino-5-methoxy-1,5-dioxopentan-2-yl)amino)methyl)-4-((tert-butyldimethylsilyl)oxy)thiophene-2-carboxylate (815 mg, 35% yield) as an oil. MS (ESI) m/z 487 [M+H]$^+$.

To a solution of (S)-tert-butyl 3-(((1-amino-5-methoxy-1,5-dioxopentan-2-yl)amino)methyl)-4-((tert-butyldimethylsilyl)oxy)thiophene-2-carboxylate (715 mg, 1.47 mmol) in DCM (10 mL) at 0° C. was added TFA (3 mL). The mixture was stirred at RT for 8 h then concentrated to give (S)-3-(((1-amino-5-methoxy-1,5-dioxopentan-2-yl)amino) methyl)-4-((tert-butyldimethylsilyl)oxy)thiophene-2-carboxylic acid (633 mg, quant) as an oil. MS (ESI) m/z 431 [M+H]$^+$.

To a solution of (S)-3-(((1-amino-5-methoxy-1,5-dioxopentan-2-yl)amino)methyl)-4-((tert-butyldimethylsilyl)oxy) thiophene-2-carboxylic acid (633 mg, 1.47 mmol) in DMF (15 mL) at 0° C. was added HATU (670.8 g, 1.765 mmol) and DIEA (474.4 mg, 3.678 mmol). After 8 h, the mixture was diluted with water and extracted with DCM. The combined organic layers were dried over $Na_2SO_4$, filtered, and concentrated. The residue was triturated with EA to give (S)-methyl 5-amino-4-(3-((tert-butyldimethylsilyl)oxy)-6-oxo-4H-thieno[2,3-c]pyrrol-5(6H)-yl)-5-oxopentanoate (606 mg, quant) as a solid. MS (ESI) m/z 413 [M+H]$^+$.

To a solution of (S)-methyl 5-amino-4-(3-((tert-butyldimethylsilyl)oxy)-6-oxo-4H-thieno[2,3-c]pyrrol-5(6H)-yl)-5-oxopentanoate (606 mg, 1.47 mmol) in DMF (14 mL) was added TBAF (463.3 mg, 1.471 mmol). After heating at 40° C. for 1 h, the mixture was cooled to RT then 4-(4-(chloromethyl)benzyl)morpholine (845 mg, 3.24 mmol) and $K_2CO_3$ (304.5 mg, 2.206 mmol) were added. The mixture was heated at 50° C. overnight then cooled to RT, quenched with water, and extracted with EA. The combined organic layers were dried over $Na_2SO_4$, filtered, and concentrated. The residue was triturated with EA to give (S)-methyl 5-amino-4-(3-((4-(morpholinomethyl)benzyl)oxy)-6-oxo-4H-thieno[2,3-c]pyrrol-5(6H)-yl)-5-oxopentanoate (80 mg, 11% yield) as a solid. MS (ESI) m/z 488 [M+H]$^+$.

To a solution of (S)-methyl 5-amino-4-(3-((4-(morpholinomethyl)benzyl)oxy)-6-oxo-4H-thieno[2,3-c]pyrrol-5(6H)-yl)-5-oxopentanoate (80 mg, 0.16 mmol) in THF (5 mL) at 0° C. was added LiOH (0.5 mL, 0.49 mmol). After 2 h, the mixture was concentrated. The residue was acidified with 2M HCl to a pH of approximately 4 to 5 and extracted with EA. The combined organic layers were dried over $Na_2SO_4$, filtered, and concentrated to give (S)-5-amino-4-(3-((4-(morpholinomethyl)benzyl)oxy)-6-oxo-4H-thieno[2,3-c]pyrrol-5(6H)-yl)-5-oxopentanoic acid (77.7 mg, crude) as a solid, which was used in the next step without further purification.

To a solution of (S)-5-amino-4-(3-((4-(morpholinomethyl)benzyl)oxy)-6-oxo-4H-thieno[2,3-c]pyrrol-5(6H)-yl)-5-oxopentanoic acid (77.7 mg, 0.164 mmol) in ACN (5 mL) was added CDI (106.4 mg, 0.6568 mmol). The mixture was heated to 80° C. overnight then concentrated. The residue was purified using silica gel eluting with EA in petroleum from 0% to 90% and further purified by prep-HPLC (5 μM $C_{18}$ column, 0.1% TFA in $H_2O$, 0.1% TFA in ACN, 5%-95%) to afford Compound 2 (12.7 mg, 17% yield) as a solid. MS (ESI) m/z 456 [M+H]$^+$. $^1$H NMR (400 MHz, DMSO-d$_6$) δ 10.95 (s, 1H), 7.32-7.43 (m, 4H), 7.18 (s, 1H), 5.11 (s, 2H), 4.96-5.00 (m, 1H), 4.15-4.37 (m, 2H), 3.55-3.57 (m, 4H), 3.46 (s, 2H), 2.83-2.92 (m, 1H), 2.55-2.59 (m, 1H), 2.34 (s, 5H), 1.97-2.00 (m, 1H).

Example 3

Compound 3: (S)-3-(3-((4-(morpholinomethyl)benzyl)amino)-6-oxo-4H-thieno[2,3-c]pyrrol-5(6H)-yl) piperidine-2,6-dione

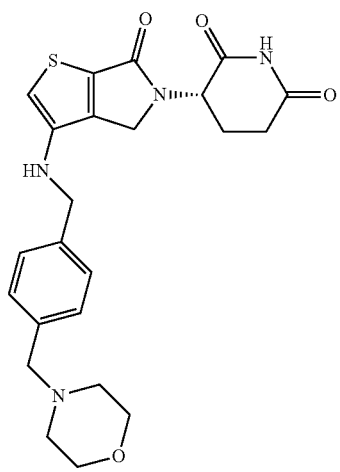 [SMILES: O=C1CC[C@H](N2Cc3c(NCc4ccc(CN5CCOCC5)cc4)csc3C2=O)C(=O)N1]

To a mixture of (S)-tert-butyl 5-amino-4-(3-bromo-6-oxo-4H-thieno[2,3-c]pyrrol-5(6H)-yl)-5-oxopentanoate (1.00 g, 2.48 mmol), (4-(morpholinomethyl)phenyl)methanamine (1.00 g, 4.96 mmol) and cesium carbonate (2.40 g, 7.44 mmol) in N,N-dimethylethanolamine (5 mL) was added Pd-peppsi-IpentCl (208 mg, 0.248 mmol). After purging with $N_2$, the mixture was stirred at 120° C. under microwave for 3 h. The mixture was diluted with water and extracted with EA. The combined organic layers were washed with brine, dried over $Na_2SO_4$, filtered, and concentrated. The residue was purified by prep-TLC eluting with PE/EA (1:2) to give (S)-tert-butyl 5-amino-4-(3-((4-(morpholinomethyl)benzyl)amino)-6-oxo-4H-thieno[2,3-c]pyrrol-5(6H)-yl)-5-oxopentanoate (100 mg, 8% yield) as a solid. MS (ESI) m/z 529.3 [M+H]$^+$.

To a solution of (S)-tert-butyl 5-amino-4-(3-((4-(morpholinomethyl)benzyl)-amino)-6-oxo-4H-thieno[2,3-c]pyrrol-5(6H)-yl)-5-oxopentanoate (100 mg, 0.19 mmol) in DCM (4 mL) was added TFA (1 mL). The mixture was stirred for 1 h then concentrated to give (S)-5-amino-4-(3-((4-(morpholinomethyl)benzyl)amino)-6-oxo-4H-thieno[2,3-c]pyrrol-5(6H)-yl)-5-oxopentanoic acid (0.19 mmol, crude) as a solid, which was used in the next step without further purification.

To a solution (S)-5-amino-4-(3-((4-(morpholinomethyl)benzyl)amino)-6-oxo-4H-thieno[2,3-c]pyrrol-5(6H)-yl)-5-oxopentanoic acid (0.19 mmol, crude) in ACN (4 mL) was added CDI (125 mg, 0.771 mmol). After heating at 95° C. for 3 h, the mixture was concentrated and purified by prep-HPLC as previously described to afford Compound 3 (10.2 mg, 12% yield) as a solid. MS (ESI) m/z 455.1 [M+H]$^+$. $^1$H NMR (400 MHz, DMSO-$d_6$) δ 10.94 (s, 1H), 7.23-7.35 (m, 4H), 6.29-6.32 (m, 2H), 4.97 (dd, J=5.2, 13.2 Hz, 1H), 4.15-4.22 (m, 4H), 3.55 (t, J=4.8 Hz, 4H), 3.41 (s, 2H), 2.83-2.92 (m, 1H), 2.56-2.61 (m, 1H), 2.25-2.33 (m, 5H), 1.99-2.04 (m, 1H).

Example 4

Compound 4: S)-3-(3-(4-(morpholinomethyl)phenethyl)-6-oxo-4H-thieno[2,3-c]pyrrol-5(6H)-yl)piperidine-2,6-dione

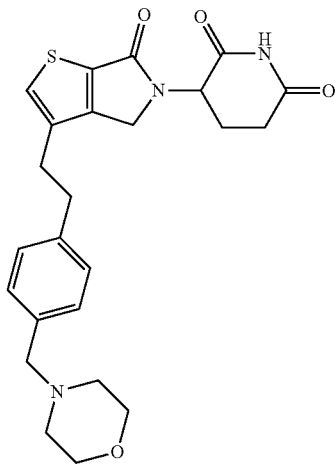 [SMILES: O=C1CCC(N2Cc3c(CCc4ccc(CN5CCOCC5)cc4)csc3C2=O)C(=O)N1]

To 4,5-bis(diphenylphosphino)-9,9-dimethylxanthene (1.34 g, 2.31 mmol) in THF (40 mL) was added cuprous chloride (230 mg, 2.31 mmol) and sodium tert-butoxide (445 mg, 4.62 mmol). After 30 m under $N_2$, a solution of 4,4,4',4',5,5,5',5'-octamethyl-2,2'-bi(1,3,2-dioxaborolane) (19.6 g, 0.077 mol) in THF (20 mL) was added. After 10 m, a solution of 4-ethynylbenzaldehyde (10.0 g, 0.077 mol) in THF (40 mL) was added. The mixture was stirred overnight then concentrated, and the residue was purified using silica gel eluting with PE/EA (50:1) to give (E)-4-(2-(4,4,5,5-tetramethyl-1,3,2-dioxaborolan-2-yl)vinyl)benzaldehyde (2.4 g, 12% yield) as a solid. $^1$H NMR (400 MHz, CDCl$_3$) δ 9.99 (s, 1H), 7.85 (d, J=7.6 Hz, 2H), 7.62 (d, J=8.0 Hz, 2H), 7.42 (d, J=18.4 Hz, 1H), 6.32 (d, J=18.4 Hz, 1H), 1.26 (s, 12H).

To a solution of (S)-tert-butyl 5-amino-4-(3-bromo-6-oxo-4H-thieno[2,3-c]pyrrol-5(6H)-yl)-5-oxopentanoate (700 mg, 1.74 mmol) and (E)-4-(2-(4,4,5,5-tetramethyl-1,3,2-dioxaborolan-2-yl)vinyl)benzaldehyde (900 mg, 3.48 mmol) in 1,4-dioxane (9 mL) and water (1 mL) was added potassium phosphate (1.10 g, 5.22 mmol) and [1,1'-bis(diphenylphosphino)ferrocene]-dichloropalladium(II) (254 mg, 0.35 mmol). The mixture was heated at 110° C. overnight under $N_2$ then water was added, and the mixture was extracted with EA. The combined organic layers were washed with brine, dried over $Na_2SO_4$, and concentrated. The residue was purified using silica gel eluting with PE/EA (1:1 to 100% EA) to give (S,E)-tert-butyl 5-amino-4-(3-(4-formylstyryl)-6-oxo-4H-thieno[2,3-c]pyrrol-5(6H)-yl)-5-oxopentanoate (370 mg, 47% yield) as a solid. MS (ESI) m/z=477.1 [M+Na]$^+$.

To a solution of (S,E)-tert-butyl 5-amino-4-(3-(4-formylstyryl)-6-oxo-4H-thieno[2,3-c]pyrrol-5(6H)-yl)-5-oxopentanoate (370 mg, 0.81 mmol) in isopropanol (10 mL) was added 10% Pd/C (740 mg). The mixture was stirred overnight under $H_2$ then filtered and concentrated to give (S)-tert-butyl 5-amino-4-(3-(4-(hydroxymethyl)phenethyl)-6-oxo-4H-thieno[2,3-c]pyrrol-5(6H)-yl)-5-oxopentanoate (371 mg, crude) which was used for the next step without purification. MS (ESI) m/z=459.2 [M+H]$^+$.

To a solution of (S)-tert-butyl 5-amino-4-(3-(4-(hydroxymethyl)phenethyl)-6-oxo-4H-thieno[2,3-c]pyrrol-5(6H)-yl)-5-oxopentanoate (371 mg, 0.81 mmol, crude) in DCM (10 mL) was added Dess-Martin (345 mg, 0.81 mmol). After 2 h, aqueous saturated sodium thiosulfate was added, and the mixture was extracted with EA. The combined organic layers were washed with saturated NaHCO$_3$ followed by brine then dried over $Na_2SO_4$, filtered, and concentrated to give (S)-tert-butyl 5-amino-4-(3-(4-formylphenethyl)-6-oxo-4H-thieno[2,3-c]pyrrol-5(6H)-yl)-5-oxopentanoate (300 mg, crude) as a solid. MS (ESI) m/z=457.2 [M+H]$^+$.

To a solution of (S)-tert-butyl 5-amino-4-(3-(4-formylphenethyl)-6-oxo-4H-thieno[2,3-c]pyrrol-5(6H)-yl)-5-oxopentanoate (300 mg, 0.68 mmol, crude) and morpholine (115 mg, 1.32 mmol) in DCM (10 mL) was added sodium triacetoxyborohydride (420 mg, 1.98 mmol). After 2 h, the mixture was concentrated, and the residue was purified using prep-TLC eluting with PE/EA (1:1) to give (S)-tert-butyl 5-amino-4-(3-(4-(morpholinomethyl)phenethyl)-6-oxo-4H-thieno[2,3-c]pyrrol-5(6H)-yl)-5-oxopentanoate (200 mg, 58% yield) as a solid. MS (ESI) m/z=528.3 [M+H]$^+$.

To a solution of (S)-tert-butyl 5-amino-4-(3-(4-(morpholinomethyl)phenethyl)-6-oxo-4H-thieno[2,3-c]pyrrol-5(6H)-yl)-5-oxopentanoate (200 mg, 0.38 mmol) in DCM (4 mL) was added TFA (2 mL). After 1 h, the mixture was concentrated to give (S)-5-amino-4-(3-(4-(morpholinomethyl)phenethyl)-6-oxo-4H-thieno[2,3-c]pyrrol-5(6H)-yl)-5-oxopentanoic acid (200 mg, 0.38 mmol, crude) which was used in the next step without purification. MS (ESI) m/z=472.2 [M+H]⁺.

To a solution (S)-5-amino-4-(3-(4-(morpholinomethyl) phenethyl)-6-oxo-4H-thieno[2,3-c]pyrrol-5(6H)-yl)-5-oxopentanoic acid (200 mg, 0.38 mmol, crude) in ACN (10 mL) was added CDI (250 mg, 1.52 mmol). The mixture was stirred at 90° C. overnight then concentrated, and the residue was purified using prep-HPLC as previously described to afford Compound 4 (36 mg, 21% yield) as a solid. MS (ESI) m/z=454.1 [M+H]⁺. ¹H NMR (400 MHz, DMSO-$d_6$) δ 10.96 (s, 1H), 7.65 (s, 1H), 7.16-7.21 (m, 4H), 4.98 (dd, J=4.8, 13.2 Hz, 1H), 4.11-4.26 (m, 2H), 3.55 (t, J=4.4 Hz, 4H), 3.40 (s, 2H), 2.84-2.92 (m, 5H), 2.56-2.61 (m, 1H), 2.28-2.34 (m, 5H), 1.96-1.99 (m, 1H).

Example 5

Compound 5: (S)-3-(3-((4-(morpholinomethyl)phenoxy)methyl)-6-oxo-4H-thieno[2,3-c]pyrrol-5(6H)-yl)piperidine-2,6-dione

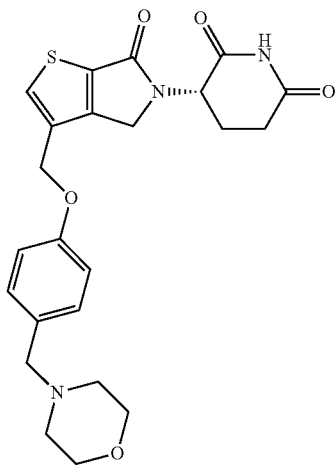 [SMILES: O=C1CC[C@H](N2Cc3c(COc4ccc(CN5CCOCC5)cc4)csc3C2=O)C(=O)N1]

To a solution of methyl 4-bromo-3-methylthiophene-2-carboxylate (10.0 g, 42.5 mmol) in CCl₄ (50 mL) was added 1-bromo-2,5-pyrrolidinedione (9.09 g, 51.1 mmol) and benzoyl peroxide (1.03 g, 4.25 mmol). The mixture was stirred at 85° C. for 16 h. The mixture was filtered and the filter cake was washed with DCM. The combined organic layers were concentrated, and the residue was purified using silica gel eluting with PE/EA (1:1) to give methyl 4-bromo-3-(bromomethyl)thiophene-2-carboxylate (10.42 g, crude) as a solid, which was used in the next step without further purification.

To a solution of methyl 4-bromo-3-(bromomethyl)thiophene-2-carboxylate (10.42 g, 33.17 mmol, crude) in DMF (50 mL) at 0° C. was added (S)-tert-butyl 4,5-diamino-5-oxopentanoate hydrochloride (9.50 g, 39.8 mmol) and TEA (7.37 g, 72.9 mmol). The mixture was stirred at RT overnight and concentrated. The residue was purified using silica gel eluting with PE/EA (1:2) to give (S)-methyl 3-(((1-amino-5-(tert-butoxy)-1,5-dioxopentan-2-yl)amino) methyl)-4-bromothiophene-2-carboxylate (11.53 g, 80% yield) as oil. MS (ESI) m/z 435.1, 437.1 [M+H]⁺.

To a solution of (S)-methyl 3-(((1-amino-5-(tert-butoxy)-1,5-dioxopentan-2-yl)amino)methyl)-4-bromothiophene-2-carboxylate (11.53 g, 26.49 mmol) in THF (110 mL) was added LiOH monohydrate (1.67 g, 39.7 mmol) and water (66 mL). The mixture was stirred for 3 h then concentrated. The residue was diluted with water and acidified with 1M HCl to a pH of 6. After stirring 0.5 h, the mixture was filtered and the filter cake was washed with water and dried to afford (S)-3-(((1-amino-5-(tert-butoxy)-1,5-dioxopentan-2-yl) amino)methyl)-4-bromothiophene-2-carboxylic acid (14.7 g, crude) as a solid. MS (ESI) m/z 421.0, 423.0 [M+H]⁺.

To a solution of (S)-3-(((1-amino-5-(tert-butoxy)-1,5-dioxopentan-2-yl)amino)methyl)-4-bromothiophene-2-carboxylic acid (6.70 g, crude, 15.9 mmol) in DMF (150 mL) at 0° C. was added 1-hydroxybenzotriazole (3.22 g, 23.9 mmol), N-(3-dimethylaminopropyl)-N'-ethylcarbodiimide hydrochloride (4.58 g, 23.9 mmol) and DIEA (6.17 g, 47.7 mmol). The mixture was stirred at RT for 2 h then concentrated. The residue was purified using silica gel eluting with PE/EA (1:1) to give (S)-tert-butyl 5-amino-4-(3-bromo-6-oxo-4H-thieno[2,3-c]pyrrol-5(6H)-yl)-5-oxopentanoate (2.73 g, 43% yield) as a solid. MS (ESI) m/z 347.0, 349.0 [M-55]⁺.

To a solution of (S)-tert-butyl 5-amino-4-(3-bromo-6-oxo-4H-thieno[2,3-c]pyrrol-5(6H)-yl)-5-oxopentanoate (1.00 g, 2.48 mmol) in DMF (6 mL) was added zinc cyanide (320 mg, 2.73 mmol), tris(dibenzylideneacetone)dipalladium (229 mg, 0.25 mmol) and 1,1'-bis(diphenylphosphino) ferrocene (302 mg, 0.55 mmol). The mixture was stirred at 150° C. under microwave for 1 h then concentrated. The residue was purified using silica gel eluting with PE/EA (1:2) to give (S)-tert-butyl 5-amino-4-(3-cyano-6-oxo-4H-thieno[2,3-c]pyrrol-5(6H)-yl)-5-oxopentanoate (428 mg, 50% yield) as a solid. MS (ESI) m/z 294.0 [M-55]⁺.

To (S)-tert-butyl 5-amino-4-(3-cyano-6-oxo-4H-thieno[2,3-c]pyrrol-5(6H)-yl)-5-oxopentanoate (1.12 g, 3.21 mmol) and sodium dihydric hypophosphite (1.66 g, 19.26 mmol) in a solution of AcOH (5 mL), pyridine (10 mL) and water (5 mL) was added Raney-Ni (200 mg). The mixture was stirred for 1 h then filtered and the filter cake was washed with DCM. The combined organic layers were washed with 1N HCl and concentrated. The residue was purified using silica gel eluting with PE/EA (1:2) to give (S)-tert-butyl 5-amino-4-(3-formyl-6-oxo-4H-thieno[2,3-c]pyrrol-5(6H)-yl)-5-oxopentanoate (550 mg, 49% yield) as a solid. MS (ESI) m/z 297.1, 299.1 [M-55]⁺.

To a solution of (S)-tert-butyl 5-amino-4-(3-formyl-6-oxo-4H-thieno[2,3-c]pyrrol-5(6H)-yl)-5-oxopentanoate (550 mg, 1.56 mmol) in MeOH (40 mL) was added sodium borohydride (24 mg, 0.63 mmol) at 0° C. The mixture was stirred at RT for 2 h then concentrated. The residue was diluted with water and extracted with DCM. The combined organic layers were concentrated to give (S)-tert-butyl 5-amino-4-(3-(hydroxymethyl)-6-oxo-4H-thieno[2,3-c]pyrrol-5(6H)-yl)-5-oxopentanoate (497 mg, 91% yield) as a solid. MS (ESI) m/z 299.1, 300.1 [M-55]⁺.

To a solution of (S)-tert-butyl 5-amino-4-(3-(hydroxymethyl)-6-oxo-4H-thieno[2,3-c]pyrrol-5(6H)-yl)-5-oxopentanoate (180 mg, 0.51 mmol), 4-dimethylaminopyridine (6.0 mg, 0.05 mmol) and TEA (103 mg, 1.02 mmol) in DCM (10 mL) was added p-toluenesulfonyl chloride (145 mg, 0.76 mmol). After 3 h, the reaction was quenched with aqueous ammonium chloride solution and extracted with DCM. The combined organic layers were concentrated and purified using silica gel eluting with PE/EA (1:2) to give (S)-tert-butyl 5-amino-4-(3-(chloromethyl)-6-oxo-4H-thieno[2,3-c] pyrrol-5(6H)-yl)-5-oxopentanoate (100 mg, 53% yield) as an oil. MS (ESI) m/z 317.0, 319.0 [M-55]⁺.

To a solution of (S)-tert-butyl 5-amino-4-(3-(chloromethyl)-6-oxo-4H-thieno[2,3-c]pyrrol-5(6H)-yl)-5-oxopentanoate (100 mg, 0.27 mmol) in ACN (10 mL) was added 4-(morpholinomethyl)phenol (104 mg, 0.54 mmol) and K$_2$CO$_3$ (75 mg, 0.54 mmol). The mixture was stirred at 80° C. for 16 h then concentrated. The residue was purified using silica gel eluting with PE/EA (1:2 to 100% EA) to give (S)-tert-butyl 5-amino-4-(3-((4-(morpholinomethyl)phenoxy)methyl)-6-oxo-4H-thieno[2,3-c]pyrrol-5 (6H)-yl)-5-oxopentanoate (70 mg, 49% yield) as an oil. MS (ESI) m/z 474.1, 476.1 [M-55]$^+$.

A mixture of (S)-tert-butyl 5-amino-4-(3-((4-(morpholinomethyl)phenoxy)methyl)-6-oxo-4H-thieno[2,3-c]pyrrol-5 (6H)-yl)-5-oxopentanoate (70 mg, 0.13 mmol) in TFA (1.0 mL) and DCM (4.0 mL) was stirred for 1 h then concentrated to give (S)-5-amino-4-(3-((4-(morpholinomethyl)phenoxy)methyl)-6-oxo-4H-thieno[2,3-c]pyrrol-5 (6H)-yl)-5-oxopentanoic acid (62 mg, 0.13 mmol, crude) as an oil, which was used in the next step without further purification. MS (ESI) m/z 474.2 [M+H]$^+$.

A mixture of (S)-5-amino-4-(3-((4-(morpholinomethyl)phenoxy)methyl)-6-oxo-4H-thieno[2,3-c]pyrrol-5(6H)-yl)-5-oxopentanoic acid (62 mg, 0.13 mmol, crude) and CDI (84 mg, 0.52 mmol) in ACN (5 mL) was heated at reflux for 72 h then concentrated. The residue was purified by prep-HPLC as previously described to afford Compound 5 (28 mg, 47% yield) as a solid. MS (ESI) m/z 456.1 [M+H]$^+$. $^1$H NMR (400 MHz, DMSO-d$_6$) δ 10.98 (s, 1H), 8.02 (s, 1H), 7.22 (d, J=8.8, 2H), 6.98 (d, J=8.4, 2H), 5.1 5 (s, 2H), 5.01 (dd, J=13.2, 4.8, 1H), 4.36 (dd, J=48.0, 18.0, 2H), 3.55 (t, J=4.4, 4H), 3.38 (s, 2H), 2.93-2.84 (m, 1H), 2.67-2.55 (m, 1H), 2.51-2.31 (m, 5H), 2.01-1.98 (m, 1H).

Example 6

Compound 6: (S)-3-(1-(4-(morpholinomethyl)phenethyl)-4-oxo-4H-thieno[3,4-c]pyrrol-5(6H)-yl)piperidine-2,6-dione

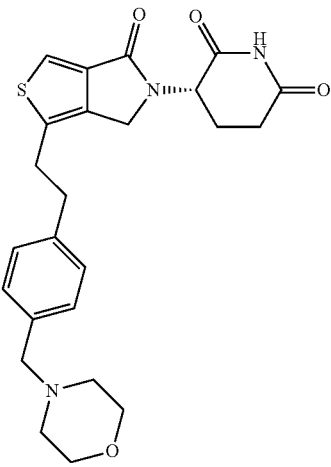 [SMILES: O=C1CC[C@H](N2Cc3c(csc3CCc3ccc(CN4CCOCC4)cc3)C2=O)C(=O)N1]

To a solution of (S)-tert-butyl 5-amino-4-(1-bromo-4-oxo-4H-thieno[3,4-c]pyrrol-5(6H)-yl)-5-oxopentanoate (500 mg, 1.24 mmol) in toluene (30 mL) and water (3 mL) was added (E)-4-(2-(4,4,5,5-tetramethyl-1,3,2-dioxaborolan-2-yl)vinyl)benzaldehyde (640 mg, 2.48 mmol), K$_2$CO$_3$ (514 mg, 3.72 mmol) and 1,1'-bis(diphenylphosphino)ferrocene]dichloropalladium(II) (181 mg, 0.25 mmol). After heating at 100° C. overnight, the mixture was filtered and the filter cake was washed with DCM. The combined organic layers were concentrated, and the residue was purified using silica gel eluting with PE/EA (1:1) to give (S,E)-tert-butyl 5-amino-4-(1-(4-formylstyryl)-4-oxo-4H-thieno[3,4-c]pyrrol-5(6H)-yl)-5-oxopentanoate (337 mg, 60% yield) as a solid. MS (ESI) m/z 399.0 [M-55]$^+$.

To a solution of (S,E)-tert-butyl 5-amino-4-(1-(4-formylstyryl)-4-oxo-4H-thieno[3,4-c]pyrrol-5(6H)-yl)-5-oxopentanoate (420 mg, 0.93 mmol) in isopropanol (30 mL) under N$_2$ was added Pd/C (1.27 g, 10%, 0.28 mmol). The mixture was degassed and purged with H$_2$ then stirred overnight. After filtration, the filter cake was washed with EA. The combined organic layers were concentrated to give (S)-tert-butyl 5-amino-4-(1-(4-(hydroxymethyl)phenethyl)-4-oxo-4H-thieno[3,4-c]pyrrol-5(6H)-yl)-5-oxopentanoate (crude) as an oil, which was used in the next step without further purification. MS (ESI) m/z 403 [M-55]$^+$.

To a solution of (S)-tert-butyl 5-amino-4-(1-(4-(hydroxymethyl)phenethyl)-4-oxo-4H-thieno[3,4-c]pyrrol-5 (6H)-yl)-5-oxopentanoate (0.93 mmol, crude) in DCM (30.0 mL) was added Dess-Martin periodinane (394 mg, 0.93 mmol). After 2 h, the mixture was quenched with saturated sodium thiosulfate and extracted with DCM. The combined organic layers were washed with saturated aqueous NaHCO$_3$, and brine, then concentrated to give (S)-tert-butyl 5-amino-4-(1-(4-formylphenethyl)-4-oxo-4H-thieno[3,4-c]pyrrol-5(6H)-yl)-5-oxopentanoate (1.0 mmol, crude) as an oil, which was use in the next step without further purification. MS (ESI) m/z 401 [M-55]$^+$.

To a solution of (S)-tert-butyl 5-amino-4-(1-(4-formylphenethyl)-4-oxo-4H-thieno[3,4-c]pyrrol-5(6H)-yl)-5-oxopentanoate (1.0 mmol, crude), morpholine (174 mg, 2.0 mmol) in DCM (30 mL) was added sodium borohydride acetate (636 mg, 3.0 mmol). The mixture was stirred overnight then quenched with saturated sodium thiosulfate and extracted with DCM. The combined organic layers were washed with saturated aqueous NaHCO$_3$, and brine, then concentrated and purified using silica gel eluting with PE/EA (1:2) to give (S)-tert-butyl 5-amino-4-(1-(4-(morpholinomethyl)phenethyl)-4-oxo-4H-thieno[3,4-c]pyrrol-5 (6H)-yl)-5-oxopentanoate (150 mg, 28% yield) as an oil. MS (ESI) m/z 472 [M-55]$^+$.

A mixture of (S)-tert-butyl 5-amino-4-(1-(4-(morpholinomethyl)phenethyl)-4-oxo-4H-thieno[3,4-c]pyrrol-5(6H)-yl)-5-oxopentanoate (100 mg, 0.19 mmol) and TFA (2 mL) in DCM (8 mL) was stirred for 2 h then concentrated to give (S)-5-amino-4-(1-(4-(morpholinomethyl)phenethyl)-4-oxo-4H-thieno[3,4-c]pyrrol-5(6H)-yl)-5-oxopentanoic acid (0.19 mmol, crude) as an oil, which was used in the next step without further purification. MS (ESI) m/z 472 [M+H]$^+$.

A mixture of (S)-5-amino-4-(1-(4-(morpholinomethyl)phenethyl)-4-oxo-4H-thieno[3,4-c]pyrrol-5(6H)-yl)-5-oxopentanoic acid (0.19 mmol, crude) and CDI (123 mg, 0.76 mmol) in ACN (10 mL) was heated at 80° C. overnight then concentrated. The residue was purified by prep-HPLC as previously described to afford Compound 6 (19 mg, 22% yield) as a solid. MS (ESI) m/z 454.0 [M+H]$^+$. $^1$H NMR (400 MHz, DMSO-d$_6$) δ 10.94 (s, 1H), 7.78 (s, 1H), 7.21-7.16 (m, 4H), 4.98 (dd, J=13.2, 5.2 Hz, 1H), 4.04 (dd, J=38.8, 15.2 Hz, 2H), 3.56-3.54 (m, 4H), 3.41 (s, 2H), 3.09-3.05 (m, 2H), 2.92-2.85 (m, 3H), 2.60-2.55 (m, 1H), 2.33-2.24 (m, 5H), 1.95-1.90 (m, 1H).

Example 7

Compound 7: (S)-3-(1-((3-(morpholinomethyl)phenoxy)methyl)-4-oxo-4H-thieno[3,4-c]pyrrol-5(6H)-yl)piperidine-2,6-dione

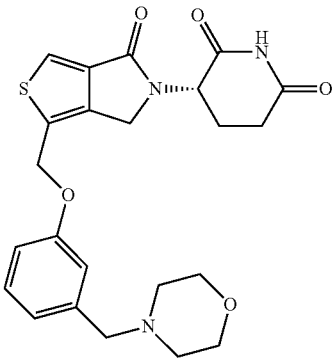 [SMILES: O=C1CC[C@H](N2Cc3c(csc3COc3cccc(CN4CCOCC4)c3)C2=O)C(=O)N1]

To a solution of (S)-tert-butyl-5-amino-4-(1-(chloromethyl)-4-oxo-4H-thieno[3,4-c]pyrrol-5(6H)-yl)-5-oxopentanoate (110 mg, 0.30 mmol) in ACN (3 mL) was added 3-(morpholinomethyl)phenol (87 mg, 0.45 mmol) and K$_2$CO$_3$ (83 mg, 0.60 mmol). After heating at 90° C. for 4 h, the mixture was diluted with water (5 mL) and extracted with EA (5 mL). The combined organic layers were dried over Na$_2$SO$_4$, filtered, and concentrated. The residue was purified using silica gel eluting with PE/EA (1:4) to give (S)-tert-butyl 5-amino-4-(1-((3-(morpholinomethyl)phenoxy)methyl)-4-oxo-4H-thieno[3,4-c]pyrrol-5 (6H)-yl)-5-oxopentanoate (114 mg, 72% yield) as an solid. MS (ESI) m/z 530.2 [M+H]$^+$.

To a solution of (S)-tert-butyl 5-amino-4-(1-((3-(morpholinomethyl) phenoxy)methyl)-4-oxo-4H-thieno[3,4-c]pyrrol-5(6H)-yl)-5-oxopentanoate (114 mg, 0.22 mmol) in DCM (6 mL) was added TFA (2 mL). The mixture was stirred for 2 h then concentrated to give (S)-5-amino-4-(1-((3-(morpholinomethyl)phenoxy)methyl)-4-oxo-4H-thieno[3,4-c]pyrrol-5(6H)-yl)-5-oxopentanoic acid (104 mg, quant) as a solid. MS (ESI) m/z 474.1 [M+H]$^+$.

To a solution of (S)-5-amino-4-(1-((3-(morpholinomethyl)phenoxy)methyl)-4-oxo-4H-thieno[3,4-c]pyrrol-5 (6H)-yl)-5-oxopentanoic acid (104 mg, 0.22 mmol) in ACN (6 mL) was added CDI (1.78 mg, 1.10 mmol). After heating at 90° C. for 16 h, the mixture was filtered, and the filtrate was concentrated. The residue was purified by prep-HPLC as previously described to afford Compound 7 (18.6 mg, 19% yield) as a solid. MS (ESI) m/z 456.1 [M+H]$^+$. $^1$H NMR (400 MHz, DMSO-d$_6$) δ 11.00 (s, 1H), 8.03 (s, 1H), 7.26 (t, J=8.0 Hz, 1H), 6.96-6.91 (m, 3H), 5.31 (s, 2H), 5.05-5.01 (m, 1H), 4.37-4.20 (m, 2H), 3.56 (t, J=4.4 Hz, 4H), 3.43 (s, 2H), 2.94-2.85 (m, 1H), 2.61-2.51 (m, 1H), 2.39-2.27 (m, 5H), 2.00-1.97 (m, 1H).

Example 8

Compound 8: (S)-3-(1-((2-fluoro-4-(morpholinomethyl)phenoxy)methyl)-4-oxo-4H-thieno[3,4-c]pyrrol-5(6H)-yl)piperidine-2,6-dione

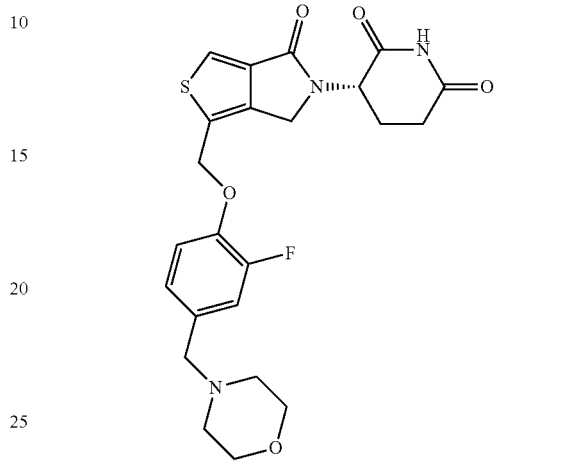

A mixture of 2-fluoro-4-hydroxybenzaldehyde (1.4 g, 10 mmol) and morpholine (1.3 g, 15 mmol) in DCM (30 mL) was stirred for 0.5 h then NaBH$_3$CN (1.3 g, 20 mmol) was added. After 0.5 h, the mixture was washed with water and the organic layer was concentrated. The residue was purified using silica gel eluting with PE/EA (1:12) to give 3-fluoro-4-(morpholinomethyl)phenol (660 mg, 32% yield) as a solid. MS (ESI) m/z 212 [M+H]$^+$.

To a solution of (S)-tert-butyl 5-amino-4-(1-(chloromethyl)-4-oxo-4H-thieno[3,4-c]pyrrol-5(6H)-yl)-5-oxopentanoate (100 mg, 0.27 mmol) and 2-fluoro-4-(morpholinomethyl)phenol (85 mg, 0.42 mmol) in ACN (5 mL) was added K$_2$CO$_3$ (75 mg, 0.54 mmol). After heating at reflux for 3 h, the mixture was quenched with water and extracted with EA. The combined organic layers were concentrated to give (S)-tert-butyl 5-amino-4-(1-((2-fluoro-4-(morpholinomethyl)phenoxy)methyl)-4-oxo-4H-thieno[3,4-c]pyrrol-5 (6H)-yl)-5-oxopentanoate (163 mg, crude) as an oil. MS (ESI) m/z 548 [M+H]$^+$.

To a solution of (S)-tert-butyl 5-amino-4-(1-((2-fluoro-4-(morpholinomethyl)phenoxy)methyl)-4-oxo-4H-thieno[3,4-c]pyrrol-5 (6H)-yl)-5-oxopentanoate (148 mg, 0.27 mmol, crude) in DCM (5 mL) was added TFA (2 mL). The mixture was stirred for 3 h then concentrated. The residue was dissolved in ACN (5 mL) and CDI was added (66 mg, 0.41 mmol). After heating at reflux overnight, the mixture was cooled to RT, washed with water, and extracted with EA. The combined organic layers were concentrated and purified by prep-HPLC as previously described to afford Compound 8 (21.3 mg, 18% yield) as a solid. MS (ESI) m/z 474.1 [M+H]$^+$. $^1$H NMR (400 MHz, DMSO-d$_6$) δ 10.97 (s, 1H), 8.03 (s, 1H), 7.18 (m, 2H), 7.06 (m, 1H), 5.35 (s, 2H), 5.02 (m, 1H), 4.27 (q, 2H), 3.55 (t, 4H), 3.39 (s, 2H), 2.88 (m, 1H), 2.58 (m, 1H), 2.32 (m, 1H), 2.31 (t, 4H), 1.99 (m, 1H).

Example 9

Compound 9: (S)-3-(1-(((4-(morpholinomethyl) benzyl)oxy) methyl)-4-oxo-4H-thieno[3,4-c]pyrrol-5 (6H)-yl)piperidine-2,6-dione

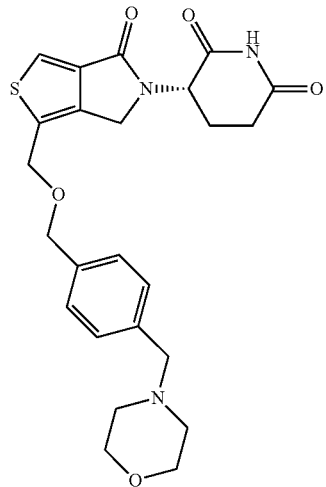 [SMILES: O=C1CC[C@H](N2Cc3c(csc3COCc3ccc(CN4CCOCC4)cc3)C2=O)C(=O)N1]

To a solution of (S)-tert-butyl 5-amino-4-(1-(hydroxymethyl)-4-oxo-4H-thieno[3,4-c]pyrrol-5(6H)-yl)-5-oxopentanoate (370 mg, 1.05 mmol) and 4-(bromomethyl)benzaldehyde (420 mg, 2.1 mmol) in ACN (10 mL) was added $K_2CO_3$ (580 mg, 4.2 mmol). After heating at reflux for 1 h, the mixture was concentrated, and the residue was purified using silica gel eluting with EA to give (S)-tert-butyl 5-amino-4-(1-(((4-formylbenzyl)oxy)methyl)-4-oxo-4H-thieno[3,4-c]pyrrol-5(6H)-yl)-5-oxopentanoate (60 mg, 13% yield) as an oil. MS (ESI) m/z 473.2 [M+H]$^+$.

To a solution of (S)-tert-butyl 5-amino-4-(1-(((4-formylbenzyl)oxy)methyl)-4-oxo-4H-thieno[3,4-c]pyrrol-5(6H)-yl)-5-oxopentanoate (60 mg, 0.127 mmol) in DCM (2 mL) was added TFA (0.5 mL). After 2 h, the mixture was concentrated to give (S)-5-amino-4-(1-(((4-formylbenzyl) oxy)methyl)-4-oxo-4H-thieno[3,4-c]pyrrol-5(6H)-yl)-5-oxopentanoic acid (0.127 mmol, crude) as a solid, which was used in the next step without further purification. MS (ESI) m/z 417.1 [M+H]$^+$.

To a solution (S)-5-amino-4-(1-(((4-formylbenzyl)oxy) methyl)-4-oxo-4H-thieno[3,4-c]pyrrol-5(6H)-yl)-5-oxopentanoic acid (0.127 mmol, crude) in ACN (2 mL) was added CDI (81 mg, 0.5 mmol). After heating at 90° C. for 2 h, the mixture was concentrated, and the residue was purified by prep-TLC eluting with PE/EA (1:2) to give (S)-4-(((5-(2,6-dioxopiperidin-3-yl)-4-oxo-5,6-dihydro-4H-thieno[3,4-c] pyrrol-1-yl)methoxy)methyl)benzaldehyde (40 mg, 80% yield) as a solid. MS (ESI) m/z 399.1 [M+H]$^+$.

To a solution 4-hydroxybenzaldehyde (S)-4-(((5-(2,6-dioxopiperidin-3-yl)-4-oxo-5,6-dihydro-4H-thieno[3,4-c]pyrrol-1-yl)methoxy)methyl)benzaldehyde (40 mg, 0.10 mmol) and morpholine (26 mg, 0.30 mmol) in DCM (4 mL) was added sodium triacetoxyborohydride (106 mg, 0.50 mmol). After 1 h, the mixture was concentrated, and the residue was purified by prep-HPLC as previously described to afford Compound 9 (5.3 mg, 11% yield) as a solid. MS (ESI) m/z 470.1 [M+H]$^+$. $^1$H NMR (400 MHz, DMSO-d$_6$) δ 10.96 (s, 1H), 7.98 (s, 1H), 7.28 (s, 4H), 5.28 (s, 2H), 5.01 (dd, J=5.2, 12.8 Hz, 1H), 4.68 (s, 2H), 4.53 (s, 2H), 4.30 (d, J=15.6 Hz, 1H), 4.16 (d, J=16.0 Hz, 1H), 3.55 (t, J=4.4 Hz, 4H), 3.44 (s, 2H), 2.55-2.60 (m, 1H), 2.51-2.52 (m, 1H), 2.29-2.33 (m, 5H), 1.96-2.00 (m, 1H).

Example 10

Compound 10: (S)-3-(1-(((4-(morpholinomethyl) phenyl)amino)methyl)-4-oxo-4H-thieno[3,4-c]pyrrol-5(6H)-yl)piperidine-2,6-dione

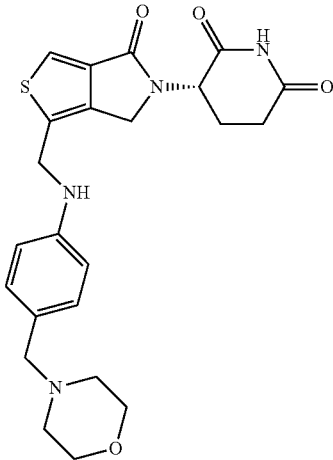 [SMILES: O=C1CC[C@H](N2Cc3c(csc3CNc3ccc(CN4CCOCC4)cc3)C2=O)C(=O)N1]

To a solution of (S)-tert-butyl 5-amino-4-(1-formyl-4-oxo-4H-thieno[3,4-c]pyrrol-5(6H)-yl)-5-oxopentanoate (140 mg, 0.397 mmol) and 4-(morpholinomethyl)aniline (92.0 mg, 0.477 mmol) in DCM (5 mL) was added NaBH(OAc)$_3$ (253 mg, 1.197 mmol). The mixture was stirred for 2 h then concentrated, and the residue was purified using silica gel eluting with PE/EA (1:2) give (S)-tert-butyl 5-amino-4-(1-(((4-(morpholinomethyl)phenyl)amino) methyl)-4-oxo-4H-thieno[3,4-c]pyrrol-5(6H)-yl)-5-oxopentanoate (130 mg, 62% yield) as a solid. MS (ESI) m/z 529.3 [M+H]$^+$.

To a solution of (S)-tert-butyl 5-amino-4-(1-(((4-(morpholinomethyl)phenyl)amino)methyl)-4-oxo-4H-thieno[3,4-c]pyrrol-5(6H)-yl)-5-oxopentanoate (130 mg, 0.246 mmol) in DCM (4 mL) was added TFA (1 mL). The mixture was stirred overnight then concentrated and dissolved in ACN (6 mL). CDI (120 mg, 0.738 mmol) was added, and the mixture was heated at 90° C. for 3 h. After concentration, the residue was purified by prep-HPLC as previously described to afford Compound 10 (25.2 mg 22% yield) as a solid. MS (ESI) m/z 455.1 [M+H]$^+$. $^1$H NMR (400 MHz, DMSO-d$_6$) δ 10.97 (s, 1H), 7.83 (s, 1H), 6.99 (d, J=8.4 Hz, 2H), 6.56 (d, J=8.8 Hz, 2H), 6.27 (t, J=6.0 Hz, 1H), 5.01-4.97 (m, 1H), 4.42 (d, J=5.6 Hz, 2H), 4.27-4.13 (m, 2H), 3.52 (s, 4H), 3.27 (s, 2H), 2.87-2.86 (m, 1H), 2.59-2.54 (m, 1H), 2.32-2.27 (m, 5H), 1.96-1.90 (m, 1H).

Example 11

Compound 11: (S)-3-(3-(((4-(morpholinomethyl)phenyl)amino)methyl)-6-oxo-4H-thieno[2,3-c]pyrrol-5(6H)-yl)piperidine-2,6-dione

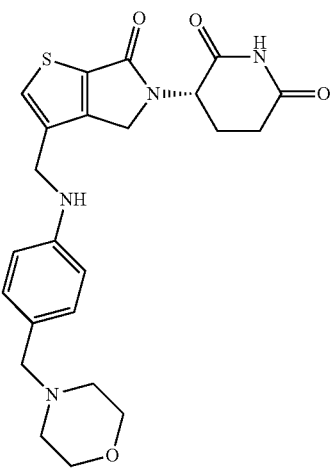 [SMILES: O=C1CC[C@H](N2Cc3c(CNc4ccc(CN5CCOCC5)cc4)csc3C2=O)C(=O)N1]

To a mixture of (S)-tert-butyl 5-amino-4-(3-bromo-6-oxo-4H-thieno[2,3-c]pyrrol-5(6H)-yl)-5-oxopentanoate (1.50 g, 3.73 mmol), Pd$_2$(dba)$_3$ (355 mg, 0.37 mmol) and dppf (401 mg, 0.74 mmol) in DMF (22 mL) under N$_2$ was added Zn(CN)$_2$ (481 mg, 4.10 mmol). The mixture was heated at 150° C. under microwave for 1 h. After cooling to RT, the mixture was diluted with water, filtered, and extracted with EA. The organic layers were washed with brine, dried over Na$_2$SO$_4$, filtered, and concentrated. The residue was purified using silica gel eluting with PE/EA (1:2) to give (S)-tert-butyl 5-amino-4-(3-cyano-6-oxo-4H-thieno[2,3-c]pyrrol-5(6H)-yl)-5-oxopentanoate (300 mg, 23% yield) as an oil. MS (ESI) m/z 294.1 [M+H-56]t To (S)-tert-butyl 5-amino-4-(3-cyano-6-oxo-4H-thieno[2,3-c]pyrrol-5(6H)-yl)-5-oxopentanoate (300 mg, 0.86 mmol) in a solution of AcOH (1 mL), pyridine (5 mL), and water (1 mL) at 0° C. was added NaH$_2$PO$_2$ (370 mg, 4.30 mmol) and Raney Ni (200 mg). The mixture was stirred for 4 h then filtered. The filtrate was extracted with EA and the combined organic layers were washed with 1 N HCl, and brine, then dried over Na$_2$SO$_4$, filtered, and concentrated. The residue was purified using silica gel eluting with PE/EA (1:2) to give (S)-tert-butyl 5-amino-4-(3-formyl-6-oxo-4H-thieno[2,3-c]pyrrol-5(6H)-yl)-5-oxopentanoate (170 mg, 56% yield) as a solid. MS (ESI) m/z 297.1 [M+H-56]$^+$.

To a solution of (S)-tert-butyl 5-amino-4-(3-formyl-6-oxo-4H-thieno[2,3-c]pyrrol-5(6H)-yl)-5-oxopentanoate (170 mg, 0.483 mmol) and 4-(morpholinomethyl)aniline (130 mg, 0.676 mmol) in DCM (4 mL) was added NaBH(OAc)$_3$ (307 mg, 1.45 mmol). The mixture was stirred for 2 h then concentrated. The residue was purified using silica gel eluting with PE/EA (1:2) to give (S)-tert-butyl 5-amino-4-(3-(((4-(morpholinomethyl)phenyl)amino)methyl)-6-oxo-4H-thieno[2,3-c]pyrrol-5(6H)-yl)-5-oxopentanoate (220 mg, 86% yield) as a solid. MS (ESI) m/z 529.3 [M+H]$^+$.

To a solution of (S)-tert-butyl 5-amino-4-(3-(((4-(morpholinomethyl) phenyl)amino)methyl)-6-oxo-4H-thieno[2,3-c]pyrrol-5(6H)-yl)-5-oxopentanoate (220 mg, 0.416 mmol) in DCM (4 mL) was added TFA (1 mL). The mixture was stirred overnight then concentrated. The residue was dissolved in ACN (6 mL) and CDI (203 mg, 1.250 mmol) was added. The mixture was heated at 90° C. for 3 h then concentrated. The residue was purified by prep-HPLC as previously described to afford Compound 11 (45.1 mg 23% yield) as a solid. MS (ESI) m/z 455.1 [M+H]$^+$. $^1$H NMR (400 MHz, DMSO-d$_6$) δ 10.95 (s, 1H), 7.80 (s, 1H), 6.97 (d, J=8.0 Hz, 2H), 6.56 (d, J=8.8 Hz, 2H), 6.07 (t, J=6.0 Hz, 1H), 5.01-4.96 (m, 1H), 4.36-4.22 (m, 4H), 3.52 (t, J=4.4 Hz, 4H), 3.26 (s, 2H), 2.87-2.86 (m, 1H), 2.60-2.57 (m, 1H), 2.31-2.27 (m, 5H), 2.00-1.90 (m, 1H).

Example 12

Compound 12: (S)-3-(1-(((5-(morpholinomethyl)pyridin-2-yl)oxy)methyl)-4-oxo-4H-thieno[3,4-c]pyrrol-5(6H)-yl)piperidine-2,6-dione

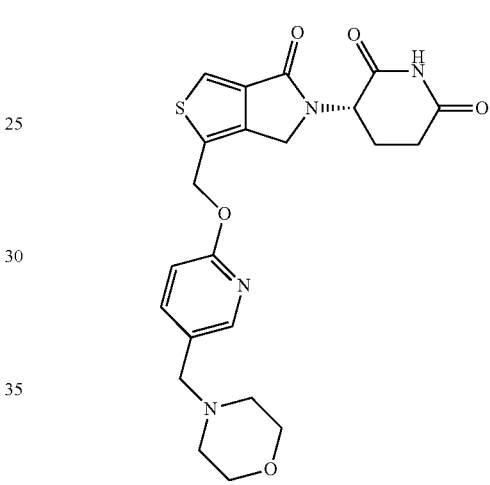

To a mixture of (S)-tert-butyl 5-amino-4-(1-(chloromethyl)-4-oxo-4H-thieno[3,4-c]pyrrol-5(6H)-yl)-5-oxopentanoate (150 mg, 0.27 mmol) and 5-(morpholinomethyl)pyridin-2-ol (92 mg, 0.32 mmol), in ACN (10 mL) was added K$_2$CO$_3$ (75 mg, 0.54 mmol). After heating at reflux for 8 h, the mixture was concentrated, and the residue was purified by prep-TLC eluting with PE/EA (1:2) to give (S)-tert-butyl 5-amino-4-(1-(((5-(morpholinomethyl)pyridin-2-yl)oxy)methyl)-4-oxo-4H-thieno[3,4-c]pyrrol-5(6H)-yl)-5-oxopentanoate (40 mg, 19% yield) as a solid.

To a solution of (S)-tert-butyl 5-amino-4-(1-(((5-(morpholinomethyl)pyridin-2-yl)oxy)methyl)-4-oxo-4H-thieno[3,4-c]pyrrol-5(6H)-yl)-5-oxopentanoate (40 mg, 0.087 mmol) in DCM (3 mL) was added TFA (1 mL). The mixture was stirred for 2 h then concentrated. The residue was dissolved in ACN (3 mL) and CDI (43 mg, 0.262 mmol) was added. The mixture was heated at reflux for 8 h then diluted with water and extracted with EA. The combined organic layers were concentrated, and the residue was purified by prep-HPLC as previously described to afford Compound 12 (4.5 mg, 12% yield) as a solid. MS (ESI) m/z 456.8 [M+H]$^+$. $^1$H NMR (400 MHz, DMSO-d$_6$) δ 10.99 (s, 1H), 7.93 (s, 1H), 7.76 (d, 1H), 7.40 (m, 1H), 6.41 (d, 1H), 5.20 (q, 2H), 5.00 (m, 1H), 4.25 (q, 2H), 3.55 (t, 4H), 2.20 (s, 2H), 2.87 (m, 1H), 2.57 (m, 1H), 2.27 (t, 4H), 1.97 (m, 1H).

Example 13

Compound 13: (S)-3-(4-oxo-1-((4-(pyrrolidin-1-ylmethyl)phenoxy)methyl)-4H-thieno[3,4-c]pyrrol-5(6H)-yl)piperidine-2,6-dione

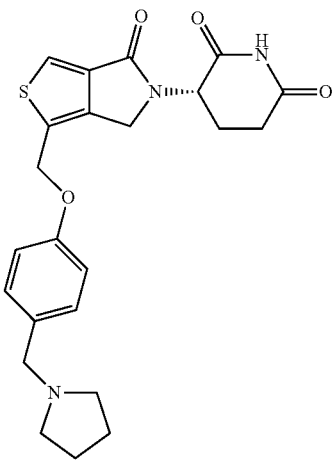 [SMILES: O=C1CC[C@H](N2Cc3c(csc3COc3ccc(CN4CCCC4)cc3)C2=O)C(=O)N1]

To a solution of (S)-tert-butyl 5-amino-4-(1-(chloromethyl)-4-oxo-4H-thieno[3,4-c]pyrrol-5(6H)-yl)-5-oxopentanoate (300 mg, 0.80 mmol) in ACN (10 mL) was added 4-hydroxybenzaldehyde (108 mg, 0.88 mmol), $K_2CO_3$ (166 mg, 1.20 mmol) and KI (133 mg, 0.80 mmol). The mixture was stirred for 3 h then concentrated. The residue was purified using silica gel eluting with PE/EA (1:2) to give (S)-tert-butyl 5-amino-4-(1-((4-formylphenoxy)methyl)-4-oxo-4H-thieno[3,4-c]pyrrol-5(6H)-yl)-5-oxopentanoate (350 mg, 95% yield) as a solid. MS (ESI) m/z 403.1 $[M+H-56]^+$.

To a solution of (S)-tert-butyl 5-amino-4-(1-((4-formylphenoxy)methyl)-4-oxo-4H-thieno[3,4-c]pyrrol-5(6H)-yl)-5-oxopentanoate (150 mg, 0.327 mmol) and pyrrolidine (70 mg, 0.982 mmol) in DCM (6 mL) was added NaBH(OAc)$_3$ (208 mg, 0.982 mmol). The mixture was stirred for 10 h then concentrated, and the residue was purified using silica gel eluting with PE/EA (1:2) to give (S)-tert-butyl 5-amino-5-oxo-4-(4-oxo-1-((4-(pyrrolidin-1-ylmethyl)phenoxy)methyl)-4H-thieno[3,4-c]pyrrol-5(6H)-yl)pentanoate (140 mg, 83% yield) as a solid. MS (ESI) m/z 514.2 $[M+H]^+$.

To a solution of (S)-tert-butyl 5-amino-5-oxo-4-(4-oxo-1-((4-(pyrrolidin-1-ylmethyl)phenoxy)methyl)-4H-thieno[3,4-c]pyrrol-5(6H)-yl)pentanoate (140 mg, 0.273 mmol) in DCM (4 mL) was added TFA (1 mL). The mixture was stirred overnight then concentrated. The residue was dissolved in ACN (8 mL) and CDI (133 mg, 0.818 mmol) was added. The mixture was heated at reflux for 4 h then concentrated. The residue was purified by prep-HPLC as previously described to afford Compound 13 (49.6 mg 41% yield) as a solid. MS (ESI) m/z 440.1 $[M+H]^+$. $^1$H NMR (400 MHz, DMSO-d$_6$) δ 10.97 (s, 1H), 8.01 (s, 1H), 7.21 (d, J=8.4 Hz, 2H), 6.96 (d, J=8.8 Hz, 2H), 5.28 (s, 2H), 5.04-4.99 (m, 1H), 4.36-4.20 (m, 2H), 3.49 (s, 2H), 2.94-2.84 (m, 1H), 2.60-2.56 (m, 1H), 2.38-2.31 (m, 5H), 2.00-1.96 (m, 1H), 1.68-1.65 (m, 4H).

Example 14

Compound 14: (S)-3-(1-((4-((diethylamino)methyl)phenoxy)methyl)-4-oxo-4H-thieno[3,4-c]pyrrol-5(6H)-yl)piperidine-2,6-dione

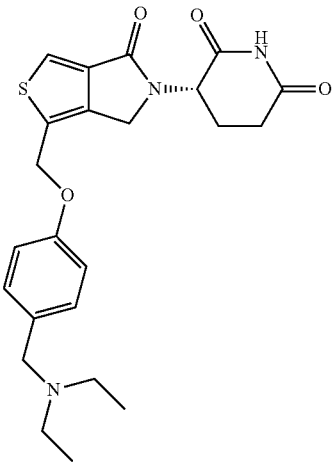 [SMILES: CCN(CC)Cc1ccc(OCc2scc3c2CN([C@H]2CCC(=O)NC2=O)C3=O)cc1]

To a solution of (S)-tert-butyl 5-amino-4-(1-((4-formylphenoxy)methyl)-4-oxo-4H-thieno[3,4-c]pyrrol-5(6H)-yl)-5-oxopentanoate (200 mg, 0.436 mmol) and DIEA (96 mg, 1.31 mmol) in DCM (6 mL) was added NaBH(OAc)$_3$ (278 mg, 1.31 mmol). The mixture was stirred for 10 h then concentrated. The residue was purified using silica gel eluting with PE/EA (1:2) to give (S)-tert-butyl 5-amino-4-(1-((4-((diethylamino)methyl)phenoxy)methyl)-4-oxo-4H-thieno[3,4-c]pyrrol-5(6H)-yl)-5-oxopentanoate (230 mg, crude) as an oil. MS (ESI) m/z 516.3 $[M+H]^+$.

To a solution of (S)-tert-butyl 5-amino-4-(1-((4-((diethylamino) methyl)phenoxy)methyl)-4-oxo-4H-thieno[3,4-c]pyrrol-5(6H)-yl)-5-oxopentanoate (230 mg, 0.446 mmol) in DCM (4 mL) was added TFA (1 mL). The mixture was stirred overnight then concentrated. The residue was dissolved in ACN (6 mL) and CDI (289 mg, 1.786 mmol) was added. The mixture was heated at reflux for 3 h then concentrated. The residue was purified by prep-HPLC as previously described to afford the trifluoroacetic acid salt of Compound 14 (25.8 mg, 13% yield) as a solid. MS (ESI) m/z 442.1 $[M+H]^+$. $^1$H NMR (400 MHz, DMSO-d$_6$) δ 10.97 (s, 1H), 9.31 (s, 1H), 8.03 (s, 1H), 7.46 (d, J=8.4 Hz, 2H), 7.12 (d, J=8.4 Hz, 2H), 5.35 (s, 2H), 5.05-5.00 (m, 1H), 4.338-4.20 (m, 4H), 3.08-3.00 (m, 4H), 2.90-2.85 (m, 1H), 2.61-2.56 (m, 1H), 2.35-2.30 (m, 1H), 1.99-1.97 (m, 1H), 1.23-1.19 (m, 6H).

Example 15

Compound 15: (S)-3-(1-((4-(2-morpholinoethyl)phenoxy)methyl)-4-oxo-4H-thieno[3,4-c]pyrrol-5(6H)-yl)piperidine-2,6-dione

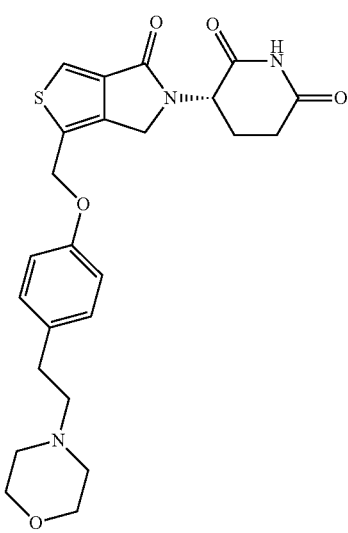 [SMILES: O=C1CC[C@H](N2Cc3c(csc3COc3ccc(CCN4CCOCC4)cc3)C2=O)C(=O)N1]

To a solution of 2-(4-(benzyloxy)phenyl)ethanol (2.4 g, 10.5 mmol) in DCM (20 mL) at 0° C. was added PBr₃ (3.4 g, 12.6 mmol) dropwise. The mixture was stirred at RT for 30 m, then water was added, and the mixture was extracted with DCM. The combined organic layers were washed with brine, dried over Na₂SO₄, filtered and concentrated to give 1-(benzyloxy)-4-(2-bromoethyl)benzene (2.6 g, 85% yield) as an oil which was used in the next step without purification.

To a solution of 1-(benzyloxy)-4-(2-bromoethyl)benzene (2.6 g, 8.93 mmol) in DMF (15 mL) was added morpholine (1.16 g, 13.3 mmol) and potassium carbonate (1.84 g, 13.3 mmol). The mixture was heated at 50° C. overnight then quenched with water and extracted with EA. The combined organic layers were dried over Na₂SO₄, filtered, and concentrated. The residue was purified using silica gel eluting with PE/EA (1:1) to give 4-(4-(benzyloxy)phenethyl)morpholine (1.5 g, 57% yield) as a solid. MS (ESI) m/z 298[M+H]⁺.

To a solution of 4-(4-(benzyloxy)phenethyl)morpholine (500 mg, 1.68 mmol) in MeOH (10 mL) was added Pd/C (200 mg). The mixture was degassed and purged with H₂. After stirring overnight, the mixture was filtered and concentrated to give 4-(2-morpholinoethyl)phenol (340 mg, yield: 98%) as an oil. MS (ESI) m/z 208[M+H]⁺.

To a stirred solution of (S)-tert-butyl 5-amino-4-(1-(chloromethyl)-4-oxo-4H-thieno[3,4-c]pyrrol-5(6H)-yl)-5-oxopentanoate (80 mg, 0.21 mmol) and 4-(2-morpholinoethyl)phenol (66 mg, 0.32 mmol) in ACN (8 mL) was added potassium carbonate (58 mg, 0.42 mmol). After 2 h at 80° C., the mixture was concentrated, and the residue was purified using silica gel eluting with PE/EA (1:1) to give (S)-tert-butyl 5-amino-4-(1-((4-(2-morpholinoethyl)phenoxy)methyl)-4-oxo-4H-thieno[3,4-c]pyrrol-5(6H)-yl)-5-oxopentanoate (100 mg, 85% yield) as a solid. MS (ESI) m/z=544 [M+H]⁺.

To a solution of (S)-tert-butyl 5-amino-4-(1-((4-(2-morpholinoethyl)phenoxy)methyl)-4-oxo-4H-thieno[3,4-c]pyrrol-5(6H)-yl)-5-oxopentanoate (100 mg, 0.22 mmol) in DCM (5 mL) was added TFA (2 mL). After 2 h, the mixture was concentrated, and the residue was dissolved in ACN (8 mL), and CDI (143 mg, 0.88 mmol) was added. After 3 h at 95° C., the mixture was washed with water. The organic phase was concentrated, and the residue was purified using prep-HPLC as previously described to afford Compound 15 (27 mg, 26% yield) as a solid. MS (ESI) m/z 470 [M+H]⁺. ¹H NMR (400 MHz, DMSO-d₆) δ 10.97 (s, 1H), 8.01 (s, 1H), 7.15 (d, J=8.4 Hz, 2H), 6.93 (d, J=8.8 Hz, 2H), 5.26 (s, 2H), 5.02 (dd, J=5.2, 5.2 Hz, 1H), 4.19-4.36 (q, 2H), 3.56 (t, 4H), 2.84-2.92 (m, 1H), 2.66 (t, 2H), 2.60 (m, 1H), 2.50 (m, 1H), 2.40 (t, 4H), 2.36 (m, 1H), 1.97-1.99 (m, 1H).

Example 16

Compound 16: (S)-3-(2-((4-(morpholinomethyl)phenoxy) methyl)-6-oxo-4H-thieno[2,3-c]pyrrol-5(6H)-yl)piperidine-2,6-dione

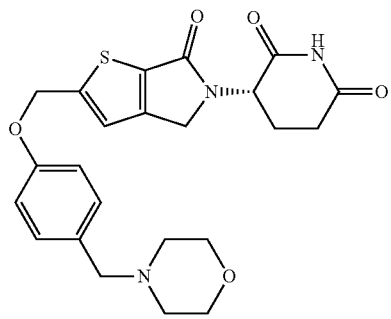 [SMILES: O=C1CC[C@H](N2Cc3cc(COc4ccc(CN5CCOCC5)cc4)sc3C2=O)C(=O)N1]

To a solution of 5-bromo-3-methylthiophene-2-carboxylic acid (4.4 g, 20 mmol) in DCM at 0° C. was added oxalyl chloride (5.1 g, 40 mmol) and DMF (10 drops). The mixture was stirred at 0° C. for 2 h then MeOH (20 mL) was added. After 1 h at 0° C., the mixture was concentrated, and the residue was purified using silica gel eluting with PE/EA (1:1) to give methyl 5-bromo-3-methylthiophene-2-carboxylate (2.615 g, 56% yield) as a solid.

To a solution of methyl 5-bromo-3-methylthiophene-2-carboxylate (2.615 g, 11.18 mmol) in CCl₄ (30 mL) was added NBS (2.387 g, 13.41 mmol) and benzoyl peroxide (270.5 mg, 1.12 mmol). The mixture was stirred at 85° C. for 16 h then cooled to RT, filtered, and washed with DCM. The combined organic layers were concentrated, and the residue was purified using silica gel eluting with PE/EA (1:1) to give methyl 5-bromo-3-(bromomethyl)thiophene-2-carboxylate (2.784 g, 80% yield) as a solid.

To a solution of methyl 5-bromo-3-(bromomethyl)thiophene-2-carboxylate (2.784 g, 8.92 mmol) in DMF (20 mL) at 0° C. was added (S)-tert-butyl 4,5-diamino-5-oxopentanoate (3.186 g, 13.39 mmol) and TEA (1.8 g, 17.84 mmol). The mixture was stirred for 16 h then concentrated. The residue was purified using silica gel eluting with PE/EA (1:2) to give (S)-methyl 3-(((1-amino-5-(tert-butoxy)-1,5-dioxopentan-2-yl)amino)methyl)-5-bromothiophene-2-carboxylate (3.439 g, 89% yield) as an oil. MS (ESI) m/z 435.1, 437.1 [M+H]⁺.

To a solution of (S)-methyl 3-(((1-amino-5-(tert-butoxy)-1,5-dioxopentan-2-yl)amino)methyl)-5-bromothiophene-2-carboxylate (2.51 g, 5.79 mmol) in THF (15 mL) and water (15 mL) was added LiOH monohydrate (365 mg, 8.68 mmol). After 3 h, the mixture was concentrated, and the residue was diluted with water. The aqueous layer was acidified with 1M HCl to a pH of 6. After stirring for 0.5 h, the mixture was filtered and the filter cake was washed with water then dried to give (S)-3-(((1-amino-5-(tert-butoxy)-1,5-dioxopentan-2-yl)amino)methyl)-5-bromothiophene-2-carboxylic acid (2.43 g, crude) as a solid. MS (ESI) m/z 421.0, 423.0 [M+H]$^+$.

To a solution of (S)-3-(((1-amino-5-(tert-butoxy)-1,5-dioxopentan-2-yl)amino)methyl)-5-bromothiophene-2-carboxylic acid (2.43 g, crude, 5.79 mmol) in DMF (20 mL) at 0° C. was added HATU (3.29 g, 8.68 mmol) and DIEA (1.49 g, 11.6 mmol). The mixture was stirred at RT for 2 h then concentrated. The residue was purified using silica gel eluting with PE/EA (1:2) to give (S)-tert-butyl 5-amino-4-(2-bromo-6-oxo-4H-thieno[2,3-c]pyrrol-5 (6H)-yl)-5-oxopentanoate (1.50 g, 65% yield) as a solid. MS (ESI) m/z 403.0, 405.0 [M+H]$^+$.

To a solution of (S)-tert-butyl 5-amino-4-(2-bromo-6-oxo-4H-thieno[2,3-c]pyrrol-5(6H)-yl)-5-oxopentanoate (1.50 g, 3.72 mmol) in DMF (24 mL) was added zinc cyanide (480 mg, 4.11 mmol), tris(dibenzylideneacetone) dipalladium (342 mg, 0.36 mmol) and 1,1'-bis(diphenylphosphino)ferrocene (453 mg, 0.81 mmol). The mixture was heated at 150° C. under microwave for 1 h then concentrated. The residue was purified using silica gel eluting with PE/EA (1:2) to give (S)-tert-butyl 5-amino-4-(2-cyano-6-oxo-4H-thieno[2,3-c]pyrrol-5(6H)-yl)-5-oxopentanoate (956 mg, 71% yield) as a solid. MS (ESI) m/z 350.1 [M+H]$^+$.

To (S)-tert-butyl 5-amino-4-(2-cyano-6-oxo-4H-thieno[2,3-c]pyrrol-5 (6H)-yl)-5-oxopentanoate (850 mg, 2.44 mmol) and sodium dihydric hypophosphite (1.07 g, 12.2 mmol) in a solution of AcOH (5 mL), pyridine (10 mL) and water (5 mL) was added Raney-Ni (300 mg). After 1 h, the mixture was filtered, and the filtrate was washed with 1M HCl then concentrated. The residue was purified using silica gel eluting with PE/EA (1:2) to give (S)-tert-butyl 5-amino-4-(2-formyl-6-oxo-4H-thieno[2,3-c]pyrrol-5(6H)-yl)-5-oxopentanoate (533 mg, 62% yield) as a solid. MS (ESI) m/z 353.1 [M+H]$^+$.

To a solution of (S)-tert-butyl 5-amino-4-(2-formyl-6-oxo-4H-thieno[2,3-c]pyrrol-5(6H)-yl)-5-oxopentanoate (594 mg, 1.69 mmol) in MeOH (20 mL) at 0° C. was added sodium borohydride (26 mg, 0.68 mmol). The mixture was stirred at RT for 2 h then concentrated. The residue was diluted with water and extracted with DCM. The combined organic layers were concentrated to give (S)-tert-butyl 5-amino-4-(2-(hydroxymethyl)-6-oxo-4H-thieno[2,3-c]pyrrol-5(6H)-yl)-5-oxopentanoate (408 mg, 68% yield) as a solid. MS (ESI) m/z 355.1 [M+H]$^+$.

To a solution of (S)-tert-butyl 5-amino-4-(2-(hydroxymethyl)-6-oxo-4H-thieno[2,3-c]pyrrol-5(6H)-yl)-5-oxopentanoate (308 mg, 0.87 mmol), 4-dimethylaminopyridine (10.9 mg, 0.08 mmol) and TEA (219 mg, 2.18 mmol) in DCM (10 mL) was added p-toluenesulfonyl chloride (249 mg, 1.31 mmol). The mixture was stirred for 3 h then quenched with aqueous ammonium chloride and extracted with DCM. The combined organic layers were concentrated and purified using silica gel eluting with PE/EA (1:2) to give (S)-tert-butyl 5-amino-4-(2-(chloromethyl)-6-oxo-4H-thieno[2,3-c]pyrrol-5(6H)-yl)-5-oxopentanoate (200 mg, 62% yield) as a solid. MS (ESI) m/z 373.1 [M+H]$^+$.

To a solution of (S)-tert-butyl 5-amino-4-(2-(chloromethyl)-6-oxo-4H-thieno[2,3-c]pyrrol-5(6H)-yl)-5-oxopentanoate (268 mg, 0.72 mmol) in ACN (10 mL) was added 4-(morpholinomethyl)phenol (278 mg, 1.44 mmol) and K$_2$CO$_3$ (198 mg, 1.44 mmol). The mixture was heated at 80° C. for 4 h then concentrated. The residue was purified using silica gel eluting with PE/EA (1:2) to give (S)-tert-butyl 5-amino-4-(2-((4-(morpholinomethyl)phenoxy)methyl)-6-oxo-4H-thieno[2,3-c]pyrrol-5(6H)-yl)-5-oxopentanoate (145 mg, 38% yield) as a solid. MS (ESI) m/z 530.2 [M+H]$^+$.

A mixture of (S)-tert-butyl 5-amino-4-(2-((4-(morpholinomethyl)phenoxy)methyl)-6-oxo-4H-thieno[2,3-c]pyrrol-5 (6H)-yl)-5-oxopentanoate (145 mg, 0.27 mmol) and TFA (4 mL) in DCM (8 mL) was stirred for 12 h then concentrated to give (S)-5-amino-4-(2-((4-(morpholinomethyl)phenoxy)methyl)-6-oxo-4H-thieno[2,3-c]pyrrol-5 (6H)-yl)-5-oxopentanoic acid (129 mg, 0.27 mmol, crude) as an oil, which was used in the next step without further purification. MS (ESI) m/z 474.2 [M+H]$^+$.

A mixture of (S)-5-amino-4-(2-((4-(morpholinomethyl)phenoxy)methyl)-6-oxo-4H-thieno[2,3-c]pyrrol-5(6H)-yl)-5-oxopentanoic acid (129 mg, 0.27 mmol, crude) and CDI (176 mg, 1.09 mmol) in ACN (10 mL) was stirred at 90° C. for 4 h. After concentration, the residue was purified by prep-HPLC as previously described to afford Compound 16 (28.1 mg, 23% yield) as a solid. MS (ESI) m/z 456.1 [M+H]$^+$. $^1$H NMR (400 MHz, DMSO-d$_6$) δ 10.97 (s, 1H), 7.34 (s, 1H), 7.24-7.22 (m, 2H), 7.01-6.99 (m, 2H), 5.38 (s, 2H), 5.00 (dd, J=8.4, 13.2 Hz, 1H), 4.55 (dd, J=36.4, 54.4 Hz, 2H), 3.58-3.52 (m, 4H), 3.38 (s, 2H), 2.92-2.84 (m, 1H), 2.60-2.56 (m, 1H), 2.41-2.31 (m, H), 2.02-1.98 (m, 1H).

Example 17

Compound 17: (3S)-3-(1-((4-((2,6-dimethylmorpholino) methyl)phenoxy)methyl)-4-oxo-4H-thieno[3,4-c]pyrrol-5(6H)-yl)piperidine-2,6-dione

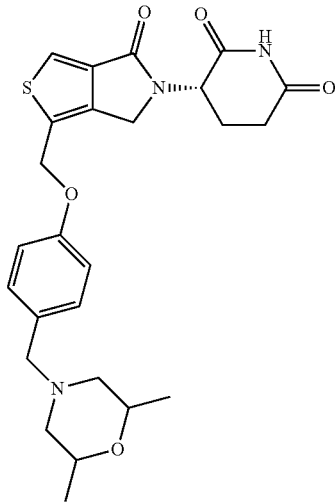 [SMILES: CC1CN(Cc2ccc(OCc3scc4c3CN([C@H]3CCC(=O)NC3=O)C4=O)cc2)CC(C)O1]

To a mixture of (S)-tert-butyl 5-amino-4-(1-(chloromethyl)-4-oxo-4H-thieno[3,4-c]pyrrol-5(6H)-yl)-5-oxopentanoate (372 mg, 1.0 mmol) with 4-hydroxybenzaldehyde (134 mg, 1.1 mmol) in ACN (10 mL) was added K$_2$CO$_3$ (269 mg, 1.5 mmol) and KI (83 mg, 0.5 mmol). After heating at reflux for 2 h, the mixture was diluted with water and extracted with EA. The combined organic layers were concentrated, and the residue was purified using silica gel eluting with DCM/MeOH (30:1 to 15:1) to give (S)-tert-butyl 5-amino-4-(1-((4-formylphenoxy)methyl)-4-oxo-4H-thieno[3,4-c]pyrrol-5(6H)-yl)-5-oxopentanoate (423 mg, 92% yield) as a solid.

To a mixture of (S)-tert-butyl 5-amino-4-(1-((4-formylphenoxy)methyl)-4-oxo-4H-thieno[3,4-c]pyrrol-5(6H)-yl)-5-oxopentanoate (200 mg, 0.44 mmol) and 2,6-dimethylmorpholine (50 mg, 0.44 mmol) in DCM (10 mL) was added NaBH$_3$CN (33 mg, 0.54 mmol). After stirring overnight, the mixture was concentrated, and the residue was purified by prep-TLC eluting with PE/EA (1:2) to give (4S)-tert-butyl 5-amino-4-(1-((4-((2,6-dimethylmorpholino)methyl)phenoxy)methyl)-4-oxo-4H-thieno[3,4-c]pyrrol-5(6H)-yl)-5-oxopentanoate (62 mg, 30% yield) as a solid. MS (ESI) m/z 557 [M+H]$^+$.

To a solution of (4S)-tert-butyl 5-amino-4-(1-((4-((2,6-dimethylmorpholino)methyl)phenoxy)methyl)-4-oxo-4H-thieno[3,4-c]pyrrol-5(6H)-yl)-5-oxopentanoate (62 mg, 0.11 mmol) in DCM (3 mL) was added TFA (1 mL). After stirring for 2 h, the mixture was concentrated. The residue was dissolved in ACN (5 mL) and CDI (89 mg, 0.55 mmol) was added. The mixture was heated at reflux overnight then concentrated. The residue was purified by prep-HPLC as previously described to afford Compound 17 (15 mg, 28% yield) as a solid. MS (ESI) m/z 484.1 [M+H]$^+$. $^1$H NMR (400 MHz, DMSO-d$_6$) δ 10.98 (s, 1H), 8.02 (s, 1H), 7.21 (d, 2H), 6.97 (d, 2H), 5.28 (s, 2H), 5.02 (m, 1H), 4.27 (q, 2H), 3.53 (t, 2H), 3.36 (t, 2H), 2.88 (m, 1H), 2.63 (m, 2H), 2.56 (m, 1H), 2.34 (m, 1H), 1.98 (m, 1H), 1.59 (m, 1H), 1.00 (s, 6H).

Example 18

Compound 18: (S)-3-(1-((4-((dimethylamino)methyl)phenoxy)methyl)-4-oxo-4H-thieno[3,4-c]pyrrol-5(6H)-yl)piperidine-2,6-dione

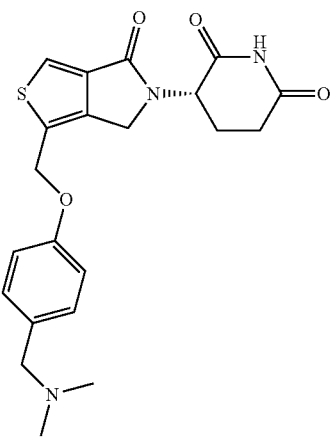 [SMILES: CN(C)Cc1ccc(OCc2scc3c2CN([C@H]2CCC(=O)NC2=O)C3=O)cc1]

To a solution of (S)-tert-butyl 5-amino-4-(1-((4-formylphenoxy) methyl)-4-oxo-4H-thieno[3,4-c]pyrrol-5(6H)-yl)-5-oxopentanoate (493 mg, 1.0 mmol) in DCM (10 mL) was added TFA (5 mL). After 2 h, the mixture was concentrated. The residue was dissolved in ACN (10 mL) and CDI (810 mg, 5 mmol) was added. The resulting mixture was heated at reflux overnight. After adding water, the mixture was extracted with EA, and the combined organic layers were concentrated to give (S)-4-((5-(2,6-dioxopiperidin-3-yl)-4-oxo-5,6-dihydro-4H-thieno[3,4-c]pyrrol-1-yl)methoxy)benzaldehyde (150 mg, 39% yield) as a solid. MS (ESI) m/z 385 [M+H]$^+$.

To a mixture of (S)-4-((5-(2,6-dioxopiperidin-3-yl)-4-oxo-5,6-dihydro-4H-thieno[3,4-c]pyrrol-1-yl)methoxy)benzaldehyde (80 mg, 0.21 mmol) with dimethylamine (0.12 mL, 0.25 mmol) in THF (3 mL) was added NaBH$_3$CN (27 mg, 0.42 mmol). After stirring overnight, the mixture was concentrated, and the residue was purified by prep-HPLC as previously described to afford Compound 18 (19.4 mg, 22% yield) as a solid. MS (ESI) m/z 414.1 [M+H]$^+$. $^1$H NMR (400 MHz, DMSO-d$_6$) δ 10.97 (s, 1H), 8.01 (s, 1H), 7.20 (d, 2H), 6.97 (d, 2H), 5.28 (s, 2H), 5.01 (m, 1H), 4.28 (q, 2H), 2.87 (m, 1H), 2.56 (m, 1H), 2.34 (m, 1H), 2.11 (s, 6H), 1.99 (m, 1H).

Example 19

Compound 19: (3S)-3-(1-((4-((3,5-dimethylmorpholino)methyl)phenoxy)methyl)-4-oxo-4H-thieno[3,4-c]pyrrol-5(6H)-yl)piperidine-2,6-dione

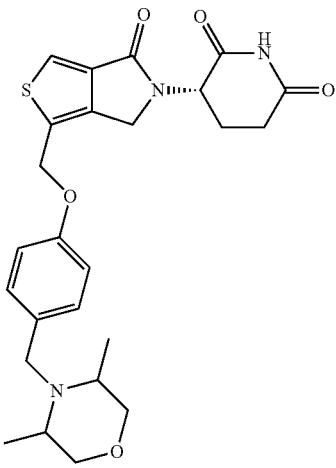 [SMILES: CC1COCC(C)N1Cc1ccc(OCc2scc3c2CN([C@H]2CCC(=O)NC2=O)C3=O)cc1]

To a solution of (S)-tert-butyl 5-amino-4-(1-(chloromethyl)-4-oxo-4H-thieno[3,4-c]pyrrol-5(6H)-yl)-5-oxopentanoate (300 mg, 0.805 mmol) in ACN (7 mL) was added 4-hydroxybenzaldehyde (108.2 mg, 0.8859 mmol) and K$_2$CO$_3$ (222.3 mg, 0.4027 mmol). After heating at 80° C. for 2 h, the mixture was concentrated, and the residue was purified using silica gel eluting with PE/EA (1:2) to give (S)-tert-butyl 5-amino-4-(1-((4-formylphenoxy)methyl)-4-oxo-4H-thieno[3,4-c]pyrrol-5(6H)-yl)-5-oxopentanoate (358 mg, 97% yield) as a solid. MS (ESI) m/z 459 [M+H]$^+$.

To a solution of (S)-tert-butyl 5-amino-4-(1-((4-formylphenoxy)methyl)-4-oxo-4H-thieno[3,4-c]pyrrol-5(6H)-yl)-5-oxopentanoate (257 mg, 0.561 mmol) in DCM (8 mL) at 0° C. was added TFA (3 mL). After 8 h at RT, the mixture was concentrated. The residue was dissolved with ACN (8 mL) and CDI (363.6 mg, 2.244 mmol) was added. The mixture was heated at 80° C. overnight then concentrated. The residue was purified using silica gel eluting with PE/EA (1:2) to give (S)-4-((5-(2,6-dioxopiperidin-3-yl)-4-oxo-5,6-dihydro-4H-thieno[3,4-c]pyrrol-1-yl)methoxy)benz aldehyde (188 mg, 87% yield) as a solid. MS (ESI) m/z 385 [M+H]$^+$.

To a solution of (S)-4-((5-(2,6-dioxopiperidin-3-yl)-4-oxo-5,6-dihydro-4H-thieno[3,4-c]pyrrol-1-yl)methoxy)benzaldehyde (143 mg, 0.372 mmol) in THF (5 mL) at 0° C. was added 3,5-dimethylmorpholine (85.7 mg, 0.745 mmol), tetraethyl titanate (254.8 mg, 1.117 mmol) and NaBH(OAc)$_3$ (394.7 mg, 1.862 mmol). After heating at reflux for 2 d, the mixture was concentrated. The residue was purified using silica gel eluting with MeOH in DCM (0% to 8%) then further purified by prep-HPLC as previously described to afford Compound 19 (52.1 mg, 23% yield) as a solid. MS (ESI) m/z 484 [M+H]⁺. ¹H NMR (400 MHz, DMSO-d₆) δ 10.97 (s, 1H), 8.02 (s, 1H), 7.26 (d, J=8.8 Hz, 2H), 6.96 (d, J=8.4 Hz, 2H), 5.27 (s, 2H), 4.99-5.04 (m, 1H), 4.24-4.37 (m, 2H), 3.84 (d, J=13.6 Hz, 1H), 3.53-3.56 (m, 2H), 3.21-3.26 (m, 3H), 2.84-2.93 (m, 1H), 2.67 (s, 2H), 2.56-2.65 (m, 1H), 2.31-2.35 (s, 1H), 1.97-2.00 (s, 1H), 0.92 (d, J=6.4 Hz, 6H).

Example 20

Compound 20: (S)-5-(2,6-dioxopiperidin-3-yl)-1-((4-(morpholinomethyl)phenoxy)methyl)-4H-thieno[3,4-c]pyrrole-4,6(5H)-dione

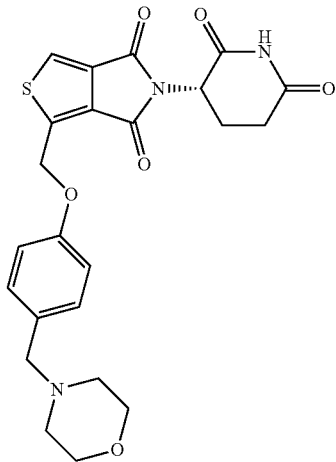 [SMILES: O=C1CC[C@H](N2C(=O)c3csc(COc4ccc(CN5CCOCC5)cc4)c3C2=O)C(=O)N1]

To dimethyl 2-cyanothiophene-3,4-dicarboxylate (1.90 g, 8.44 mmol) in a solution of AcOH (8 mL), pyridine (16 mL), and water (8 mL) at 0° C. was added NaH₂PO₂ (5.80 g, 67.6 mmol) and Raney Ni (1.0 g). The mixture was stirred at RT for 3 h then filtered. The filtrate was extracted with DCM, and the combined organic layers were washed with 1 N HCl, dried over Na₂SO₄, filtered, and concentrated to give dimethyl 2-formylthiophene-3,4-dicarboxylate (1.0 g, 52% yield) which was used in the next step without purification. MS (ESI) m/z 229.0[M+1]⁺.

To a solution of dimethyl 2-formylthiophene-3,4-dicarboxylate (1.0 g, 4.4 mmol) in MeOH (10 mL) at 0° C. was added sodium borohydride (250 mg, 6.6 mmol) in portions. After 2 h at RT, the mixture was concentrated to give dimethyl 2-(hydroxymethyl)thiophene-3,4-dicarboxylate (1.0 g, crude) as a gum which was used in the next step without purification. MS (ESI) m/z 231.1[M+H]⁺.

To a solution of dimethyl 2-(hydroxymethyl)thiophene-3,4-dicarboxylate (1.0 g, 4.4 mmol, crude) in toluene (10 mL) was added thionyl chloride (10 mL, 50 mmol) dropwise. The mixture was stirred at 80° C. overnight then concentrated, and the residue was purified using silica gel eluting with PE/EA (4:1) to give dimethyl 2-(chloromethyl)thiophene-3,4-dicarboxylate (905 mg, 83% yield). MS (ESI) m/z 249.0 [M+H]⁺.

To a solution of dimethyl 2-(chloromethyl)thiophene-3,4-dicarboxylate (810 mg, 3.26 mmol) in THF (5 mL) at 0° C. was added sodium hydride (60% dispersion in mineral oil, 196 mg, 3.92 mmol) in portions. The mixture was degassed and purged with N₂. After 30 m at 0° C., a solution of 4-(morpholinomethyl)phenol (756 mg, 3.92 mmol) in THF (5 ml) was added. After 16 h at 80° C., the mixture was concentrated, and the residue was purified using silica gel eluting with PE/EA (4:1) to give dimethyl 2-((4-(morpholinomethyl)phenoxy)methyl)thiophene-3,4-dicarboxylate (604 mg, 46% yield) as a solid. MS (ESI) m/z 406.1 [M+H]⁺.

To a mixture of dimethyl 2-((4-(morpholinomethyl)phenoxy)methyl)thiophene-3,4-dicarboxylate (857 mg, 2.12 mmol) in THF (4 mL) and H₂O (4 mL) was added LiOH monohydrate (444 mg, 10.58 mmol). After 16 h, the mixture was concentrated then diluted with water and acidified with 1N HCl to a pH of 2. The mixture was filtered and the filter cake was washed with water and dried to give a 2-((4-(morph olinomethyl)phenoxy)methyl)thiophene-3,4-dicarboxylic acid (604 mg, 76% yield) as a solid which was used in the next step without purification. MS (ESI) m/z 378.1 [M+H]⁺.

A mixture of 2-((4-(morpholinomethyl)phenoxy)methyl)thiophene-3,4-dicarboxylic acid (604 mg, 1.6 mmol) in acetic anhydride (15 mL) was heated at 80° C. for 4 h then concentrated to give 4-((4-(morpholinomethyl)phenoxy)methyl)thieno[3,4-c]furan-1,3-dione (574 mg, crude) as an oil which was used in the next step without purification.

To a solution of 4-((4-(morpholinomethyl)phenoxy)methyl)thieno[3,4-c]furan-1,3-dione (574 mg, 1.6 mmol, crude) in THF (20 mL) was added (S)-t-butyl 4,5-diamino-5-oxopentanoate hydrochloride (381 mg, 1.6 mmol) and DIEA (250 mg, 1.92 mmol). After 4 h, CDI (312 mg, 1.92 mmol) and DMAP (20 mg, 0.16 mmol) were added, and the mixture was heated at reflux for 6 h then concentrated. The residue was purified using silica gel column eluting with PE/EA (1:1) to give (S)-tert-butyl 5-amino-4-(1-((4-(morpholinomethyl)phenoxy)methyl)-4,6-dioxo-4H-thieno[3,4-c]pyrrol-5(6H)-yl)-5-oxopentanoate (260 mg, 28% yield) as a solid. MS (ESI) m/z 544.2 [M+H]⁺.

To a solution of (S)-tert-butyl 5-amino-4-(1-((4-(morpholinomethyl)phenoxy)methyl)-4,6-dioxo-4H-thieno[3,4-c]pyrrol-5(6H)-yl)-5-oxopentanoate (260 mg, 0.48 mmol) in DCM (6 mL) was added TFA (2 mL). After 16 h, the mixture was concentrated to give (S)-5-amino-4-(1-((4-(morpholinomethyl)phenoxy)methyl)-4,6-dioxo-4H-thieno[3,4-c]pyrrol-5(6H)-yl)-5-oxopentanoic acid (233 mg, quant.) as a solid. MS (ESI) m/z 488.1 [M+H]⁺.

To a solution of (S)-5-amino-4-(1-((4-(morpholinomethyl)phenoxy)methyl)-4,6-dioxo-4H-thieno[3,4-c]pyrrol-5(6H)-yl)-5-oxopentanoic acid (233 mg, 0.48 mmol) in ACN (10 mL) was added CDI (233 mg, 1.44 mmol). After 16 h at 80° C., the mixture was concentrated then purified using silica gel eluting with PE/EA (1:1) followed by prep-HPLC as previously described to afford Compound 20 (64 mg, 29% yield) as a solid. MS (ESI) m/z 469.9 [M+H]⁺. ¹HNMR (DMSO-d₆, 400 MHz) δ 11.09 (s, 1H), δ 8.40 (s, 1H), 7.24 (d, J=8.4 Hz, 2H), 7.01 (d, J=8.8 Hz, 2H), 5.50 (s, 2H), 5.07 (dd, J=5.6, 7.2 Hz, 1H), 3.55 (t, J=4.8 Hz, 4H), 3.39 (s, 2H), 2.91-2.83 (m, 1H), 2.60-2.54 (m, 1H), 2.50-2.47 (m, 1H), 2.32 (t, J=4.4 Hz, 4H), 2.07-2.02 (m, 1H).

Example 21

Compound 21: (S)-3-(1-((3-fluoro-4-(morpholinomethyl)phenoxy)methyl)-4-oxo-4H-thieno[3,4-c]pyrrol-5(6H)-yl)piperidine-2,6-dione

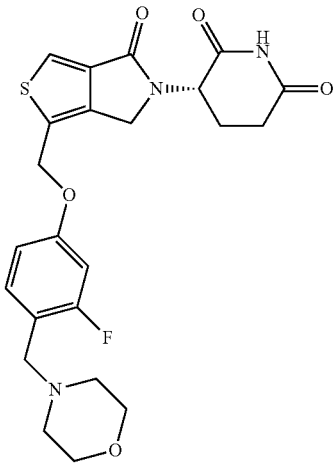 [SMILES: O=C1CC[C@H](N2Cc3c(csc3COc3ccc(CN4CCOCC4)c(F)c3)C2=O)C(=O)N1]

A mixture of 3-fluoro-4-hydroxybenzaldehyde (1.4 g, 10 mmol) and morpholine (1.3 g, 15 mmol) in DCM (30 mL) was stirred for 0.5 h then NaBH$_3$CN (1.3 g, 20 mmol) was added. After 0.5 h, the mixture was washed with water and the organic layer was concentrated. The residue was purified using silica gel eluting with PE/EA (1:1) to give 3-fluoro-4-(morpholinomethyl)phenol (1.1 g, 52% yield) as an oil. MS (ESI) m/z 212 [M+H]$^+$.

To a solution of (S)-tert-butyl 5-amino-4-(1-(chloromethyl)-4-oxo-4H-thieno[3,4-c]pyrrol-5(6H)-yl)-5-oxopentanoate (100 mg, 0.27 mmol) and 3-fluoro-4-(morpholinomethyl)phenol (68 mg, 0.32 mmol) in ACN (5 mL), was added K$_2$CO$_3$ (75 mg, 0.54 mmol). After heating at reflux for 4 h, the reaction was quenched with water and extracted with EA. The combined organic layers were concentrated to give (S)-tert-butyl 5-amino-4-(1-((3-fluoro-4-(morpholinomethyl)phenoxy)methyl)-4-oxo-4H-thieno[3,4-c]pyrrol-5 (6H)-yl)-5-oxopentanoate (180 mg, crude) an oil. MS (ESI) m/z 548 [M+H]$^+$.

To a solution of (S)-tert-butyl 5-amino-4-(1-((3-fluoro-4-(morpholinomethyl)phenoxy)methyl)-4-oxo-4H-thieno[3,4-c]pyrrol-5 (6H)-yl)-5-oxopentanoate (160 mg, 0.27 mmol, crude) in DCM (5 mL) was added TFA (2 mL). After 3 h, the mixture was concentrated. The residue was dissolved in ACN (5 mL) and CDI (216 mg, 1.35 mmol) was added. After heating at reflux for 2 d, the mixture was washed with water and extracted with EA. The combined organic layers were concentrated and purified by prep-HPLC as previously described to afford Compound 21 (36.7 mg, 29% yield) as a solid. MS (ESI) m/z 474.1 [M+H]$^+$. $^1$H NMR (400 MHz, DMSO-d$_6$) δ 10.97 (s, 1H), 8.03 (s, 1H), 7.30 (dd, 1H), 6.91 (dd, 1H), 6.85 (dd, 1H), 5.31 (s, 2H), 5.02 (m, 1H), 4.27 (q, 2H), 3.54 (t, 4H), 3.43 (s, 2H), 2.87 (m, 1H), 2.58 (m, 1H), 2.33 (m, 1H), 2.32 (t, 4H), 1.99 (m, 1H).

Compounds 22-31 may be prepared following similar synthetic procedures described in Examples 1-21.

Example 22. Biological Assays

Western Blot Analysis

MV-4-11 cells were grown in RPMI 1640 media supplemented with 10% fetal bovine serum, streptomycin and penicillin.

Cells were cultured at approximately 10$^6$ cells per mL and incubated in DMSO or the indicated compound for 6-8 hours. Whole cell extracts were prepared using RIPA buffer according to manufacturer's protocol (Pierce). Briefly, 3×10$^6$ cells were washed once in PBS, the cell pellets were resuspended in RIPA buffer and allowed to incubate for 15 minutes on ice. Cells debris was removed by centrifugation and the cleared whole cell lysates were transferred to new tubes for further analysis.

For Western blot analysis, whole cell protein extracts were separated on 4-12% SDS-polyacrylamide gels, transferred to nitrocellulose and probed with the indicated primary antibodies. Membranes were subsequently washed and probed with the appropriate IRDye secondary antibodies (LI-COR). The signal was detected using the Odyssey Imaging System (LI-COR).

The following antibodies were used in these studies: Anti-eRF3/GSPT1: Abcam, ab126090 (Cambridge, Mass.); Anti-Ikaros: Abcam, ab191394 (Cambridge, Mass.); Anti-CK1α: Abcam, ab108296 (Cambridge, Mass.); β-actin (8H10D10) mouse monoclonal antibody: Cell Signaling Technology, #3700 (Danvers, Mass.); IRDye 680RD Goat anti-rabbit antibody: LI-COR, 926-68071 (Lincoln, Nebr.); IRDye 800CW Goat anti-mouse antibody: LI-COR, 926-32210 (Lincoln, Nebr.).

IKAROS activity is shown in Table 1 and 2. CK-1a activity is shown in Table 3. GSPT1 activity is shown in Table 4. In each of Tables 1-4, the % degradation values are reported as "A", "B", "C", or "D". "A" represents a % degradation value of less than 25% (value<25%). "B" represents a % degradation value of equal to or more than 25% and less than 50% (25%≤value<50%). "C" represents a % degradation value of equal to or more than 50% and less than 75% (50%≤value <75%). "D" represents a % degradation value of equal to or more than 75% (value≥75%).

TABLE 1

Activity of Compounds in IKAROS degradation assay. Compounds tested at 10 μM.

| Compound No. | IKAROS % Degradation at 10 μM |
|---|---|
| 3 | C |
| 14 | B |
| 16 | A |
| 18 | C |
| 20 | B |

TABLE 2

Activity of Compounds in IKAROS degradation assay. Compounds tested at 1 μM.

| Compound No. | IKAROS % Degradation at 1 μM |
|---|---|
| 1 | D |
| 4 | B |
| 6 | B |
| 7 | C |
| 8 | B |

TABLE 2-continued

Activity of Compounds in IKAROS degradation assay. Compounds tested at 1 μM.

| Compound No. | IKAROS % Degradation at 1 μM |
|---|---|
| 13 | B |
| 15 | B |
| 17 | C |
| 19 | C |

TABLE 3

Activity of Compounds * in CK1α degradation assay. Compounds tested at 1 μM.

| Compound No. | CK1α % Degradation at 1 μM |
|---|---|
| 1 | D |
| 4 | B |
| 13 | C |
| 14 | C |
| 15 | B |
| 17 | D |
| 18 | D |
| 19 | D |

TABLE 4

Activity of Compounds * in GSPT1 degradation assay. Compounds tested at 1 μM.

| Compound No. | GSPT1 % Degradation at 1 μM |
|---|---|
| 1 | C |
| 2 | B |
| 4 | B |
| 19 | C |

Cell-Based Assay

Either frozen primary blood mononuclear cells (PBMCs) or frozen CD14+ mobilized peripheral blood monocytes were purchased from AllCells (PB003F, Normal Peripheral Blood MNC (Alameda, Calif.)). Cells were quick thawed, washed 1-time with RPMI-1640 (10% FBS/1% Pen-Strep) and plated in 96 well plates at 200,000 cells per well. Cells were pretreated with DMSO only or with the indicated compound for 1 h and then induced with 100 ng/mL lipopolysaccharide (LPS) for 18-24 h. The supernatant was analyzed for IL-1β, IL-6, and TNFα, using Meso Scale assay according to manufacturer's protocol. The negative control wells were treated with DMSO.

For the IL-2 analysis, 96 well plates were precoated with 1 μg/mL anti-human CD3 antibody (OKT3, eBioscience Inc., San Diego, Calif.). After washing with PBS, the indicated compound was added (50 μL/well) followed by PBMCs diluted at 3-4 million cells/mL (150 μL/well). Plates were incubated for 24 h and the supernatants collected for Mesoscale IL-2 analysis. IL-2 activity is measured as fold difference from the DMSO control.

IL-1β activity is shown in Table 5. IL-6 activity is shown in Table 6. TNFα activity is shown in Table 7. IL-2 activity is shown in Table 8. In each of Tables 5-7, the % inhibition values are reported as "A", "B", "C", or "D". "A" represents a % inhibition value of less than 50% (value <50%). "B" represents a % inhibition value of equal to or more than 50% and less than 70% (50%≤value<70%). "C" represents a % inhibition value of equal to or more than 70% and less than 90% (70%≤value<90%). "D" represents a % inhibition value of equal or more than 90% (value≥90%). In Table 8, the fold-change values are reported as "A", "B", "C", or "D". "A" represents a fold-change value of equal to or less than 1 (value≤1). "B" represents a fold-change value of more than 1 and equal to or less than 2 (1<value≤2). "C" represents a fold-change value of more than 2 and equal to or less than 3 (2<value≤3). "D" represents a fold-change value of more than 3 (value>3).

TABLE 5

Activity of Compounds in IL-1β inhibition assay. Compounds tested at 10 μM.

| Compound No. | Il-1β % Inhibition at 10 μM |
|---|---|
| 1 | D |
| 2 | A |
| 6 | C |
| 7 | C |
| 8 | D |
| 9 | C |
| 10 | C |
| 13 | D |
| 14 | C |
| 15 | D |
| 17 | C |
| 18 | B |
| 19 | C |
| 20 | B |

TABLE 6

Activity of Compounds * in IL-6 inhibition assay. Compounds tested at 10 μM.

| Compound No. | IL-6 % Inhibition at 10 μM |
|---|---|
| 1 | B |
| 6 | A |
| 8 | C |
| 9 | A |
| 10 | A |
| 13 | B |
| 14 | A |
| 15 | B |
| 17 | A |
| 19 | A |

TABLE 7

Activity of Compounds in TNF-α inhibition assay. Compounds tested at 10 μM.

| Compound No. | TNF-α % Inhibition at 10 μM |
|---|---|
| 2 | A |
| 3 | A |
| 6 | C |
| 7 | C |
| 8 | D |
| 9 | D |
| 10 | D |
| 11 | A |
| 12 | A |
| 13 | D |
| 14 | C |
| 15 | C |
| 16 | A |
| 17 | D |

TABLE 7-continued

Activity of Compounds in TNF-α inhibition assay. Compounds tested at 10 µM.

| Compound No. | TNF-α % Inhibition at 10 µM |
|---|---|
| 18 | C |
| 19 | C |
| 20 | B |

TABLE 8

Activity of Compounds * in IL-2 fold-change assay. Compounds tested at 10 µM.

| Compound No. | IL-2 Fold-Change at 10 µM |
|---|---|
| 1 | B |
| 2 | B |
| 3 | A |
| 4 | C |
| 5 | B |
| 6 | C |
| 7 | C |
| 8 | C |
| 9 | D |
| 10 | C |
| 11 | B |
| 12 | B |
| 13 | C |
| 14 | C |
| 15 | D |
| 16 | A |
| 17 | B |
| 18 | C |
| 19 | A |
| 20 | B |

Cell Viability Assay

MOLM-13 cells were cultured in RPMI 1640 media supplemented with 10% fetal bovine serum, streptomycin and penicillin, and were plated in white walled 96-well plates at 2500 cells/well. Cells were incubated in DMSO (control) or the indicated compound for 3 days at 37° C. and 5% $CO_2$. Following the incubation period, 100 µL of Cell-TiterGlow (CTG) reagent (CellTiter-Glo® Luminescent Cell Viability Assay, Promega (Madison, Wis.)) was added to each well. Following a 10 minutes incubation with shaking, luminescence was measured using the EnVision Multimode plate reader.

Antiproliferative activity of compounds in MOLM-13 cell viability assay is shown in Table 9. The MOLM-13 cell viability values as % DMSO are reported as "A", "B", "C", or "D". "A" represents a % viability value of less than 25% (value<25%). "B" represents a % viability value of equal to or more than 25% and less than 50% (25%≤value<50%). "C" represents a % viability value of equal to or more than 50% and less than 75% (50%≤value<75%). "D" represents a % viability value of equal or more than 75% (value≥75%). The results indicated that the compounds inhibited cancer cell viability, such as leukemia cell viability.

TABLE 9

Activity of Compounds in MOLM-13 cell viability assays. Compounds tested at 10 µM.

| Compound No. | MOLM-13 Cell Viability % DMSO at 10 µM |
|---|---|
| 1 | C |
| 10 | B |
| 11 | A |
| 13 | C |
| 14 | C |
| 17 | C |
| 18 | A |
| 19 | C |
| 20 | A |

What is claimed is:

1. A compound of Formula (I):

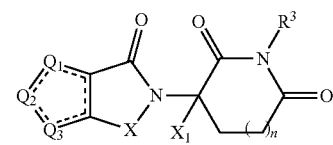

(I)

or a pharmaceutically acceptable salt thereof, wherein:
one of $Q_1$, $Q_2$, and $Q_3$ is S; one of $Q_1$, $Q_2$, and $Q_3$ is $CR^1$; and one of $Q_1$, $Q_2$, and $Q_3$ is $CR^2$;
each ═══ is a carbon-carbon single bond, a carbon-carbon double bond, or a carbon-sulfur single bond;
$R^1$ is H, deuterium, hydroxyl, halogen, cyano, nitro, optionally substituted $C_1$-$C_6$ alkoxy, optionally substituted $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, optionally substituted amino, $C_1$-$C_6$ alkylamino, amino($C_1$-$C_6$ alkyl), ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_8$ carbocyclyl;
$R^2$ is

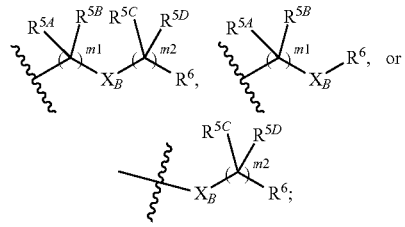

wherein each $X_B$ is independently O, S, or $NR^{5E}$; each $R^{5A}$, $R^{5B}$, $R^{5C}$, $R^{5D}$, and $R^{5E}$ is independently H, deuterium, halogen, $C_1$ to $C_6$ alkyl, or $C_1$-$C_6$ haloalkyl; and each m1 and m2 is an integer of 1;
$R^3$ is H, deuterium, optionally substituted $C_1$-$C_6$ alkyl,

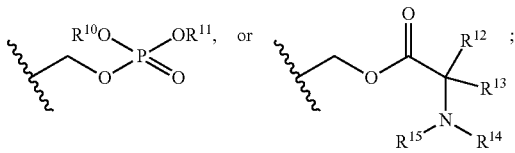

X is C=O, CHR$^{4A}$, or CR$^{4A}$R$^{4B}$;

each R$^{4A}$ and R$^{4B}$ is independently H, deuterium, or C$_1$-C$_6$ alkyl;

X$_1$ is H, deuterium, fluoro, or C$_1$-C$_6$ alkyl;

n is an integer of 0, 1, or 2;

each R$^6$ is independently C$_6$-C$_{10}$ aryl or 5 to 10 membered heteroaryl, each of which is substituted with one or more substituents, each substituent independently selected from the group consisting of halogen, hydroxyl, C$_1$-C$_6$ alkyl, C$_1$-C$_6$ haloalkyl, C$_1$-C$_6$ alkylamino, amino(C$_1$-C$_6$ alkyl), C$_3$-C$_7$ cycloalkyl optionally substituted with one or more R$^9$, C$_3$-C$_7$ cycloalkyl (C$_1$-C$_6$ alkyl) optionally substituted with one or more R$^9$, heterocyclyl optionally substituted with one or more R$^9$, and heterocyclyl(C$_1$-C$_6$ alkyl) optionally substituted with one or more R$^9$;

each R$^9$ is independently C$_1$-C$_6$ alkyl, C$_1$-C$_6$ haloalkyl, halogen, or cyano; or two geminal R$^9$ form oxo (=O); and each of R$^{10}$, R$^{11}$, R$^{12}$, R$^{13}$, R$^{14}$, and R$^{15}$ is independently H, optionally substituted C$_1$-C$_6$ alkyl, or C$_3$-C$_6$ cycloalkyl; or R$^{14}$ and R$^{15}$ together with the nitrogen atom to which they are attached form optionally substituted 5 or 6 membered heterocyclyl.

2. The compound of claim 1, wherein the compound is a compound of Formula (Ia), (Ib), (Ic), (Id), (Ie), or (If):

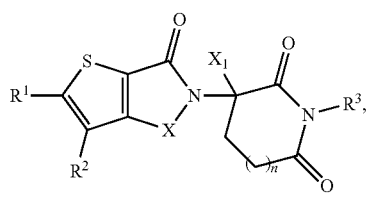
(Ia)

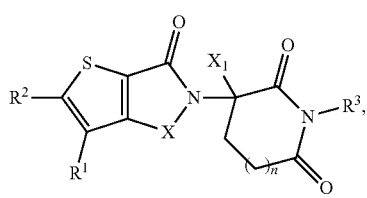
(Ib)

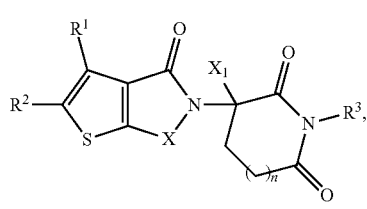
(Ic)

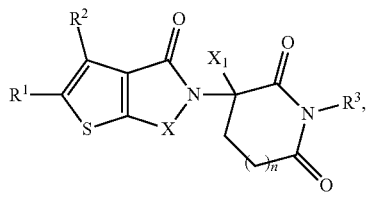
(Id)

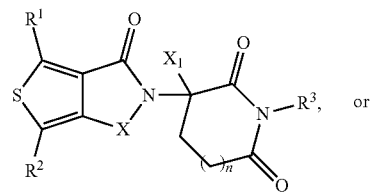
(Ie)

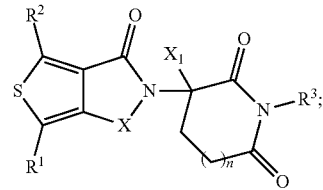
(If)

or a pharmaceutically acceptable salt thereof.

3. The compound of claim 2, wherein n is an integer of 1.

4. The compound of claim 2, wherein X$_1$ is CH$_2$.

5. The compound of claim 2, wherein X$_1$ is H.

6. The compound of claim 2, wherein R$^3$ is H.

7. The compound of claim 2, wherein R$^2$ is

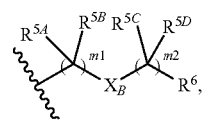

wherein X$^B$ is O or NR$^{5E}$.

8. The compound of claim 2, wherein R$^2$ is

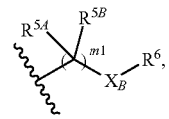

wherein X$^B$ is O or NR$^{5E}$.

9. The compound of claim 2, wherein R$^2$ is

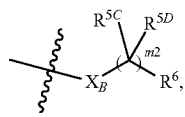

wherein X$^B$ is O or NR$^{5E}$.

10. The compound of claim 7, wherein each of R$_{5A}$, R$^{5B}$, R$^{5C}$, and R$^{5D}$ is hydrogen, or at least one of R$^{5A}$, R$^{5B}$, R$^{5C}$, and R$^{5D}$ is halogen or C$_1$-C$_6$ alkyl; and wherein R$^{5E}$ is H or methyl.

11. The compound of claim 8, wherein each of R$^{5A}$, R$^{5B}$, R$^{5C}$, and R$^{5D}$ is hydrogen, or at least one of R$^{5A}$, R$^{5B}$, R$^{5C}$, and R$^{5D}$ is halogen or C$_1$-C$_6$ alkyl; and wherein R$^{5E}$ is H or methyl.

12. The compound of claim 9, wherein each of R$^{5A}$, R$_{5B}$, R$^{5C}$, and R$^{5D}$ is H, or at least one of R$^{5A}$, R$^{5B}$, R$^{5C}$, and R$^{5D}$ is halogen or C$_1$-C$_6$ alkyl; and wherein R$^{5E}$ is H or methyl.

13. The compound of claim 2, wherein R$^1$ is H.

14. The compound of claim 2, wherein R$^6$ is C$_6$-C$_{10}$ aryl, which is optionally substituted with one or more substituents, each substituent independently selected from the group consisting of halogen, hydroxyl, $C_1$-$C_6$ alkyl, $C_1$-$C_6$ haloalkyl, $C_1$-$C_6$ alkylamino, amino($C_1$-$C_6$ alkyl), $C_3$-$C_7$cycloalkyl optionally substituted with one or more $R^9$, $C_3$-$C_7$cycloalkyl($C_1$-$C_6$ alkyl) optionally substituted with one or more $R^9$, heterocyclyl optionally substituted with one or more $R^9$, and heterocyclyl($C_1$-$C_6$ alkyl) optionally substituted with one or more $R^9$.

15. The compound of claim 2, wherein $R^6$ is phenyl or pyridyl, each of which is substituted with one, two, or three substituents, each substituent independently selected from the group consisting of halogen, $C_1$-$C_6$ alkyl, $C_1$-$C_6$ haloalkyl, $C_1$-$C_6$ alkylamino, amino($C_1$-$C_6$ alkyl), $C_3$-$C_7$ cycloalkyl optionally substituted with one or more $R^9$, $C_3$-$C_7$ cycloalkyl($C_1$-$C_6$ alkyl) optionally substituted with one or more $R^9$, 5 or 6 membered heterocyclyl optionally substituted with one or more $R^9$, and 5 or 6 membered heterocyclyl($C_1$-$C_6$ alkyl) optionally substituted with one or more $R^9$.

16. The compound of claim 15, wherein $R^6$ is phenyl substituted with

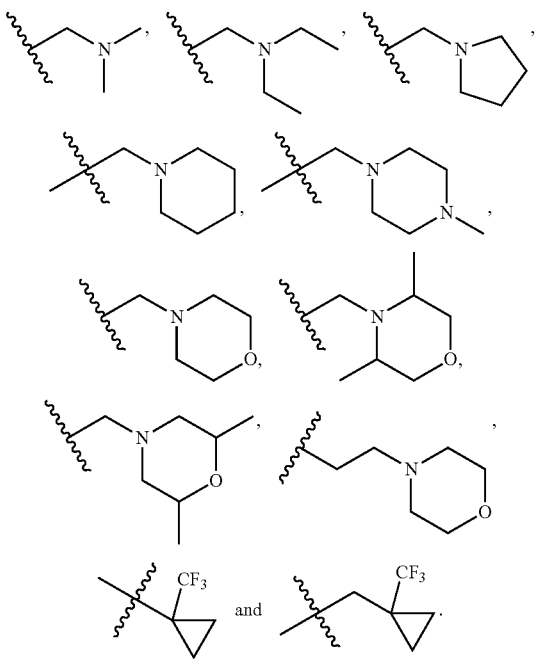

each of which is optionally substituted with one or more $R^9$.

17. The compound of claim 16, wherein each $R^9$ is independently halogen, $C_1$-$C_6$ alkyl, or $C_1$-$C_6$ haloalkyl.

18. The compound of claim 15, wherein $R^6$ is phenyl substituted with —NH($C_1$-$C_4$ alkyl), —N($C_1$-$C_4$ alkyl)$_2$, —(CH$_2$)$_{1-3}$—NH($C_1$-$C_4$ alkyl), or —(CH$_2$)$_{1-3}$—N($C_1$-$C_4$ alkyl)$_2$.

19. The compound of claim 15, wherein $R^6$ is phenyl substituted with one, two, or three substituents, each substituent independently selected from the group consisting of fluoro, chloro, methyl, ethyl, n-propyl, isopropyl, t-butyl, trifluoromethyl, —NH(Me), —NH(Et), —N(Me)$_2$, —N(Et)$_2$,

20. A compound of:

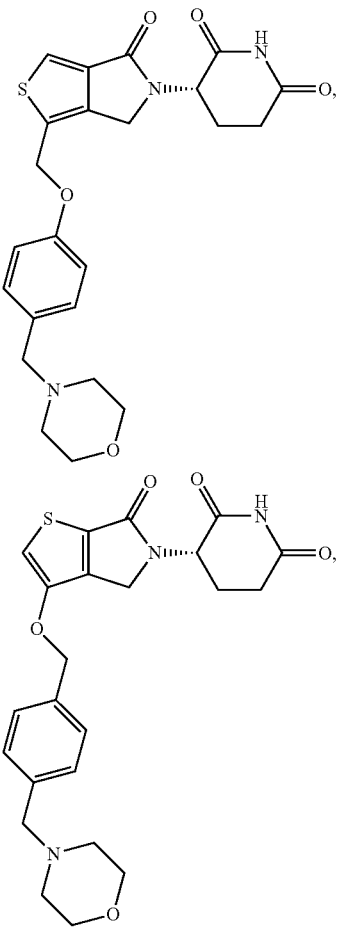

87
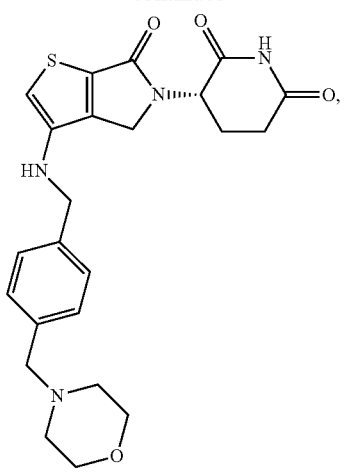
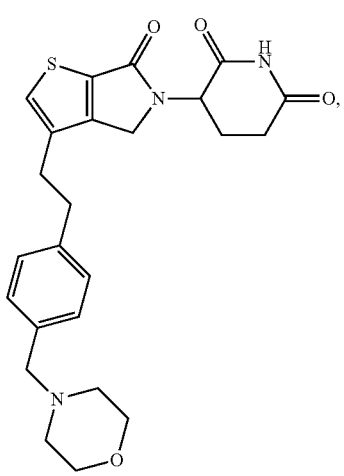
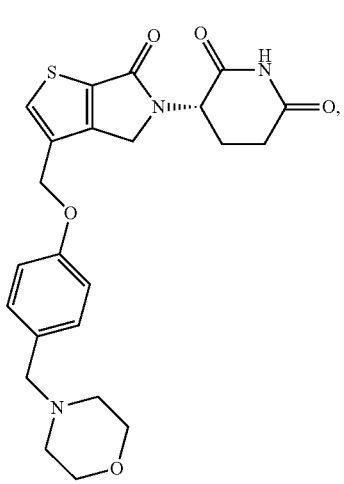
88
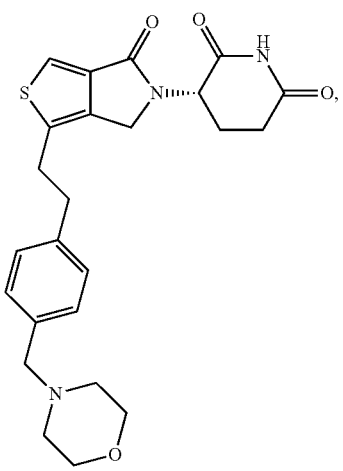
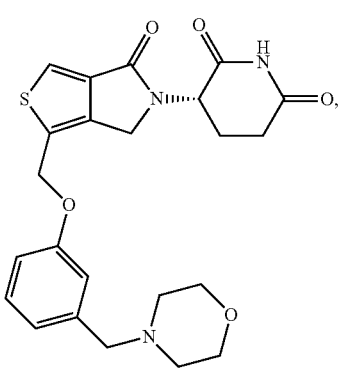
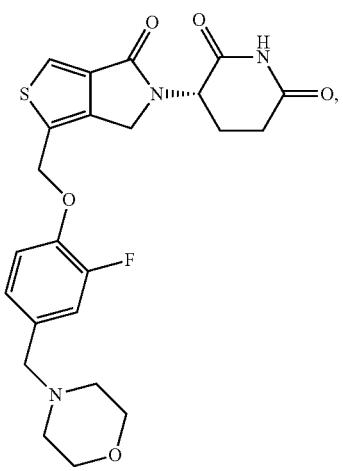

89
-continued
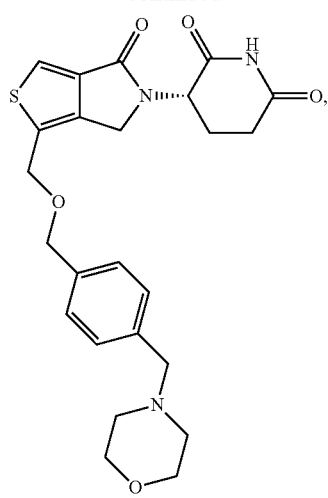
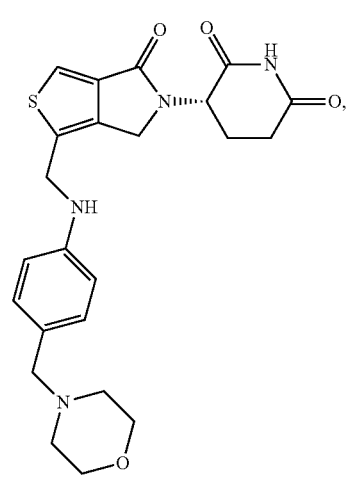
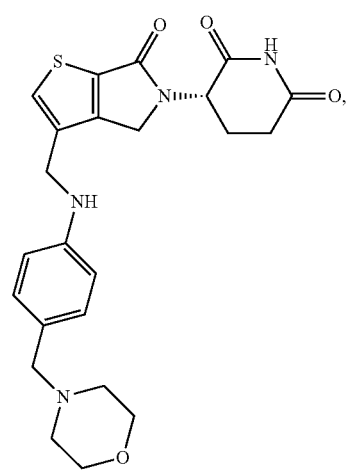
90
-continued
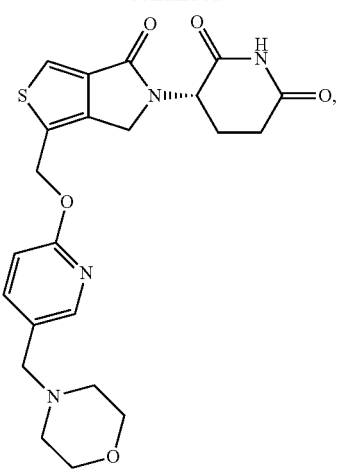
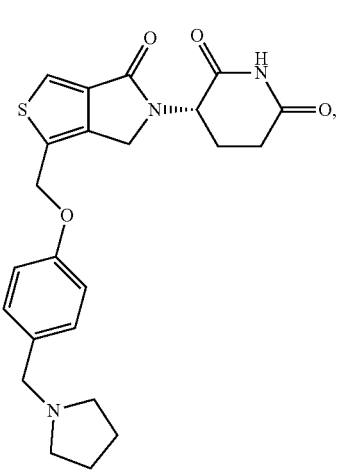
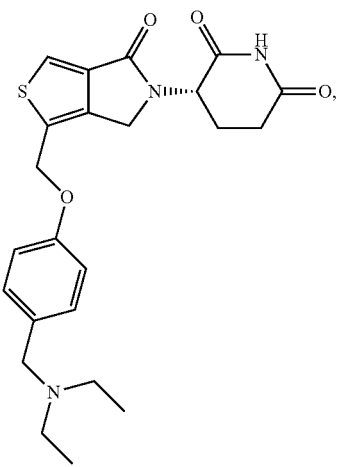

91
-continued
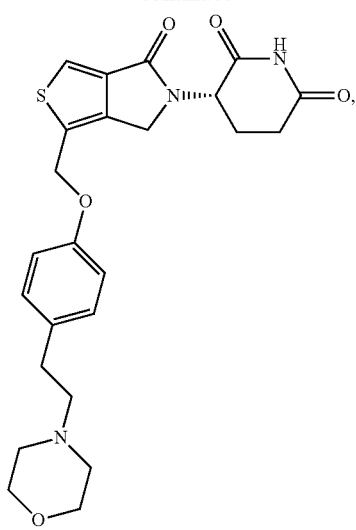
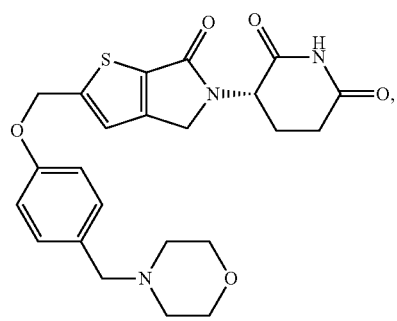
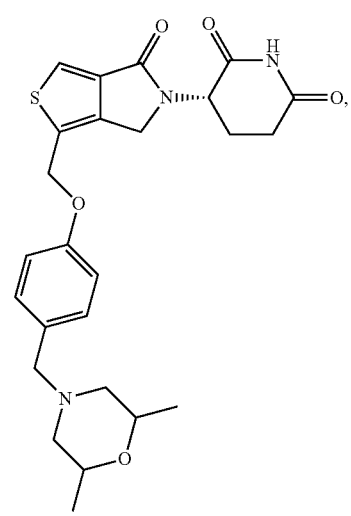
92
-continued
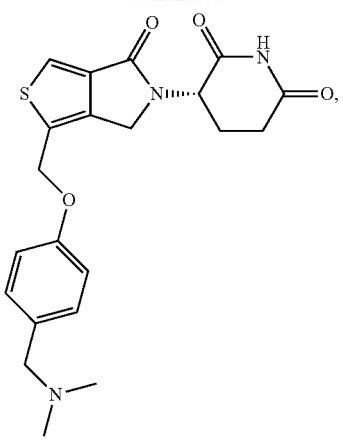
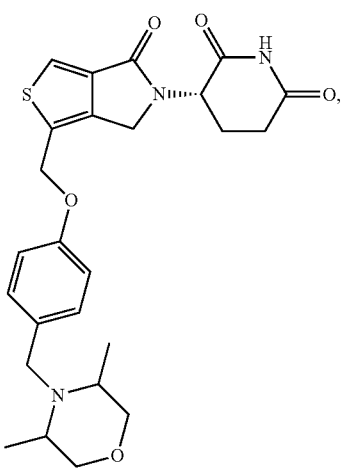
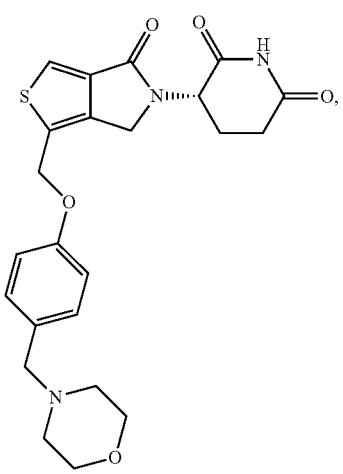

93
-continued
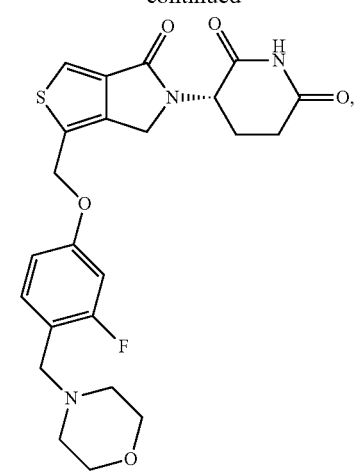
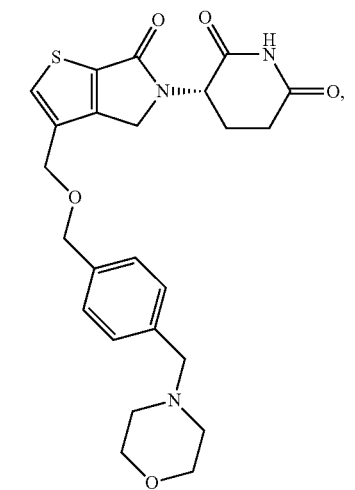
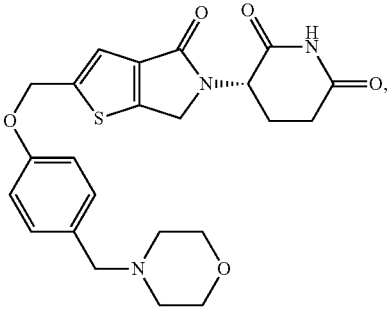
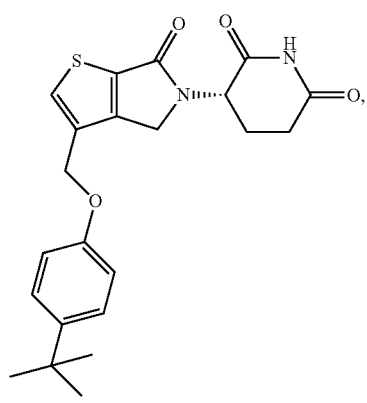
94
-continued
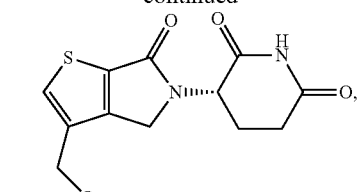
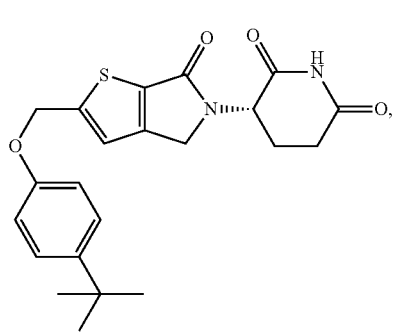
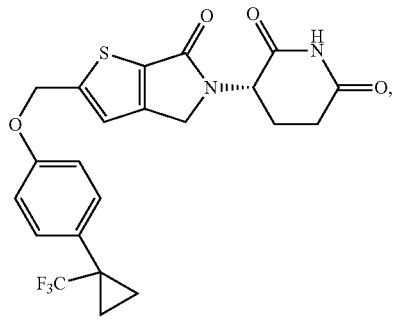
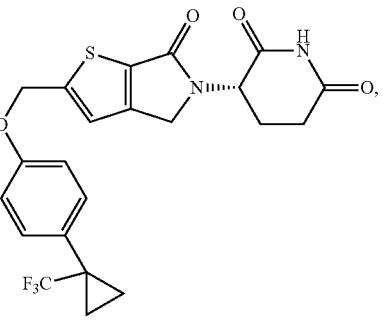
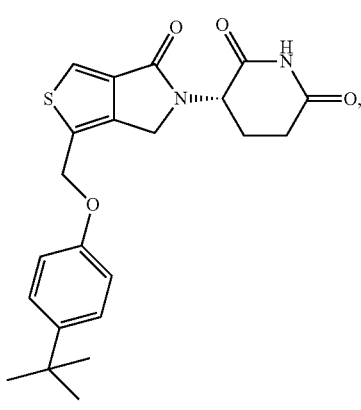

-continued

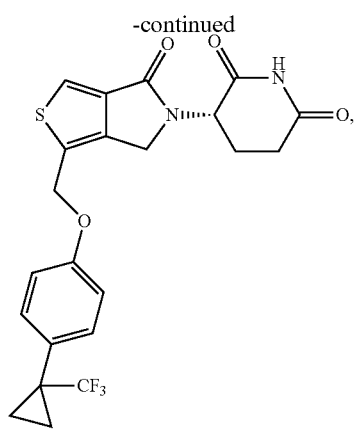

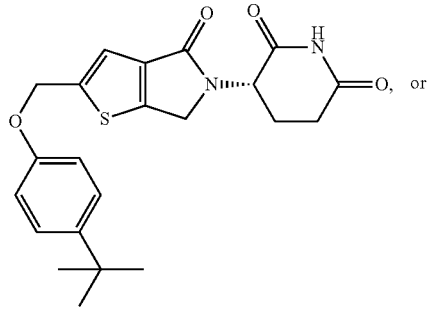

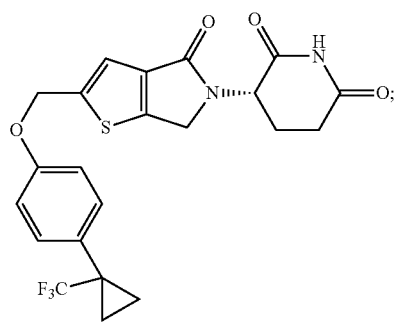

or a pharmaceutically acceptable salt thereof.

21. A pharmaceutical composition, comprising a compound of claim 1, or a pharmaceutically acceptable salt thereof, and at least one pharmaceutically acceptable carrier or excipient.

22. The compound of claim 1, wherein the compound is a compound of Formula (Ie):

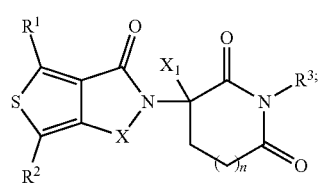

(Ie)

or a pharmaceutically acceptable salt thereof.

23. The compound of claim 22, wherein the compound is

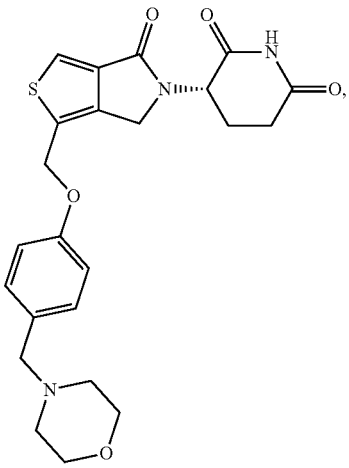

or a pharmaceutically acceptable salt thereof.

24. The compound of claim 22, wherein the compound is

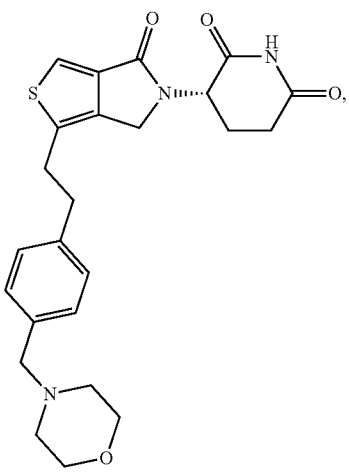

or a pharmaceutically acceptable salt thereof.

25. The compound of claim 22, wherein the compound is

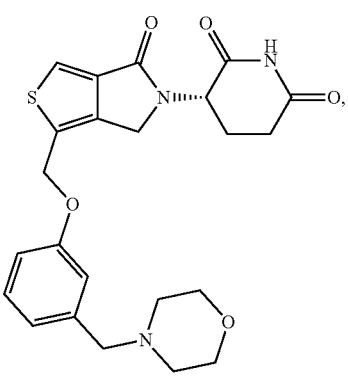

or a pharmaceutically acceptable salt thereof.

26. The compound of claim 22, wherein the compound is

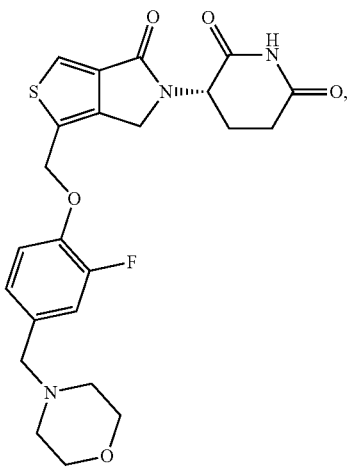

or a pharmaceutically acceptable salt thereof.

27. The compound of claim 22, wherein the compound is

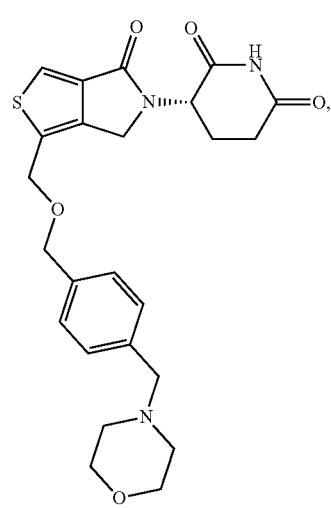

or a pharmaceutically acceptable salt thereof.

28. The compound of claim 22, wherein the compound is

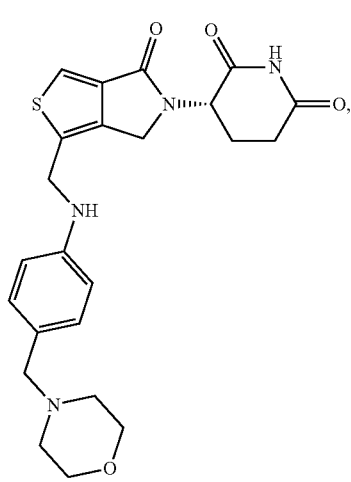

or a pharmaceutically acceptable salt thereof.

29. The compound of claim 22, wherein the compound is

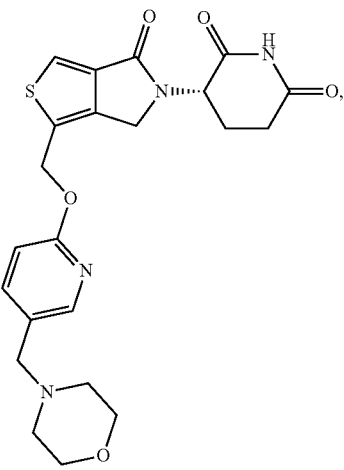

or a pharmaceutically acceptable salt thereof.

30. The compound of claim 22, wherein the compound is

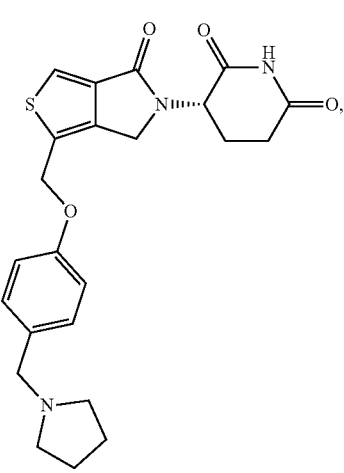

or a pharmaceutically acceptable salt thereof.

31. The compound of claim 22, wherein the compound is

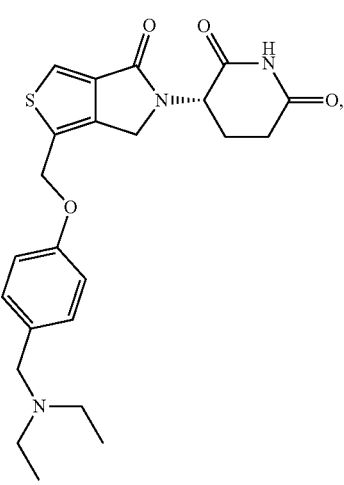

or a pharmaceutically acceptable salt thereof.

32. The compound of claim 22, wherein the compound is

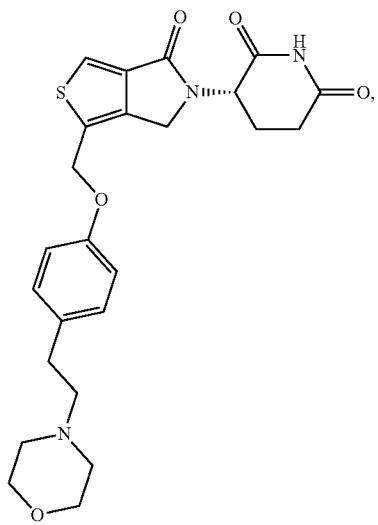

or a pharmaceutically acceptable salt thereof.

33. The compound of claim 22, wherein the compound is

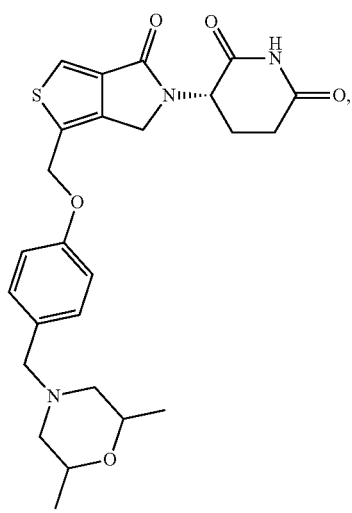

or a pharmaceutically acceptable salt thereof.

34. The compound of claim 22, wherein the compound is

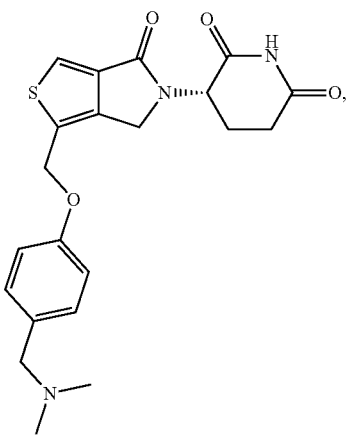

or a pharmaceutically acceptable salt thereof.

35. The compound of claim 22, wherein the compound is

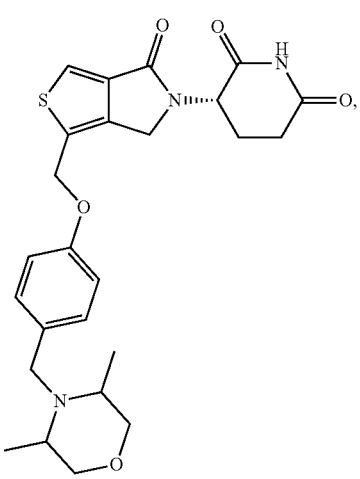

or a pharmaceutically acceptable salt thereof.

36. The compound of claim 22, wherein the compound is

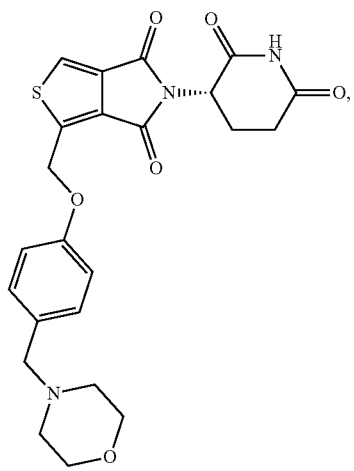

or a pharmaceutically acceptable salt thereof.

37. The compound of claim 22, wherein the compound is

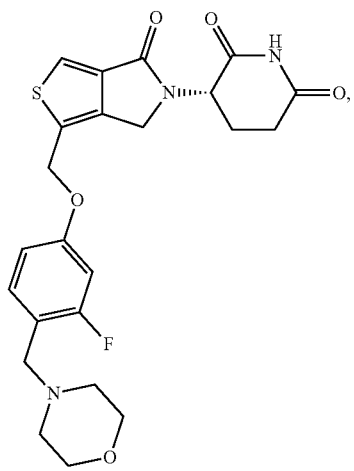

or a pharmaceutically acceptable salt thereof.

38. The compound of claim 22, wherein the compound is

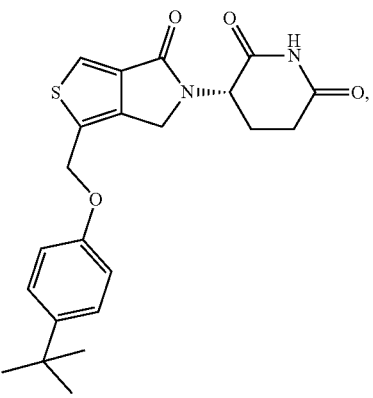

or a pharmaceutically acceptable salt thereof.

39. The compound of claim 22, wherein the compound is

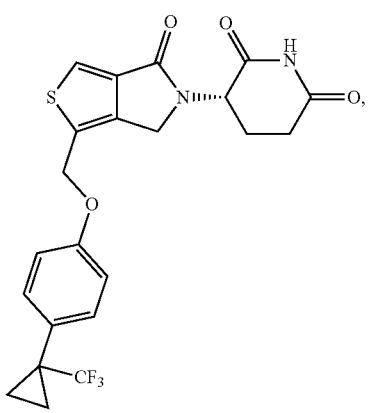

or a pharmaceutically acceptable salt thereof.

* * * * *